US012589158B2

(12) United States Patent
Zhang et al.

(10) Patent No.: US 12,589,158 B2
(45) Date of Patent: Mar. 31, 2026

(54) GLP-1/GIP DUAL AGONIST, PREPARATION METHOD AND USE THEREOF

(71) Applicant: HANGZHOU ZHONGMEIHUADONG PHARMACEUTICAL CO., LTD., Zhejiang (CN)

(72) Inventors: Nan Zhang, Zhejiang (CN); Chunhua Jiang, Zhejiang (CN); Dongzhou Liu, Zhejiang (CN); Li Teng, Zhejiang (CN); Jiale Shen, Zhejiang (CN)

(73) Assignee: Hangzhou Zhongmeihuadong Pharmaceutical Co., Ltd., Hangzhou (CN)

( * ) Notice: Subject to any disclaimer, the term of this patent is extended or adjusted under 35 U.S.C. 154(b) by 19 days.

(21) Appl. No.: 18/602,255

(22) Filed: Mar. 12, 2024

(65) Prior Publication Data

US 2024/0325549 A1      Oct. 3, 2024

Related U.S. Application Data

(63) Continuation-in-part of application No. PCT/CN2023/106879, filed on Jul. 12, 2023.

(30) Foreign Application Priority Data

| | | |
|---|---|---|
| Jul. 13, 2022 | (CN) | 202210825092.1 |
| Oct. 17, 2022 | (CN) | 202211266927.0 |
| Jan. 18, 2023 | (CN) | 202310096643.X |

(51) Int. Cl.
| | |
|---|---|
| A61K 47/64 | (2017.01) |
| A61P 3/04 | (2006.01) |
| A61P 3/10 | (2006.01) |
| C07K 14/605 | (2006.01) |

(52) U.S. Cl.
CPC ............... A61K 47/64 (2017.08); A61P 3/04 (2018.01); A61P 3/10 (2018.01); C07K 14/605 (2013.01)

(58) Field of Classification Search
CPC ... A61K 47/64; A61P 3/04; A61P 3/10; C07K 14/605
See application file for complete search history.

(56) References Cited

U.S. PATENT DOCUMENTS

| | | | | |
|---|---|---|---|---|
| 11,084,861 | B2 * | 8/2021 | Abraham | A61P 3/10 |
| 2014/0357552 | A1 * | 12/2014 | Asami | A61P 3/10 |
| | | | | 530/308 |
| 2020/0024322 | A1 * | 1/2020 | Abraham | A61P 3/10 |

FOREIGN PATENT DOCUMENTS

| | | |
|---|---|---|
| CN | 105209485 | 12/2015 |
| CN | 107207576 | 9/2017 |
| CN | 112409460 | 2/2021 |
| CN | 112469731 | 3/2021 |
| CN | 112608377 | 4/2021 |
| CN | 113366014 | 9/2021 |
| WO | 2021093883 | 5/2021 |
| WO | 2021110845 | 6/2021 |
| WO | 2022018185 | 1/2022 |
| WO | 2022018186 | 1/2022 |
| WO | 2022079639 | 4/2022 |

OTHER PUBLICATIONS

Lau et al., J. Med. Chem. 2015, 58, 7370-7380 (Year: 2015).*
Brandt et al., Journal of Internal Medicine. 2018, 284; 581—(Year: 2018).*
Rose et al., Expert Opinion on Drug Discovery, 2019, vol. 14, No. 11, 1151-1159 (Year: 2019).*
Liu et al., Expert Opinion on Therapeutic Patents, 2020, vol. 30, No. 10, 781-794 (Year: 2020).*
Written Opinion for PCT/JP2015/083004, 6 pages, mailed Mar. 1, 2016 (Year: 2016).*
Brandt SJ, Müller TD, DiMarchi RD, Tschöp MH, Stemmer K. Peptide-based multi-agonists: a new paradigm in metabolic pharmacology. Journal of internal medicine. Dec. 2018;284(6):581-602.

* cited by examiner

*Primary Examiner* — Joseph Fischer
(74) *Attorney, Agent, or Firm* — Robin L. Teskin; Baker, Donelson, Bearman, Caldwell & Berkowitz PC

(57) ABSTRACT

The present invention relates to long-acting GLP-1/GIP dual agonist compounds having a dual agonistic effect on glucagon-like peptide-1 (GLP-1) receptor and human glucose-dependent insulinotropic polypeptide (GIP) receptor. The present invention also relates to the use of said compounds in the manufacture of medicaments for treating Type II diabetes mellitus.

2 Claims, 6 Drawing Sheets

Specification includes a Sequence Listing.

1

GLP-1/GIP DUAL AGONIST, PREPARATION METHOD AND USE THEREOF

CROSS-REFERENCE TO RELATED APPLICATIONS

This application is a continuation-in-part application of Int'l Chinese Appl. No. PCT/CN2023/106879, filed Jul. 12, 2023, which claims priority to Int'l Chinese Appl. No. 202310096643.X filed Jan. 18, 2023, Int'l Chinese Appl. No. 202211266927.0 filed Oct. 17, 2022, and Int'l Chinese Appl. No. 202210825092.1 filed Jul. 13, 2022, each and all of which are incorporated herein by reference in their entireties.

SEQUENCE LISTING DISCLOSURE

The contents of the electronic sequence listing (11584980047001.xml; Size: 105,654 bytes; and Date of Creation: Dec. 2, 2024) is herein incorporated by reference in its entirety.

TECHNICAL FIELD

The present invention relates to the field of medicine, and in particular relates to a GLP-1/GIP dual agonist and its use in the manufacture of a medicament for treating diabetes mellitus.

BACKGROUND ART

Type II diabetes mellitus is a kind of chronic metabolic disease clinically characterized by hyperglycemia caused by insulin resistance. Elevated blood glucose can increase the incidence and mortality of other diseases. All the methods commonly used to treat the disease at present, such as doing more exercise, controlling the diet, orally administrating a hypoglycaemic drug and injecting a therapeutic drug can only temporarily maintain the blood glucose balance, and cannot fundamentally treat diabetes mellitus and various complex complications caused by hyperglycemia. Therefore, it is of great clinical importance to extensively explore and develop a therapeutic drug for treating diabetes mellitus involving a novel hypoglycaemic mechanisms with high safety.

Glucagon-like peptide-1 (GLP-1) is a kind of hormone mainly produced by intestinal L cells and belongs to incretin. GLP-1 is an important incretin hormone secreted by intestinal L cells, and its main physiological functions in the body include stimulating the secretion and release of insulin, inhibiting the secretion of glucagon, promoting the proliferation of pancreatic β cells and inhibiting its apoptosis, inhibiting gastric emptying, promoting the generation of satiety and the like. The function of glucose-dependent insulinotropic polypeptide (GIP) is regulating blood glucose by promoting insulin and glucagon, which has also been widely confirmed and applied.

Compounds with GLP-1/GIP dual agonist activity have been disclosed in WO2013164483A1, WO2014192284A1 and WO2016111971A1.

Modifying a polypeptide with a fatty acid, through which the fatty acid chain is physically bond to an albumin subdomain/motif, can, for example, increase the half-life, thereby improving the pharmacokinetics of the peptide. Although the half-life of a peptide may be improved by use of a fatty acid, the specific prolonging effect and some side effects are still technical problems that need to be solved.

A series of adverse effects are produced by GLP-1. For example, there are concerns about the effects of GLP-1 receptor agonists on pancreatic and thyroid tissues, since animal studies and drug database analysis have shown that these drugs are associated with pancreatitis, pancreatic cancer and thyroid cancer. According to other cases reported, the use of GLP-1 (mainly Exenatide) is associated with the occurrence of acute kidney injury, mainly due to haemodynamic disturbances caused by nausea, vomiting and diarrhoea. The most common symptom associated with the use of GLP-1 receptor agonists is gastrointestinal symptoms, mainly including nausea. Other common adverse reactions include injection site reactions, headache and nasopharyngitis and the like. (Filippatos T D, Panagiotopoulou T V, Elisaf M S. Adverse Effects of GLP-1 Receptor Agonists. Rev Diabet Stud. 2014 Fall-Winter; 11(3-4): 202-30. doi: 10.1900/RDS.2014.11.202. Epub 2015 Feb. 10. PMID: 26177483; PMCID: PMC5397288.)

About the side effects of Tirzepatide (Mathiesen D S, Bagger J I, Bergmann N C, Lund A, Christensen M B, Vilsbøll T, Knop F K. The Effects of Dual GLP-1/GIP Receptor Agonism on Glucagon Secretion-A Review. Int J Mol Sci. 2019 Aug. 22; 20(17): 4092. doi: 10.3390/ijms20174092. PMID: 31443356; PMCID: PMC6747202.): at the highest dose, the number of adverse events caused by Tirzepatide exceeds that caused by Dulaglutide, especially gastrointestinal tract adverse events (66.0% for the subjects taken 15 mg Tirzepatide versus 42.6% for the subjects taken 1.5 mg Dulaglutide), and the total number of hypoglycemic episodes caused by Tirzepatide also exceeds that caused by Dulaglutide (7.5% for the subjects taken 15 mg Tirzepatide versus 3.7% for the subjects taken Dulaglutide) (Frias J. P., Nauck M. A., Van J., Kutner M. E., Cui X., Benson C., Urva S., Gimeno R. E., Milicevic Z., Robins D., et al. Efficacy and safety of LY3298176, a novel dual GIP and GLP-1 receptor agonist, in subjects with type 2 diabetes mellitus: a randomised, placebo-controlled and active comparator-controlled phase 2 trial. Lancet. 2018; 392:2180-2193. doi: 10.1016/S0140-6736(18) 32260-8). In order to avoid this problem, a titration strategy to reduce adverse events of Tirzepatide has been reported (Frias J. P., Nauck M. A., Van J., Benson C., Bray R., Milicevic Z., Haupt A., Robins D. A. 993-P: A 12-week, randomized, placebo-controlled study assessing the efficacy and safety of three dose-escalation algorithms of Tirzepatide, a novel dual GIP and GLP-1 receptor agonist, in subjects with type 2 diabetes mellitus. Diabetes mellitus. 2019; 68:993. doi: 10.2337/db19-993-P). Moreover, as compared with the previously reported studies, the three-step dose escalation regimen for delivering 15 mg Tirzepatide seems ineffective in reducing the overall incidence of gastrointestinal side effects (Frias J. P., Nauck M. A., Van J., Kutner M. E., Cui X., Benson C., Urva S., Gimeno R. E., Milicevic Z., Robins D., et al. Efficacy and safety of LY3298176, a novel dual GIP and GLP-1 receptor agonist, in subjects with type 2 diabetes mellitus: a randomised, placebo-controlled and active comparator-controlled phase 2 trial. Lancet. 2018; 392:2180-2193. doi: 10.1016/S0140-6736(18)32260-8). In the subjects being administrated 15 mg Tirzepatide, the incidence of hypoglycemic episodes also increased to about 16%. Although the treatment with Tirzepatide was still associated with desired weight loss (about 5.6 kg after 12 weeks), the high incidence of gastrointestinal side effects did raise an uncertainty about the clinical potential of Tirzepatide. In addition, the titration strategy given in the commercial product instruction for Tirzepatide lasts for a long time. The initial dosage is 2.5 mg, and the dosage is increased to 5 mg after 4 weeks. If the dosage needs to be increased to control blood glucose, the current dosage should be maintained for 4 weeks before increasing a further 2.5 mg, which is quite inconvenient.

At present, there is still a need in medicine to provide new compounds, which are dual agonists of GIP and GLP-1 receptors, and have the possibility of administrating once a week, which offers a safer, more effective and more convenient option.

SUMMARY OF INVENTION

An object of the present invention is to provide some long-acting GLP-1/GIP dual agonist compounds. Another object of the present invention is to provide a method for treating or preventing a disease in a subject, including a human and an animal. The compounds of the present invention exhibit excellent GIPR/GLP-1R dual agonistic activity in multiple-species of mammals, including but not limited to primates (e.g. humans) and pets.

Compared with GIP/GLP-1 dual agonist compounds in the art, the compounds according to the present invention have a long half-life and/or a longer duration of action. The compounds according to the present invention have a stronger hypoglycemic effect and more significant weight loss effect. The compounds according to the present invention have less side effects, including but not limited to gastrointestinal reactions and heart safety risks and the like. The compounds according to the present invention could adopt shorter titration strategies. The compounds according to the present invention have a wider safety window. In addition, the compounds according to the present invention have a protective effect on the liver. As a part of the present invention, the applicant has found that the selections in terms of the length, composition and bonding position of the fatty acid chains, and the linker between the peptide and the fatty acid chain, have an unexpected effect on prolonging the half-life of the polypeptide.

An embodiment of the present invention provides a compound of Formula (AI) and a pharmaceutically acceptable salt thereof:

Formula (AI)

(SEQ ID NO: 13)

Y-$X_1$-E-G-T-$X_2$-T-S-D-Y-A11-A12-A13-L-D-K-A17-A-Q-

A20-E-F-V-K-W-L-L-K-A29-G-P-S-S-G-A-P-P-S-K;

wherein $X_1$ is Aib; $X_2$ is αMePhe;

A11 is Aib or Ala;

A12 is Ala, Ile, Lys, Phe or Pya(4);

A13 is Aib, Cha, Leu, αMePhe or αMeTyr;

A17 is Gln or Ile;

A20 is Ala or Ser;

A29 is Gln or Gly;

1, 2, 3 or 4 Ks, which are selected from the group consisting of K at position 16, K at position 24, K at position 28 and K at position 40, are chemically modified through conjugation to the ε-aminos of the K side-chains with ([2-(2-amino-ethoxy)-ethoxy]-acetyl)$_a$-(γ-Glu)$_b$-CO—(CH$_2$)$_c$—Z, wherein each a is independently an integer from 0 to 5, each b is independently an integer from 0 to 5, and each c is independently an integer from 10 to 24, wherein Z is independently selected from the group consisting of —CH$_3$, carboxylic acids or carboxylic acid bioisosteres, phosphonates or sulfonates, and the C-terminal amino acid is amidated as a C-terminal primary amide.

In a further embodiment, the present invention provides a compound of Formula (AI) or a pharmaceutically acceptable salt thereof, wherein, $X_1$ is Aib; $X_2$ is αMePhe;

A11 is Aib or Ala;

A12 is Ala, Ile, Lys, Phe or Pya (4);

A13 is Aib, Cha, Leu, αMePhe or αMeTyr;

A17 is Gln or Ile;

A20 is Ala or Ser;

A29 is Gln or Gly;

1, 2, 3 or 4 Ks, which are selected from the group consisting of K at position 16, K at position 24, K at position 28 and K at position 40, are chemically modified through conjugation to the ε-aminos of the K side-chains with ([2-(2-amino-ethoxy)-ethoxy]-acetyl)$_a$-(γ-Glu)$_b$-CO—(CH$_2$)$_c$—Z, wherein a is independently selected from an integer of 1, 2, 3, 4 or 5, b is independently selected from an integer of 1, 2, 3, 4 or 5, and c is independently selected from an integer of 12 to 22; wherein Z is independently selected from the group consisting of —CH$_3$, carboxylic acids or carboxylic acid bioisosteres, phosphonates or sulfonates; and the C-terminal amino acid is amidated as a C-terminal primary amide, in addition, the present invention further provides compounds wherein c is independently selected from 14, 16, 18 or 20.

The peptide of the above Formula (AI) or a pharmaceutically acceptable salt thereof, wherein A11 is Aib; and/or the peptide of the above Formula (AI) or a pharmaceutically acceptable salt thereof, wherein A12 is Ile; and/or the peptide of the above Formula (AI) or a pharmaceutically acceptable salt thereof, wherein A13 is Aib; and/or the peptide of the above Formula (AI) or a pharmaceutically acceptable salt thereof, wherein A17 is Gln; and/or the peptide of the above Formula (AI) or a pharmaceutically acceptable salt thereof, wherein A20 is Ala; and/or the peptide of the above Formula (AI), or a pharmaceutically acceptable salt thereof, wherein A29 is Gly.

An embodiment of the present invention provides a compound of Formula (I) and a pharmaceutically acceptable salt thereof:

Formula (I)

(SEQ ID NO: 12)

Y-$X_1$-E-G-T-$X_2$-T-S-D-Y-$X_3$-I-$X_4$-L-D-K-Q-A-Q-A-E-F-V-

K-W-L-L-K-G-G-P-S-S-G-A-P-P-S-K;

wherein $X_1$ is Aib; $X_2$ is αMePhe; $X_3$ is Aib; $X_4$ is Aib; 1, 2, 3 or 4 Ks, which are selected from the group consisting of K at position 16, K at position 24, K at position 28 and K at position 40, are chemically modified through conjugation to the ε-aminos of the K side-chains with ([2-(2-amino-ethoxy)-ethoxy]-acetyl)$_a$-(γ-Glu)$_b$-CO—(CH$_2$)$_c$—Z, wherein each a is independently an integer from 0 to 5, each b is independently an integer from 0 to 5, and each c is independently an integer from 10 to 24, wherein Z is independently selected from the group consisting of —CH$_3$, carboxylic acids or carboxylic acid bioisosteres, phosphonates or sulfonates; and the C-terminal amino acid is amidated as a C-terminal primary amide.

In some embodiments, the present invention provides a compound of Formula (I) or a pharmaceutically acceptable salt thereof, wherein 1 K selected from the group consisting of K at position 16, K at position 24, K at position 28 and K at position 40 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—Z. For example, K at position 16 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—Z. For example, K at position 24 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—Z. For example, K at position 28 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—Z. For example, K at position 40 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—Z.

In some embodiments, the present invention provides a compound of Formula (I) or a pharmaceutically acceptable salt thereof, wherein 2 Ks selected from the group consisting of K at position 16, K at position 24, K at position 28 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 16 and K at position 24 are chemically modified with two modifying chains through conjugation to the ¿-aminos of the K side-chains with ([2-(2-amino-ethoxy)-ethoxy]-acetyl)$_a$-(γ-Glu)$_b$-CO—(CH$_2$)$_c$—Z. For example, K at position 16 and K at position 28 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 16 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 24 and K at position 28 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 24 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 28 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z.

In some embodiments, the present invention provides a compound of Formula (I) or a pharmaceutically acceptable salt thereof, wherein 3 Ks selected from the group consisting of K at position 16, K at position 24, K at position 28 and K at position 40 are chemically modified with three modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 16, K at position 24 and K at position 28 are chemically modified with three modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 16, K at position 24 and K at position 40 are chemically modified with three modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 16, K at position 28 and K at position 40 are chemically modified with three modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 24, K at position 28 and K at position 40 are chemically modified with three modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z.

In some embodiments, the present invention provides a compound of Formula (I) or a pharmaceutically acceptable salt thereof, wherein 4 Ks selected from the group consisting of K at position 16, K at position 24, K at position 28 and K at position 40 are chemically modified with four modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z. For example, K at position 16, K at position 24, K at position 28 and K at position 40 are chemically modified with four modifying chains through conjugation to the ε-aminos of the K side-chains with ([2-(2-amino-ethoxy)-ethoxy]-acetyl)$_a$-(γ-Glu)$_b$-CO—(CH$_2$)$_c$—Z.

In some embodiments, the present invention provides a compound of Formula (I), or a pharmaceutically acceptable salt thereof, wherein Z is independently selected from the group consisting of —CH$_3$, carboxylic acids or carboxylic acid bioisosteres, phosphonates or sulfonates, for example, but not limited to the instances where said Z may comprise a carboxylic acid (—CO$_2$H) or carboxylic acid bioisosteres (for example a phosphonic acid (—P(O)(OH)$_2$) or a sulfonic acid (—SO$_2$OH) group, preferably —CO$_2$H.

As for carboxylic acid bioisosteres, suitable carboxylic acid bioisosteres are known in the art. Preferably, the bioisosteres have protons with a pK$_a$ similar to that of the corresponding carboxylic acids. Examples of suitable bioisosteres may include, but are not limited to, tetrazoles, acylsulfonamides, acylhydroxylamines and squaric acid derivatives as shown below:

R is Me or CF$_3$.

In some embodiments, the present invention provides a compound of Formula (I) or a pharmaceutically acceptable salt thereof, wherein a is independently selected from an integer of 1, 2, 3, 4 or 5, preferably 1, 2 or 3, b is independently selected from an integer of 1, 2, 3, 4 or 5, preferably 1, 2 or 3, and c is independently selected from an integer of 12 to 22; in addition, the present invention further provides compounds wherein c is 14, 16, 18 or 20.

An embodiment of the present invention provides a compound of Formula (I) and a pharmaceutically acceptable salt thereof:

Formula (I)

(SEQ ID NO: 14)

Y-X$_1$-E-G-T-X$_2$-T-S-D-Y-X$_3$-I-X$_4$-L-D-K-Q-A-Q-A-E-F-V-

K-W-L-L-K-G-G-P-S-S-G-A-P-P-P-S-K;

wherein X$_1$ is Aib; X$_2$ is αMePhe; X$_3$ is Aib; X$_4$ is Aib; 1 K or 2 Ks selected from the group consisting of K at position 16, K at position 24, K at position 28 and K at position 40 are chemically modified through conjugation to the ε-aminos of the K side-chains with ([2-(2-amino-ethoxy)-ethoxy]-acetyl)$_a$-(γ-Glu)$_b$-CO—(CH$_2$)$_c$—Z, wherein Z is independently selected from the group consisting of —CH$_3$, carboxylic acids or carboxylic acid bioisosteres, phosphonates or sulfonates, preferably —CO$_2$H, wherein each a is independently an integer from 0 to 5, each b is independently an integer from 0 to 5, and each c is independently an integer from 10 to 24, and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; 1 K or 2 Ks selected from the group consisting of K at position 16, K at position 24, K at position 28 and K at position 40 are chemically modified through conjugation to the ε-aminos of the K side-chains with ([2-(2-amino-ethoxy)-ethoxy]-acetyl)$_a$-(γ-Glu)$_b$-CO—(CH$_2$)$_c$—Z, wherein Z is independently selected from the group consisting of —CH$_3$, carboxylic acids or carboxylic acid bioisosteres, phosphonates or sulfonates, preferably —CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

An embodiment of the present invention provides a compound of Formula (I) and a pharmaceutically acceptable salt thereof:

Formula (I)

(SEQ ID NO: 15)

Y-X$_1$-E-G-T-X$_2$-T-S-D-Y-X$_3$-I-X$_4$-L-D-K-Q-A-Q-A-E-F-V-

K-W-L-L-K-G-G-P-S-S-G-A-P-P-P-S-K;

wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 24; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein each a is independently selected from an integer of 2 and 3, each b is independently selected 1 and 3, each c is independently selected from an integer of 16, 18 and 20, and Z is independently selected from carboxylic acids.

A further embodiment of the present invention provides a compound of Formula (I) and a pharmaceutically acceptable salt thereof:

Formula (I)

(SEQ ID NO: 16)

Y-X$_1$-E-G-T-X$_2$-T-S-D-Y-X$_3$-I-X$_4$-L-D-K-Q-A-Q-A-E-F-V-

K-W-L-L-K-G-G-P-S-S-G-A-P-P-P-S-K;

wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 24; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein each a is independently selected from an integer of 2 and 3, each b is independently selected from an integer of 1 and 3, each c is independently selected from an integer of 16, 18 and 20, and Z is independently selected from carboxylic acids.

A further embodiment of the present invention provides a compound of Formula (I) and a pharmaceutically acceptable salt thereof, Formula (I)

(SEQ ID NO: 17)

Y-X$_1$-E-G-T-X$_2$-T-S-D-Y-X$_3$-I-X$_4$-L-D-K-Q-

A-Q-A-E-F-V-K-W-L-L-K-G-G-P-S-S-G-A-P-

P-P-S-K;

wherein X$_1$ is Aib; X$_2$ is αMePhe; X$_3$ is Aib; X$_4$ is Aib; K at position 16 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 24; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 16 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

A further embodiment of the present invention provides a compound of Formula (I) and a pharmaceutically acceptable salt thereof, Formula (I)

(SEQ ID NO: 18)

Y-X$_1$-E-G-T-X$_2$-T-S-D-Y-X$_3$-I-X$_4$-L-D-K-Q-

A-Q-A-E-F-V-K-W-L-L-K-G-G-P-S-S-G-A-P-

P-P-S-K;

wherein X$_1$ is Aib; X$_2$ is αMePhe; X$_3$ is Aib; X$_4$ is Aib; K at position 40 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 24; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 40 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

A further embodiment of the present invention provides a compound of Formula (I) and a pharmaceutically acceptable salt thereof, Formula (I)

(SEQ ID NO: 19)

Y-X$_1$-E-G-T-X$_2$-T-S-D-Y-X$_3$-I-X$_4$-L-D-K-Q-

A-Q-A-E-F-V-K-W-L-L-K-G-G-P-S-S-G-A-P-

P-P-S-K;

wherein X$_1$ is Aib; X$_2$ is αMePhe; X$_3$ is Aib; X$_4$ is Aib; K at position 24 and K at position 28 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 22; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 24 and K at position 28 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

A further embodiment of the present invention provides a compound of Formula (I) and a pharmaceutically acceptable salt thereof, Formula (I)

(SEQ ID NO: 20)

Y-X$_1$-E-G-T-X$_2$-T-S-D-Y-X$_3$-I-X$_4$-L-D-K-Q-

A-Q-A-E-F-V-K-W-L-L-K-G-G-P-S-S-G-A-P-

P-P-S-K;

wherein X$_1$ is Aib; X$_2$ is αMePhe; X$_3$ is Aib; X$_4$ is Aib; K at position 16 and K at position 24 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 22; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 16 and K at position 24 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

A further embodiment of the present invention provides a compound of Formula (I) and a pharmaceutically acceptable salt thereof, Formula (I)

(SEQ ID NO: 21)

Y-X$_1$-E-G-T-X$_2$-T-S-D-Y-X$_3$-I-X$_4$-L-D-K-Q-

A-Q-A-E-F-V-K-W-L-L-K-G-G-P-S-S-G-A-P-

P-P-S-K;

wherein X$_1$ is Aib; X$_2$ is αMePhe; X$_3$ is Aib; X$_4$ is Aib; K at position 16 and K at position 28 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 22; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 16 and K at position 28 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

A further embodiment of the present invention provides a compound of Formula (I) and a pharmaceutically acceptable salt thereof, Formula (I)

(SEQ ID NO: 22)

Y-X$_1$-E-G-T-X$_2$-T-S-D-Y-X$_3$-I-X$_4$-L-D-K-Q-

A-Q-A-E-F-V-K-W-L-L-K-G-G-P-S-S-G-A-P-

P-P-S-K;

wherein X$_1$ is Aib; X$_2$ is αMePhe; X$_3$ is Aib; X$_4$ is Aib; K at position 16 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 22; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 16 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

A further embodiment of the present invention provides a compound of Formula (I) and a pharmaceutically acceptable salt thereof, Formula (I)

(SEQ ID NO: 23)

Y-X$_1$-E-G-T-X$_2$-T-S-D-Y-X$_3$-I-X$_4$-L-D-K-Q-

A-Q-A-E-F-V-K-W-L-L-K-G-G-P-S-S-G-A-P-

P-P-S-K;

wherein X$_1$ is Aib; X$_2$ is αMePhe; X$_3$ is Aib; X$_4$ is Aib; K at position 24 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 22; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 24 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

A further embodiment of the present invention provides a compound of Formula (I) and a pharmaceutically acceptable salt thereof, Formula (I)

(SEQ ID NO: 24)

Y-X$_1$-E-G-T-X$_2$-T-S-D-Y-X$_3$-I-X$_4$-L-D-K-Q-

A-Q-A-E-F-V-K-W-L-L-K-G-G-P-S-S-G-A-P-

P-P-S-K;

wherein X$_1$ is Aib; X$_2$ is αMePhe; X$_3$ is Aib; X$_4$ is Aib; K at position 28 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, and c is independently selected from an integer of 10 to 22; and the C-terminal amino acid is amidated as a C-terminal primary amide.

In a further embodiment, the present invention provides a compound of Formula (I) or a pharmaceutically acceptable salt thereof, wherein X$_1$ is Aib; X$_2$ is αMePhe; X$_3$ is Aib; X$_4$ is Aib; K at position 28 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20.

In all the above-mentioned embodiments, each a is independently an integer of 1 to 3, each b is independently an integer of 1 to 3, and each c is independently an integer of 12 to 22. In addition, the present invention further provides compounds wherein c is 14, 16, 18 or 20. Among all the embodiments described above, preferred are the embodiments in which K at position 24 or K at position 28 is modified.

In an embodiment, the present invention provides a compound of the following Formula or a pharmaceutically acceptable salt thereof;

(SEQ ID NO: 2)
Y-$X_1$-E-G-T-$X_2$-T-S-D-Y-$X_3$-I-$X_4$-L-D-K-Q-

A-Q-A-E-F-V-K-W-L-L-K-G-G-P-S-S-G-A-P-

P-P-S-K;

wherein $X_1$ is Aib; $X_2$ is $\alpha$MePhe; $X_3$ is Aib; $X_4$ is Aib; K at position 24 is chemically modified through conjugation to the $\varepsilon$-amino of the K side-chain with ([2-(2-amino-ethoxy)-ethoxy]-acetyl)$_2$-($\gamma$-Glu)$_1$-CO—(CH$_2$)$_{16}$—CO$_2$H; and the C-terminal amino acid is amidated as a C-terminal primary amide.

In an embodiment, the present invention provides a compound of the following Formula or a pharmaceutically acceptable salt thereof;

(SEQ ID NO: 4)
Y-$X_1$-E-G-T-$X_2$-T-S-D-Y-$X_3$-I-$X_4$-L-D-K-Q-

A-Q-A-E-F-V-K-W-L-L-K-G-G-P-S-S-G-A-P-

P-P-S-K;

wherein $X_1$ is Aib; $X_2$ is $\alpha$MePhe; $X_3$ is Aib; $X_4$ is Aib; K at position 24 is chemically modified through conjugation to the $\varepsilon$-amino of the K side-chain with ([2-(2-amino-ethoxy)-ethoxy]-acetyl)$_2$-($\gamma$-Glu)$_1$-CO—(CH$_2$)$_{18}$—CO$_2$H; and the C-terminal amino acid is amidated as a C-terminal primary amide.

In an embodiment, the present invention provides a compound of the following Formula or a pharmaceutically acceptable salt thereof;

(SEQ ID NO: 5)
Y-$X_1$-E-G-T-$X_2$-T-S-D-Y-$X_3$-I-$X_4$-L-D-K-Q-

A-Q-A-E-F-V-K-W-L-L-K-G-G-P-S-S-G-A-P-

P-P-S-K;

wherein $X_1$ is Aib; $X_2$ is $\alpha$MePhe; $X_3$ is Aib; $X_4$ is Aib; K at position 24 is chemically modified through conjugation to the $\varepsilon$-amino of the K side-chain with ([2-(2-amino-ethoxy)-ethoxy]-acetyl)$_2$-($\gamma$-Glu)$_1$-CO—(CH$_2$)$_{20}$—CO$_2$H; and the C-terminal amino acid is amidated as a C-terminal primary amide.

In an embodiment, the present invention provides a compound of the following Formula or a pharmaceutically acceptable salt thereof;

(SEQ ID NO: 6)
Y-$X_1$-E-G-T-$X_2$-T-S-D-Y-$X_3$-I-$X_4$-L-D-K-Q-

A-Q-A-E-F-V-K-W-L-L-K-G-G-P-S-S-G-A-P-

P-P-S-K;

wherein $X_1$ is Aib; $X_2$ is $\alpha$MePhe; $X_3$ is Aib; $X_4$ is Aib; K at position 24 is chemically modified through conjugation to the $\varepsilon$-amino of the K side-chain with ([2-(2-amino-ethoxy)- ethoxy]-acetyl)$_2$-($\gamma$-Glu)$_3$-CO—(CH$_2$)$_{16}$—CO$_2$H; and the C-terminal amino acid is amidated as a C-terminal primary amide.

In an embodiment, the present invention provides a compound of the following Formula or a pharmaceutically acceptable salt thereof;

(SEQ ID NO: 7)
Y-$X_1$-E-G-T-$X_2$-T-S-D-Y-$X_3$-I-$X_4$-L-D-K-Q-

A-Q-A-E-F-V-K-W-L-L-K-G-G-P-S-S-G-A-P-

P-P-S-K;

wherein $X_1$ is Aib; $X_2$ is $\alpha$MePhe; $X_3$ is Aib; $X_4$ is Aib; K at position 24 is chemically modified through conjugation to the $\varepsilon$-amino of the K side-chain with ([2-(2-amino-ethoxy)-ethoxy]-acetyl) 3-($\gamma$-Glu)$_1$-CO—(CH$_2$)$_{20}$—CO$_2$H; and the C-terminal amino acid is amidated as a C-terminal primary amide.

In an embodiment, the present invention provides a compound of the following Formula or a pharmaceutically acceptable salt thereof;

(SEQ ID NO: 3)
Y-$X_1$-E-G-T-$X_2$-T-S-D-Y-$X_3$-I-$X_4$-L-D-K-Q-

A-Q-A-E-F-V-K-W-L-L-K-G-G-P-S-S-G-A-P-

P-P-S-K;

wherein $X_1$ is Aib; $X_2$ is $\alpha$MePhe; $X_3$ is Aib; $X_4$ is Aib; K at position 28 is chemically modified through conjugation to the $\varepsilon$-amino of the K side-chain with ([2-(2-amino-ethoxy)-ethoxy]-acetyl)$_2$-($\gamma$-Glu)$_1$-CO—(CH$_2$)$_{16}$—CO$_2$H; and the C-terminal amino acid is amidated as a C-terminal primary amide.

In an embodiment, the present invention provides a compound of the following Formula or a pharmaceutically acceptable salt thereof;

(SEQ ID NO: 8)
Y-$X_1$-E-G-T-$X_2$-T-S-D-Y-$X_3$-I-$X_4$-L-D-K-Q-

A-Q-A-E-F-V-K-W-L-L-K-G-G-P-S-S-G-A-P-

P-P-S-K;

wherein $X_1$ is Aib; $X_2$ is $\alpha$MePhe; $X_3$ is Aib; $X_4$ is Aib; K at position 28 is chemically modified through conjugation to the $\varepsilon$-amino of the K side-chain with ([2-(2-amino-ethoxy)-ethoxy]-acetyl)$_2$-($\gamma$-Glu)$_1$-CO—(CH$_2$)$_{20}$—CO$_2$H; and the C-terminal amino acid is amidated as a C-terminal primary amide.

In an embodiment, the present invention provides a compound of the following Formula or a pharmaceutically acceptable salt thereof;

(SEQ ID NO: 9)
Y-$X_1$-E-G-T-$X_2$-T-S-D-Y-$X_3$-I-$X_4$-L-D-K-Q-A-Q-A-E-

F-V-K-W-L-L-K-G-G-P-S-S-G-A-P-P-P-S-K;

wherein $X_1$ is Aib; $X_2$ is $\alpha$MePhe; $X_3$ is Aib; $X_4$ is Aib; K at position 28 is chemically modified through conjugation to the $\varepsilon$-amino of the K side-chain with ([2-(2-amino-ethoxy)-ethoxy]-acetyl)$_2$-($\gamma$-Glu)$_3$-CO—(CH$_2$)$_{16}$—CO$_2$H; and the C-terminal amino acid is amidated as a C-terminal primary amide.

In an embodiment, the present invention provides a compound of the following Formula or a pharmaceutically acceptable salt thereof;

(SEQ ID NO: 10)

Y-X$_1$-E-G-T-X$_2$-T-S-D-Y-X$_3$-I-X$_4$-L-D-K-Q-A-Q-A-E-

F-V-K-W-L-L-K-G-G-P-S-S-G-A-P-P-P-S-K;

wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl) 3-(γ-Glu)$_1$-CO—(CH$_2$)$_{16}$—CO$_2$H; and the C-terminal amino acid is amidated as a C-terminal primary amide.

In an embodiment, the present invention provides a compound of the following Formula or a pharmaceutically acceptable salt thereof;

(SEQ ID NO: 11)

Y-X$_1$-E-G-T-X$_2$-T-S-D-Y-X$_3$-I-X$_4$-L-D-K-Q-A-Q-A-E-

F-V-K-W-L-L-K-G-G-P-S-S-G-A-P-P-P-S-K;

wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl) 3-(γ-Glu)$_1$-CO—(CH$_2$)$_{20}$—CO$_2$H; and the C-terminal amino acid is amidated as a C-terminal primary amide.

Another object of the present invention is to provide a method for treating or preventing a disease in an animal, especially in a mammal, comprising administering to a subject in need thereof, an effective amount of the compound of the present invention. The compounds and pharmaceutically acceptable salts thereof described in any of the above embodiments apply to this object of the present invention.

The present invention further provides a method for increasing the action duration of the GLP-1/GIP dual agonist in a subject, characterized by using the acylated GLP-1/GIP dual agonist provided by the present invention as described above.

In an embodiment, the present invention provides a composition comprising the compound according to the present invention and a pharmaceutically acceptable carrier, diluent or excipient.

An embodiment provides a use of the compound according to any one of the above-mentioned embodiments in the manufacture of a medicament for treating or preventing a disease selected from hyperglycemia, impaired glucose tolerance, Type I diabetes mellitus, Type II diabetes mellitus, obesity, hypertension, Syndrome X, dyslipidemia, cognitive impairment, atherosclerosis, myocardial infarction, coronary heart disease and other cardiovascular diseases, stroke, inflammatory bowel syndrome, dyspepsia and gastric ulcers.

An embodiment provides a use of the compound according to any one of the above-mentioned embodiments in the manufacture of a medicament for delaying or preventing the disease development of Type II diabetes mellitus.

An embodiment provides a use of the compound according to any one of the above-mentioned embodiments in the manufacture of a medicament for reducing food intake, reducing β-cell apoptosis, increasing β-cell function and β-cell volume, and/or restoring glucose sensitivity of β-cell.

In an embodiment, the present invention provides a method for treating Type II diabetes mellitus, comprising administering to a subject in need thereof, an effective amount of the compound according to the present invention.

In an embodiment, the present invention provides a method of improving blood glucose control in a subject suffering from Type II diabetes mellitus, comprising administering to a subject in need thereof, an effective amount of the compound according to the present invention as an adjunct to diet and exercise.

In an embodiment, the present invention provides a method for chronic weight management in a subject with an initial body mass index≥27 and Type 2 diabetes, comprising administering to a subject in need thereof, an effective amount of the compound according to the present invention as an adjunct to a reduced-calorie diet and increased physical activity.

In an embodiment, the present invention provides a method for chronic weight management in an overweight or obese subject, comprising administering to a subject in need thereof, an effective amount of the compound according to the present invention as an adjunct to a reduced-calorie diet and increased physical activity.

In an embodiment, the present invention provides a method for treating metabolic syndrome, comprising administering to a subject in need thereof, an effective amount of the compound according to the present invention. In a further embodiment, the present invention provides a method for treating dyslipidaemia, obesity and/or hepatic steatosis associated with insulin resistance and diabetes mellitus, comprising administering to a subject in need thereof, an effective amount of the compound according to the present invention. Additionally, the present invention further provides a method for treating frailty or increasing bone strength, comprising administering to a subject in need thereof, an effective amount of the compound according to the present invention.

In another embodiment, the present invention provides a method for treating osteopenia and/or bone/joint diseases, such as for treating knee osteoarthritis, hip osteoarthritis, spondylitis deformans, and osphyalgia, comprising administering to a subject in need thereof, an effective amount of the compound or a pharmaceutically acceptable salt thereof according to the present invention.

In an embodiment, the present invention provides a compound of the present invention as an adjunct to diet and exercise for blood glucose control in a Type II diabetic subject. In an embodiment, the present invention provides a compound of the present invention for chronic weight management as an adjunct to a reduced-calorie diet and increased physical activity in a subject with an initial body mass index≥27 and Type II diabetes. In an embodiment, the present invention provides a compound according to the present invention for chronic weight management as an adjunct to a reduced-calorie diet and increased physical activity in an overweight or obese subject.

Due to the above-mentioned activities of the compounds according to the present invention towards GLP-1 receptor and GIP receptor, the compound according to the present invention can be used as a medicament for treating or preventing various diseases, such as obesity. The compound according to the present invention can be used as a medicament for preventing or treating a disease, such as, symptomatic obesity, obesity based on simple obesity, obesity-related conditions or diseases, eating disorders, diabetes mellitus (for example, Type I diabetes mellitus, Type II diabetes mellitus, gestational diabetes mellitus, obesity diabetes mellitus), hyperlipidemia (e.g., hypertriglyceridemia, hypercholesterolemia, hyper-LDL-cholesterolemia, low HDL-cholesterolemia, postprandial hyperlipidemia), hypertension, heart failure, complications of diabetes mellitus [for example, neuropathy, nephropathy, retinopathy, diabetic cardiomyopathy, cataract, macroangiopathy, osteopenia, hyperosmolar diabetic coma], infectious disease (for example, respiratory tract infection, urinary tract infection, gastrointestinal infection, superficial soft tissue infection, lower extremity infection), diabetic gangrene, xerostomia, hypacusia, cerebrovascular disorder, peripheral blood circulation disorder, metabolic syndrome (with three or more conditions selected from the group consisting of hypertriglyceridemia (TG), low HDL-cholesterolemia (HDL-C), hypertension, abdominal obesity, and impaired glucose tolerance), sarcopenia, and the like.

Examples of symptomatic obesity include: endocrine obesity (e.g., Cushing's syndrome, hypothyroidism, insulinoma, obese Type II diabetes mellitus, pseudohypoparathyroidism, hypogonadism), central obesity (e.g. hypothalamic obesity, frontal lobe syndrome, Klein-Lewis syndrome), genetic obesity (e.g., Prader-Willi syndrome, Laurence-Moon-Biedl's syndrome), drug-induced obesity (e.g., steroids, phenothiazines, insulin, sulfonylurea (SU) drugs, β-blocker induced obesity), and the like.

Examples of conditions or diseases associated with obesity include: glucose tolerance disorder, diabetes mellitus (especially Type II diabetes mellitus, obesity diabetes mellitus), abnormal lipid metabolism (synonymous with hyperlipidemia above), hypertension, heart failure, hyperuricemia, fatty liver (including non-alcoholic hepatitis), coronary heart disease (myocardial infarction, angina pectoris), cerebral infarction (cerebral thrombosis, transient ischemic attack), bone/joint disease (knee osteoarthritis, hip osteoarthritis, deformed spondylitis, low back pain), sleep apnea syndrome/Pickwick syndrome, menstrual disorders (abnormal menstrual cycle, abnormal menstruation and cycle, amenorrhea, abnormal menstrual symptoms), metabolic syndrome, and the like.

The compounds provided by the present invention have GLP-1/GIP dual agonist activity, a long half-life, and show a longer duration of drug effect.

The compounds according to the present invention can react with any of a variety of inorganic and organic acids to form pharmaceutically acceptable acid addition salts. The pharmaceutically acceptable salts and the methods commonly used for their preparation are well-known in the art.

In an embodiment, the compounds according to the present invention is administered in the form of preparations. In addition to the compounds according to the present invention, the preparations optionally further comprise one or more of pharmaceutically acceptable carriers, diluents, fillers, disintegrants, binders, lubricants, surfactants, hydrophobic vehicles, water-soluble vehicles, emulsifiers, buffers, wetting agents, moisturizers, solubilizers and preservatives, etc. The preparations described herein may be in the form of solutions, suspensions, hydrogel, depot, implant, microneedle, emulsions, tablets, pills, granules, capsules, liquid-containing capsules, powders, sustained release preparations, suppositories, aerosols, sprays, or any other forms suitable for use. Buffer solution, saline solutions, aqueous glucose solutions, and aqueous glycerol solutions can be used as liquid carriers, especially for injectable solutions.

The compounds according to the present invention may be administered in any conventional manner by any route in which they are active, for example, they may be administered systemically or topically. For example, administration may be performed by inhalation, by depot injection, or by implantation. For example, administration may be, but are not limited to, parenteral, subcutaneous, intravenous, intramuscular, intraperitoneal, transdermal, oral administration. The compounds according to the present invention may be used with at least one other therapeutic agent for combination therapy. In some embodiments, the compounds according to the present invention may be administered in combination with additional diabetes drugs, anti-obesity drugs, blood pressure drugs, and/or cholesterol drugs. The compounds according to the present invention may act additively or synergistically with other therapeutic agent(s). The other therapeutic agent(s) and the compounds according to the present invention may be comprised in the same composition, or may be separately comprised in different compositions. The compositions containing a compound according to the invention and another therapeutic agent(s) can be administered simultaneously or sequentially. In another embodiment, the composition comprising a compound of the invention is administered before or after the other therapeutic agent(s).

In some embodiments, the compounds according to the present invention are used to treat or prevent Type II diabetes mellitus, overweight and/or obesity in humans.

In some embodiments, the compounds according to the present invention are used to treat or prevent Type II diabetes mellitus, overweight and/or obesity in cats or dogs.

In some embodiments, the compounds according to the present invention are administered in the form of solutions or suspensions.

In some embodiments, the compounds according to the present invention are administered by subcutaneous injection.

In some embodiments, the compounds according to the present invention are administered in cats or dogs at a dose of 0.003 to 0.6 mg/kg, calculated based on body surface area.

In some embodiments, the compounds according to the present invention are administered in cats or dogs at a frequency of once per week.

The amino acid sequences of the present invention contain the standard single letter or three letter codes for twenty natural amino acids. In addition, "Aib" is α-aminoisobutyric acid, "αMePhe" is α-methylphenylalanine, "Pya (4)" is 4-pyridylalanine; "Cha" is cyclohexylalanine, "αMeTyr" is α-methyltyrosine.

"AEEA" as disclosed in the present invention is an abbreviation for 2-(2-amino-ethoxy)-ethoxy]-acetyl. "Ste" as disclosed in the present invention represents octadecane-dioyl-C(O)—$C_{16}H_{32}$—C(O)-derived from octadecanedioic acid.

"Effective amount" or "therapeutically effective amount" as disclosed in the present invention refers to the amount or dose of the compound or a pharmaceutically acceptable salt thereof according to the present invention which, upon single or multiple dose administration to the subject, provides the desired effect in the subject under diagnosis or treatment.

"Minimum effective dose" as disclosed in the present invention refers to the minimum administration dose at which the drug effect is produced. Specifically, as the drug effect experiment of multiple administrations on db/db mice in the present invention is concerned, it refers to the minimum dose at which the blood glucose AUC of the group taken the test compound is significantly different (p<0.05) from that of the Vehicle group.

"Efficacy dose" as disclosed in the present invention refers to the administration dose at which the drug effect is produced. Specifically, as the drug effect experiment of multiple administrations on db/db mice in the present invention is concerned, it refers to the dose at which the blood glucose AUC of the group taken the test compound is significantly different ($p < 0.05$) from that of the Vehicle group.

"Vehicle group" as disclosed in the present invention refers to the vehicle control group.

The "AUC" as disclosed in the present invention refers to the area under the concentration-time curve, that is, the area surrounded by the drug concentration-time curve and the time axis. This parameter is an important indicator to evaluate the degree of drug absorption, which reflects the exposure characteristics of a drug in the body.

The "MRT" as disclosed in the present invention refers to the mean residence time, and is the average value that a drug molecule resides in the body and means the time required for 63.2% of the drug to be eliminated from the body.

The "MTD" as disclosed in the present invention refers to the maximum tolerated dose, which is the highest dose that does not cause the death of the test animals.

The "internal standard" as disclosed in the present invention refers to a specified amount of a certain pure compound added to the sample for correcting the errors due to signal fluctuations of instruments, personnel operations and the like.

The "inhibition of blood glucose AUC" as disclosed in the present invention is the reduction percentage of blood glucose AUC in the group taken the test compound as compared with the group taken the Vehicle. Inhibition of blood glucose AUC=(blood glucose $AUC_{Vehicle}$-blood glucose $AUC_{test\ compound}$)/blood glucose $AUC_{Vehicle}$.

The "body weight change rate" as disclosed in the present invention is the change percentage of body weight in the group taken the test compound after administration as compared with the body weight thereof before administration, and reflects effect of the test compound on the body weight. Body weight change rate on day 28 (D28)=(body weight $_{D28\ after\ administration}$–body weight $_{before\ administration}$)/body weight $_{before\ administration}$×100%.

The "body weight reduction rate" as disclosed in the present invention is the reduction percentage of body weight in the group taken the test compound after administration as compared with the body weight thereof before administration, and reflects the reduction effect of the test compound. Weight reduction rate on day 28 (D28)=(body weight before administration-body weight $_{D28\ after\ administration}$)/body weight $_{before\ administration}$×100%.

"Treatment" as disclosed in the present invention includes attenuating, inhibiting, reversing, slowing, delaying or halting the progression or severity of an existing condition, disease, disorder or symptom. "Prevention" as disclosed in the present invention includes reducing the risk of acquiring a particular disease, disease condition or disorder.

The "titration strategy" as disclosed in the present invention is a dose escalation method, that is, after the initial dose, the frequency for dose escalation and the dosage are adjusted to obtain the optimal administration dosage.

The term "subject" includes humans and animals. The therapeutic utility of the compounds according to the present invention is applicable to a subject afflicted with a disease or condition as herein set forth and therefore in need of such treatment. As used herein the term "animal" is used merely for the purpose of pointing out human beings as opposed to other members of the animal kingdom.

The term "primate" includes humans (male or female) and non-human primates. The term "non-human" primate includes monkeys, such as a Cynomolgus Monkey.

The term "subject" includes humans and pets. The terms "pet" and "companion animal" are interchangeable and include non-human primates, rodent animals (especially rodent mammals), and non-human and non-rodent animals (especially non-human and non-rodent mammals). The term "rodent animal" or "rodent mammal" includes mice and rats. The term "non-human and non-rodent animal" or "non-human and non-rodent mammal" means an animal or a mammal that is neither human nor rodent. The term "non-human and non-rodent animal" or "non-human and non-rodent mammal" includes, but is not limited to, dogs, cats, rabbits, pigs, alpacas, horses, sheep and bovines.

The term "pet" or "companion animal" may be selected from the group consisting of monkeys, mice, rats, dogs, cats, rabbits, pigs, alpacas, horses, sheep and bovines. The "modifying chain" as disclosed in the present invention is ([2-(2-amino-ethoxy)-ethoxy]-acetyl)$_a$-($\gamma$-Glu)$_b$-CO—(CH$_2$)$_c$—Z, wherein each a is independently an integer from 0 to 5, each b is independently an integer from 0 to 5, and each c is independently an integer from 10 to 22; preferably, wherein a is independently selected from an integer of 1, 2, 3, 4 or 5, b is independently selected from an integer of 1, 2, 3, 4 or 5, and c is independently selected from an integer of 12 to 22; in addition, the present invention further provides compounds wherein c is 14, 16, 18 or 20, wherein Z is independently selected from the group consisting of —CH$_3$, carboxylic acids or carboxylic acid bioisosteres, phosphonates or sulfonates, for example, but not limited to the cases where said Z may comprise a carboxy acid (—CO$_2$H) or carboxylic acid bioisosteres (for example a phosphonic acid (—P(O)(OH)$_2$) or a sulfonic acid (—SO$_2$OH) group, preferably —CO$_2$H.

As for carboxylic acid bioisosteres, suitable carboxylic acid bioisosteres are well-known in the art. Preferably, the bioisosteres have protons with a pK$_a$ similar to that of the corresponding carboxylic acid. Examples of suitable bioisosteres may include, but are not limited to, tetrazoles, acylsulfonamides, acylhydroxylamines and squaric acid derivatives, as shown below:

R is Me or CF$_3$.

As for the peptides mentioned herein, according to conventional peptide designation, the left end is the N-terminus (amino-terminus) and the right end is the C-terminus (carboxyl-terminus). The C-terminus of the peptide can be any one of amide (—CONH$_2$), carboxyl (—COOH), carboxylate (—COO"), alkylamide (—CONHR') and ester (—COOR'), and R' is C$_{1-8}$ alkyl. In particular, amides (—CONH$_2$) are preferred.

The "coupling" or "incorporating" in the preparation process of the present invention refers to the process of adding a new amino acid to the combined amino acids or peptide.

DESCRIPTION OF DRAWINGS

FIG. 1A shows the blood glucose changes in db/db mice after a single subcutaneous administration of P007, P008, P014, P019, Tirzepatide and P001 at 10 nmol/kg; and FIG. 1B shows the blood glucose changes in db/db mice after a single subcutaneous administration of P013, P015, P016, P017, P018, P020 and Tirzepatide at 10 nmol/kg.

FIG. 2A shows the AUC from 0 to 48 hours after a single subcutaneous administration of P007, P008, P014, P019, Tirzepatide and P001 at 10 nmol/kg; FIG. 2B shows the AUC from 0 to 72 hours after a single subcutaneous administration of P007, P008, P014, P019 and Tirzepatide at 10 nmol/kg; and FIG. 2C shows the AUC from 0 to 56 hours after a single subcutaneous administration of P013, P015, P016, P017, P018, P020 and Tirzepatide at 10 nmol/kg. In FIG. 2A, T-Test, *$p<0.05$, $p<0.01$, *$p<0.001$, vs. vehicle; § $p<0.05$, §§ $p<0.01$, § § § $p<0.001$, vs. P001. In FIG. 2B, T-Test, *$p<0.05$, $p<0.01$, *$p<0.001$, vs. vehicle; #$p<0.05$, ##$p<0.01$, vs. Tirzepatide. In FIG. 2C, T-Test, *$p<0.05$, $p<0.01$, *$p<0.001$ vs. Vehicle; #$p<0.05$, vs. Tirzepatide.

FIG. 3A compares the changes of blood glucose in db/db mice after multiple subcutaneous administrations of P014 and Tirzepatide; FIG. 3B compares the changes of blood glucose in db/db mice after multiple subcutaneous administrations of P016 and Tirzepatide; FIG. 3C compares changes in blood glucose in db/db mice after multiple subcutaneous administrations of P017 and Tirzepatide; and FIG. 3D compares changes in blood glucose in db/db mice after multiple subcutaneous administrations of P020 and Tirzepatide.

In FIG. 5, ANOVA, *$P≤0.05$, ****$P≤0.0001$, vs. vehicle group; ####$P≤0.0001$ vs. positive control Tirzepatide at the same dose.

Figure 1A:
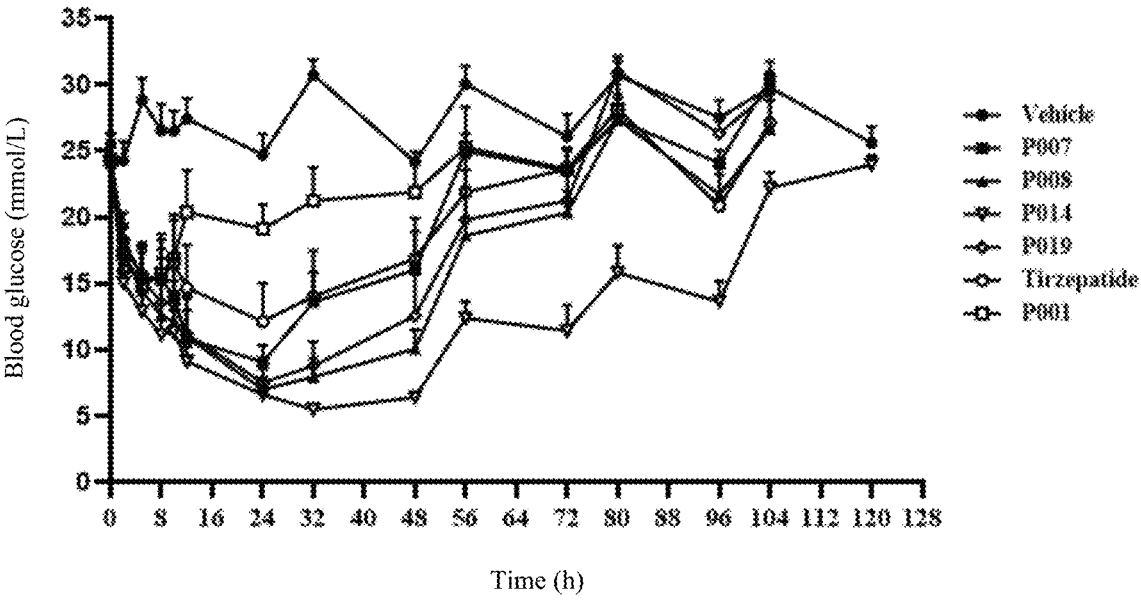
FIGS. 1A-1B show blood glucose changes in db/db mice after administration.

The present invention also includes novel intermediates and methods useful in the synthesis of compounds or pharmaceutically acceptable salts thereof according to the present invention. The intermediates and compounds according to the present invention can be prepared by various methods known in the art. In particular, methods using chemical synthesis are exemplified in the Examples below. The specific synthetic steps of each pathway as described can be combined in various ways to prepare compounds or salts thereof according to the present invention. Reagents and starting materials are readily available to those skilled in the art. It should be understood that these examples are not intended to limit the scope of the present invention in any way. The mass spectrometer is performed on an Agilent 1260/6110 liquid chromatography mass spectrometer, and the scanning range is between 100 and 1500.

DETAILED DESCRIPTION OF EMBODIMENTS

Embodiment 1. A compound of the following Formula (AI), or a pharmaceutically acceptable salt thereof:

Formula (AI)
(SEQ ID NO: 26)
Y-X$_1$-E-G-T-X$_2$-T-S-D-Y-A11-A12-A13-L-D-K-A17-A-

Q-A20-E-F-V-K-W-L-L-K-A29-G-P-S-S-G-A-P-P-P-S-

K;

wherein X$_1$ is Aib;

X$_2$ is αMePhe;

A11 is Aib;

A12 is Ile;

A13 is Aib;

A17 is Gln;

A20 is Ala;

A29 is Gly,

1 K, which is selected from the group consisting of K at position 24 and K at position 28, is chemically modified through conjugation to the ε-aminos of the K side-chains with ([2-(2-amino-ethoxy)-ethoxy]-acetyl)$_a$-(γ-Glu)$_b$-CO—(CH$_2$)$_c$—Z, wherein each a is independently selected from an integer of 1, 2 and 3, each b is independently selected from an integer of 1, 2 and 3, and each c is independently selected from an integer of 16, 18 and 20, wherein Z is independently selected from the group consisting of —CH$_3$ and carboxylic acids; and the C-terminal amino acid is amidated as a C-terminal primary amide.

Embodiment 2. The compound according to Embodiment 1, wherein

K at position 24 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H; or K at position 28 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H.

Embodiment 3. The compound according to Embodiment 1 or Embodiment 2, wherein

K at position 24 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein each a is independently selected from an integer of 2 and 3, each b is independently 1 and 3, and each c is independently selected from an integer of 16, 18 and 20, wherein Z is independently selected from carboxylic acids.

Embodiment 4. The compound according to Embodiment 1 or Embodiment 2, wherein

K at position 28 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein each a is independently selected from an integer of 2 and 3, each b is independently selected from an integer of 1 and 3, and each c is independently selected from an integer of 16, 18 and 20, wherein Z is independently selected from carboxylic acids.

Embodiment 5. The compound according to Embodiment 1, wherein

K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{16}$—CO$_2$H; and the C-terminal amino acid is amidated as a C-terminal primary amide (SEQ ID NO:2); or K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{18}$—CO$_2$H; and the C-terminal amino acid is amidated as a C-terminal primary amide (SEQ ID NO:4); or K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{20}$—CO$_2$H; and the C-terminal amino acid is amidated as a C-terminal primary amide (SEQ ID NO:5); or K at position 24 is chemically modified through conjugation to the ε-amino of the K side-chain with ([2-(2-amino-ethoxy)-ethoxy]-acetyl)$_2$-(γ-Glu)$_3$-CO—(CH$_2$)$_{16}$—CO$_2$H; and the C-terminal amino acid is amidated as a C-terminal primary amide (SEQ ID NO:6); or K at position 24 is chemically modified through conjugation to the ε-amino of the K side-chain with ([2-(2-amino-ethoxy)-ethoxy]-acetyl) 3-(γ-Glu)$_1$-CO—(CH$_2$)$_{20}$—CO$_2$H; and the C-terminal amino acid is amidated as a C-terminal primary amide (SEQ ID NO:7); or K at position 28 is chemically modified through conjugation to the ε-amino of the K side-chain with ([2-(2-amino-ethoxy)-ethoxy]-acetyl)$_2$-(γ-Glu)$_1$-CO—(CH$_2$)$_{16}$—CO$_2$H; and the C-terminal amino acid is amidated as a C-terminal primary amide (SEQ ID NO:3); or K at position 28 is chemically modified through conjugation to the ε-amino of the K side-chain with ([2-(2-amino-ethoxy)-ethoxy]-acetyl)$_2$-(γ-Glu)$_1$-CO—(CH$_2$)$_{20}$—CO$_2$H; and the C-terminal amino acid is amidated as a C-terminal primary amide (SEQ ID NO:8); or K at position 28 is chemically modified through conjugation to the ε-amino of the K side-chain with ([2-(2-amino-ethoxy)-ethoxy]-acetyl)$_2$-(γ-Glu)$_3$-CO—(CH$_2$)$_{16}$—CO$_2$H; and the C-terminal amino acid is amidated as a C-terminal primary amide (SEQ ID NO:9); or K at position 28 is chemically modified through conjugation to the ε-amino of the K side-chain with ([2-(2-amino-ethoxy)-ethoxy]-acetyl) 3-(γ-Glu)$_1$-CO—(CH$_2$)$_{16}$—CO$_2$H; and the C-terminal amino acid is amidated as a C-terminal primary amide (SEQ ID NO:10); or K at position 28 is chemically modified through conjugation to the ε-amino of the K side-chain with ([2-(2-amino-ethoxy)-ethoxy]-acetyl) 3-(γ-Glu)$_1$-CO—(CH$_2$)$_{20}$—CO$_2$H; and the C-terminal amino acid is amidated as a C-terminal primary amide (SEQ ID NO:11).

Embodiment 6. The compound according to Embodiment 5, wherein the compound is (SEQ ID NO: 2)

(SEQ ID NO: 3)

-continued (SEQ ID NO: 4)

(SEQ ID NO: 5)

-continued (SEQ ID NO: 6)

(SEQ ID NO: 7)

-continued (SEQ ID NO: 8)

(SEQ ID NO: 9)

-continued (SEQ ID NO: 10)

(SEQ ID NO: 11)

or a pharmaceutically acceptable salt thereof.

Embodiment 7. A pharmaceutical composition comprising the compound according to any one of Embodiment 1 to Embodiment 6, and a pharmaceutically acceptable carrier, diluent or excipient.

Embodiment 8. A method for treating or preventing a disease selected from hyperglycemia, impaired glucose tolerance, Type I diabetes mellitus, Type II diabetes mellitus, obesity, hypertension, Syndrome X, dyslipidemia, cognitive impairment, atherosclerosis, myocardial infarction, coronary heart disease and other cardiovascular diseases, stroke, inflammatory bowel syndrome, dyspepsia and gastric ulcers, comprising administering to a subject in need thereof, an effective amount of the compound according to any one of Embodiment 1 to Embodiment 6;

Preferably, the disease is Type II diabetes mellitus.

Embodiment 9. A method for reducing food intake, reducing β-cell apoptosis, increasing β-cell function and β-cell volume, and/or restoring glucose sensitivity of β-cell, comprising administering to a subject in need thereof, an effective amount of the compound according to any one of Embodiment 1 to Embodiment 6.

Embodiment 10. A method for treating or preventing a disease, comprising administering to a subject in need thereof, an effective amount of a compound of Formula (AI) or a pharmaceutically acceptable salt thereof:

```
Formula (AI)
                                    (SEQ ID NO: 13)
Y-X₁-E-G-T-X₂-T-S-D-Y-A11-A12-A13-L-D-K-A17-A-

Q-A20-E-F-V-K-W-L-L-K-A29-G-P-S-S-G-A-P-P-P-S-

K;
``` wherein $X_1$ is Aib;
$X_2$ is αMePhe;
A11 is Aib or Ala;
A12 is Ala, Ile, Lys, Phe or Pya (4);
A13 is Aib, Cha, Leu, αMePhe or αMeTyr;
A17 is Gln or Ile;
A20 is Ala or Ser; and
A29 is Gln or Gly;
1, 2, 3 or 4 Ks, which are selected from the group consisting of K at position 16, K at position 24, K at position 28 and K at position 40, are chemically modified through conjugation to the $\varepsilon$-aminos of the K side-chains with ([2-(2-amino-ethoxy)-ethoxy]-acetyl)$_a$-(γ-Glu)$_b$-CO—(CH$_2$)$_c$—Z, wherein each a is independently an integer from 0 to 5, each b is independently an integer from 0 to 5, and each c is independently an integer from 10 to 24, Z is independently selected from the group consisting of —CH$_3$, carboxylic acids or carboxylic acid bioisosteres, phosphonates or sulfonates, and the C-terminal amino acid is amidated as a C-terminal primary amide.

Embodiment 11. The method according to Embodiment 10, comprising administering to a subject in need thereof, an effective amount of a compound of Formula (AI) or a pharmaceutically acceptable salt thereof:

```
Formula (AI)
                                    (SEQ ID NO: 25)
Y-X₁-E-G-T-X₂-T-S-D-Y-A11-A12-A13-L-D-K-A17-A-

Q-A20-E-F-V-K-W-L-L-K-A29-G-P-S-S-G-A-P-P-P-S-

K;
``` wherein $X_1$ is Aib;
$X_2$ is αMePhe;
A11 is Aib;
A12 is Ile;
A13 is Aib;
A17 is Gln;
A20 is Ala; and
A29 is Gly,
1 or 2 Ks, which are selected from the group consisting of K at position 16, K at position 24, K at position 28 and K at position 40, are chemically modified through conjugation to the $\varepsilon$-aminos of the K side-chains with ([2-(2-amino-ethoxy)-ethoxy]-acetyl)$_a$-(γ-Glu)$_b$-CO—(CH$_2$)$_c$—Z, wherein each a is independently an integer from 0 to 5, each b is independently an integer from 0 to 5, and each c is independently an integer from 10 to 22, Z is independently selected from the group consisting of —CH$_3$, carboxylic acids or carboxylic acid bioisosteres, phosphonates or sulfonates, and the C-terminal amino acid is amidated as a C-terminal primary amide.

Embodiment 12. The method according to Embodiment 10 or 11, wherein
K at position 16 is chemically modified through conjugation to the $\varepsilon$-amino of the K side-chain with ([2-(2-amino-ethoxy)-ethoxy]-acetyl)$_a$-(γ-Glu)$_b$-CO—(CH$_2$)$_c$—CO$_2$H;
K at position 24 is chemically modified through conjugation to the $\varepsilon$-amino of the K side-chain with ([2-(2-amino-ethoxy)-ethoxy]-acetyl)$_a$-(γ-Glu)$_b$-CO—(CH$_2$)$_c$—CO$_2$H;
K at position 28 is chemically modified through conjugation to the $\varepsilon$-amino of the K side-chain with ([2-(2-amino-ethoxy)-ethoxy]-acetyl)$_a$-(γ-Glu)$_b$-CO—(CH$_2$)$_c$—CO$_2$H; or
K at position 40 is chemically modified through conjugation to the $\varepsilon$-amino of the K side-chain with ([2-(2-amino-ethoxy)-ethoxy]-acetyl)$_a$-(γ-Glu)$_b$-CO—(CH$_2$)$_c$—CO$_2$H.

Embodiment 13. The method according to any one of Embodiment 10 to Embodiment 12, wherein
K at position 24 and K at position 28 are chemically modified with two modifying chains through conjugation to the $\varepsilon$-aminos of the K side-chains with ([2-(2-amino-ethoxy)-ethoxy]-acetyl)$_a$-(γ-Glu)$_b$-CO—(CH$_2$)$_c$—CO$_2$H;
K at position 16 and K at position 24 are chemically modified with two modifying chains through conjugation to the $\varepsilon$-aminos of the K side-chains with ([2-(2-amino-ethoxy)-ethoxy]-acetyl)$_a$-(γ-Glu)$_b$-CO—(CH$_2$)$_c$—CO$_2$H;
K at position 16 and K at position 28 are chemically modified with two modifying chains through conjugation to the $\varepsilon$-aminos of the K side-chains with ([2-(2-amino-ethoxy)-ethoxy]-acetyl)$_a$-(γ-Glu)$_b$-CO—(CH$_2$)$_c$—CO$_2$H;
K at position 16 and K at position 40 are chemically modified with two modifying chains through conjugation to the $\varepsilon$-aminos of the K side-chains with ([2-(2-amino-ethoxy)-ethoxy]-acetyl)$_a$-(γ-Glu)$_b$-CO—(CH$_2$)$_c$—CO$_2$H;
K at position 24 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H; or K at position 28 and K at position 40 are chemically modified with two modifying chains through conjugation to the ε-aminos of the K side-chains with ([2-(2-amino-ethoxy)-ethoxy]-acetyl)$_a$-(γ-Glu)$_b$-CO—(CH$_2$)$_c$—CO$_2$H.

Embodiment 14. The method according to any one of Embodiment 10 to Embodiment 13, wherein a is independently selected from an integer of 1, 2, 3, 4 or 5, b is independently selected from an integer of 1, 2, 3, 4 or 5, and c is independently selected from an integer of 12 to 22; and furthermore, c is independently selected from an integer of 14, 16, 18 or 20; and/or Z is —CO$_2$H.

Embodiment 15. The method according to any one of Embodiment 10 to Embodiment 14, wherein the compound is

```
Formula (I)
                                      (SEQ ID NO: 15)
Y-X₁-E-G-T-X₂-T-S-D-Y-X₃-I-X₄-L-D-K-Q-A-Q-A-E-

F-V-K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, c is independently selected from an integer of 10 to 24, and the C-terminal amino acid is amidated as a C-terminal primary amide; preferably, wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 2 and 3, b is independently 1, c is independently selected from an integer of 16, 18 and 20, and Z is independently selected from carboxylic acids.

Embodiment 16. The method according to any one of Embodiment 10 to Embodiment 15, wherein the compound is

```
Formula (I)
                                      (SEQ ID NO: 16)
Y-X₁-E-G-T-X₂-T-S-D-Y-X₃-I-X₄-L-D-K-Q-A-Q-A-E-

F-V-K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 0 to 5, b is independently selected from an integer of 0 to 5, c is independently selected from an integer of 10 to 24, and the C-terminal amino acid is amidated as a C-terminal primary amide;

preferably, wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl)$_a$-(γ-Glu)$_b$-CO—(CH$_2$)$_c$—CO$_2$H, wherein a is independently selected from an integer of 2 and 3, b is independently selected from an integer of 1 and 3, c is independently selected from an integer of 16, 18 and 20, and Z is independently selected from carboxylic acids.

Embodiment 17. The method according to Embodiment 15 or Embodiment 16, wherein a is independently selected from an integer of 1, 2, 3, 4 or 5, b is independently selected from an integer of 1, 2, 3, 4 or 5, and c is independently selected from an integer of 12 to 22; and preferably, c is independently selected from an integer of 14, 16, 18 or 20.

Embodiment 18. The method according to any one of Embodiment 10 to Embodiment 14, wherein the compound is

```
                                      (SEQ ID NO: 2)
Y-X₁-E-G-T-X₂-T-S-D-Y-X₃-I-X₄-L-D-K-Q-A-Q-A-E-

F-V-K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{16}$—CO$_2$H; and the C-terminal amino acid is amidated as a C-terminal primary amide (sequence 2, SEQ ID NO:7); or

```
                                      (SEQ ID NO: 4)
Y-X₁-E-G-T-X₂-T-S-D-Y-X₃-I-X₄-L-D-K-Q-A-Q-A-E-

F-V-K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{18}$—CO$_2$H; and the C-terminal amino acid is amidated as a C-terminal primary amide (sequence 4, SEQ ID NO:13); or

```
                                      (SEQ ID NO: 5)
Y-X₁-E-G-T-X₂-T-S-D-Y-X₃-I-X₄-L-D-K-Q-A-Q-A-E-

F-V-K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{20}$—CO$_2$H; and the C-terminal amino acid is amidated as a C-terminal primary amide (sequence 5, SEQ ID NO:14); or

```
                                      (SEQ ID NO: 6)
Y-X₁-E-G-T-X₂-T-S-D-Y-X₃-I-X₄-L-D-K-Q-A-Q-A-E-

F-V-K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_2$-(γ-Glu)$_3$-CO—(CH$_2$)$_{16}$—CO$_2$H; and the C-terminal amino acid is amidated as a C-terminal primary amide (sequence 6, SEQ ID NO:15); or

```
                                      (SEQ ID NO: 7)
Y-X₁-E-G-T-X₂-T-S-D-Y-X₃-I-X₄-L-D-K-Q-A-Q-A-E-

F-V-K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl) 3-($\gamma$-Glu)$_1$-CO—(CH$_2$)$_{20}$—CO$_2$H; and the C-terminal amino acid is amidated as a C-terminal primary amide (sequence 7, SEQ ID NO:16); or

```
                                    (SEQ ID NO: 3)
Y-X₁-E-G-T-X₂-T-S-D-Y-X₃-I-X₄-L-D-K-Q-A-Q-A-E-

F-V-K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl)$_2$-($\gamma$-Glu)$_1$-CO—(CH$_2$)$_{16}$—CO$_2$H; and the C-terminal amino acid is amidated as a C-terminal primary amide (sequence 3, SEQ ID NO:8); or

```
                                    (SEQ ID NO: 8)
Y-X₁-E-G-T-X₂-T-S-D-Y-X₃-I-X₄-L-D-K-Q-A-Q-A-E-

F-V-K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl)$_2$-($\gamma$-Glu)$_1$-CO—(CH$_2$)$_{20}$—CO$_2$H; and the C-terminal amino acid is amidated as a C-terminal primary amide (sequence 8, SEQ ID NO:17); or

```
Y-X₁-E-G-T-X₂-T-S-D-Y-X₃-I-X₄-L-D-K-Q-A-Q-A-E-F-V-
K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl)$_2$-($\gamma$-Glu)$_3$-CO—(CH$_2$)$_{16}$—CO$_2$H; and the C-terminal amino acid is amidated as a C-terminal primary amide (sequence 9, SEQ ID NO:18); or

```
Y-X₁-E-G-T-X₂-T-S-D-Y-X₃-I-X₄-L-D-K-Q-A-Q-A-E-F-V-
K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl) 3-($\gamma$-Glu)$_1$-CO—(CH$_2$)$_{16}$—CO$_2$H; and the C-terminal amino acid is amidated as a C-terminal primary amide (sequence 10, SEQ ID NO:19); or

```
Y-X₁-E-G-T-X₂-T-S-D-Y-X₃-I-X₄-L-D-K-Q-A-Q-A-E-F-V-
K-W-L-L-K-G-G-P-S-S-G-A-P-P-P-S-K;
``` wherein X$_1$ is Aib; X$_2$ is αMePhe; X$_3$ is Aib; X$_4$ is Aib; K at position 28 is chemically modified through conjugation to the ε-amino of the K side-chain with ([2-(2-amino-ethoxy)-ethoxy]-acetyl) 3-($\gamma$-Glu)$_1$-CO—(CH$_2$)$_{20}$—CO$_2$H; and the C-terminal amino acid is amidated as a C-terminal primary amide.

Embodiment 19. The method according to Embodiment 18, wherein the compound is (SEQ ID NO: 2)

(SEQ ID NO: 3)

-continued (SEQ ID NO: 4)

(SEQ ID NO: 5)

-continued (SEQ ID NO: 6)

(SEQ ID NO: 7)

-continued (SEQ ID NO: 8)

(SEQ ID NO: 9)

-continued (SEQ ID NO: 10)

H—Y—N(H)—E—G—T—N—T—S—D—Y—NH—I—NH—L—D—K—Q—A—E—F—V—K—W—L—L—NH—G—G—P—S—S—G—A—P—P—S—K—NH₂, (SEQ ID NO: 11)

H—Y—N(H)—E—G—T—N—T—S—D—Y—NH—I—NH—L—D—K—Q—A—E—F—V—K—W—L—L—NH—G—G—P—S—S—G—A—P—P—S—K—NH₂, or a pharmaceutically acceptable salt thereof.

Embodiment 20. The method according to any one of Embodiment 10 to Embodiment 19, wherein the disease is selected from hyperglycemia, impaired glucose tolerance, Type I diabetes mellitus, Type II diabetes mellitus, obesity, hypertension, Syndrome X, dyslipidemia, cognitive impairment, atherosclerosis, myocardial infarction, coronary heart disease and other cardiovascular diseases, stroke, inflammatory bowel syndrome, dyspepsia and gastric ulcers.

Embodiment 21. The method according to any one of Embodiment 10 to Embodiment 20, wherein the compound or the pharmaceutically acceptable salt thereof is used for delaying or preventing the disease development of Type II diabetes mellitus.

Embodiment 22. The method according to any one of Embodiment 10 to Embodiment 19, wherein the compound or the pharmaceutically acceptable salt thereof is used for reducing food intake, reducing β-cell apoptosis, increasing β-cell function and β-cell volume, and/or restoring glucose sensitivity of β-cell.

Embodiment 23. The method according to any one of any one of Embodiment 10 to Embodiment 19, wherein the disease includes dyslipidaemia, obesity and/or hepatic steatosis associated with insulin resistance and diabetes mellitus.

Embodiment 24. The method according to any one of Embodiment 10 to Embodiment 19, wherein the disease includes osteopenia and bone/joint diseases, such as knee osteoarthritis, hip osteoarthritis, spondylitis deformans, and/or osphyalgia.

Embodiment 25. The method according to any one of Embodiment 10 to Embodiment 19, wherein the compound or the pharmaceutically acceptable salt thereof is used for chronic weight management as an adjunct to a reduced-calorie diet and increased physical activity in an overweight or obese animal.

Embodiment 26. The method according to any one of Embodiment 10 to Embodiment 19, wherein the disease includes symptomatic obesity, obesity based on simple obesity, obesity-related conditions or diseases, eating disorders, diabetes mellitus (for example, Type I diabetes mellitus, Type II diabetes mellitus, gestational diabetes mellitus, obesity diabetes mellitus), hyperlipidemia (e.g., hypertriglyceridemia, hypercholesterolemia, hyper-LDL-cholesterolemia, low HDL-cholesterolemia, postprandial hyperlipidemia), hypertension, heart failure, complications of diabetes mellitus (for example, neuropathy, nephropathy, retinopathy, diabetic cardiomyopathy, cataract, macroangiopathy, osteopenia, hyperosmolar diabetic coma), infectious disease (for example, respiratory tract infection, urinary tract infection, gastrointestinal infection, superficial soft tissue infection, lower extremity infection), diabetic gangrene, xerostomia, hypacusia, cerebrovascular disorder, peripheral blood circulation disorder, metabolic syndrome (with three or more conditions selected from the group consisting of hypertriglyceridemia (TG), low HDL-cholesterolemia (HDL-C), hypertension, abdominal obesity, and impaired glucose tolerance), and sarcopenia.

Embodiment 27. The method according to any one of Embodiment 10 to Embodiment 26, wherein the subject is a human or an animal.

Embodiment 28. The method according to any one of Embodiment 10 to Embodiment 26, wherein the subject is a human, or a pet or a companion animal.

Embodiment 29. The method according to any one of Embodiment 10 to Embodiment 28, wherein the subject is a human.

Embodiment 30. The method according to any one of Embodiment 10 to Embodiment 28, wherein the subject is a pet or a companion animal.

Embodiment 31. The method according to Embodiment 30, wherein the pet or the companion animal is selected from non-human primates, rodent animals, and non-human and non-rodent animals.

Embodiment 32. The method according to Embodiment 28, wherein the pet or the companion animal is selected from the group consisting of monkeys, mice, rats, dogs, cats, rabbits, pigs, alpacas, horses, sheep and bovines.

Embodiment 33. The method according to any one of Embodiment 10 to Embodiment 28, wherein the subject is a dog or a cat.

Embodiment 34. The method according to any one of Embodiment 10 to Embodiment 33, wherein the compound or the pharmaceutically acceptable salt thereof is used for treating Type II diabetes mellitus, overweight or obesity in humans.

Embodiment 35. The method according to any one of Embodiment 10 to Embodiment 33, wherein the compound or the pharmaceutically acceptable salt thereof is used for treating Type II diabetes mellitus, overweight or obesity in dogs or cats.

Embodiment 36. The method according to any one of Embodiment 10 to Embodiment 35, wherein the compound or the pharmaceutically acceptable salt thereof is administered in the form a solution or a suspension.

Embodiment 37. The method according to any one of Embodiment 10 to Embodiment 36, wherein the compound or the pharmaceutically acceptable salt thereof is administered by subcutaneous injection.

Embodiment 38. The method according to any one of Embodiment 10 to Embodiment 37, wherein the compound or the pharmaceutically acceptable salt thereof is administered in cats or dogs at a dose of 0.003 to 0.6 mg/kg, calculated based on body surface area.

Embodiment 39. The method according to any one of Embodiment 10 to Embodiment 38, wherein the compound or the pharmaceutically acceptable salt thereof is administered in cats or dogs at a frequency of once per week.

Embodiment 40. The method according to any one of Embodiment 10 to Embodiment 39, wherein the compound or the pharmaceutically acceptable salt thereof is selected from SEQ ID NO: 5, SEQ ID NO:7 and SEQ ID NO: 11.

Example 1

Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K;

wherein $X_1$ is Aib; $X_2$ is αMePhe; $X_3$ is Aib; $X_4$ is Aib; K at position 24 is chemically modified through conjugation to the ε-amino of the K side-chain with ([2-(2-amino-ethoxy)-ethoxy]-acetyl)$_2$-(γ-Glu)$_3$-CO—$(CH_2)_{16}$—$CO_2H$; and the C-terminal amino acid is amidated as a C-terminal primary amide.

The above structure contains the standard single letter amino acid code with exception of residues Aib2, αMePhe6, Aib11, Aib13 and K24 where the structures of amino acid residues Aib2, αMePhe6, Aib11, Aib13 and K24 have been expanded.

(1) Synthesis of Peptide-Resin Intermediate 1

Fmoc-Rink Linker-Nle-MBHA resin (S=0.49 mmol/g) is charged, swelled with an appropriate amount of DCM, washed with DCM for 2 to 3 times, de-protected with 20% PIP/DMF solution for 30 minutes, filtered and washed to obtain a NH₂-Rink linker-Nle-MBHA resin with Fmoc removed, which is suctioned to remove the solvent for further use.

4 equivalents of Fmoc-Lys(Boc)-OH and HOBt are charged respectively, and dissolved in an appropriate amount of DMF/DCM. Separately, 4 equivalents of DIC is charged and double diluted with DCM. The resultant diluent is slowly added to the DMF/DCM solution, and reacted under stirring at −5 to 0° C. for no less than 60 minutes so as to be activated for further use.

The activated Fmoc-Lys(Boc)-OH solution is added to the NH₂-Rink linker-Nle-MBHA resin. The reaction temperature is controlled at 10 to 30° C. The coupling reaction is performed for 240 to 480 minutes. After filtration and washing, a Fmoc-Lys(Boc)-Rink linker-Nle-MBHA resin is obtained. The resin is de-protected with 20% PIP/DMF solution for 30 minutes. After filtration and washing, a Lys(Boc)-Rink linker-Nle-MBHA resin with Fmoc removed is obtained.

According to the reaction conditions as stated above, each amino acid is successively coupled starting from the second amino acid at the C-terminus to the N-terminus. If the coupling is incomplete (a color development reaction occurs), a second condensation is carried out using HBTU/DIEA to ensure that each amino acid is completely condensed. The couplings are successively performed in the following order: Fmoc-Ser(tBu)-OH, Fmoc-Pro-OH, Fmoc-Pro-OH, Fmoc-Pro-OH, Fmoc-Ala-OH·H₂O, Fmoc-Gly-OH, Fmoc-Ser(tBu)-OH, Fmoc-Ser(tBu)-OH, Fmoc-Pro-OH, Fmoc-Gly-Gly-OH, Fmoc-Lys(Boc)-OH, Fmoc-Leu-OH, Fmoc-Leu-OH, Fmoc-Trp(Boc)-OH, Fmoc-Lys(Mtt)-OH, Fmoc-Val-OH, Fmoc-Phe-OH, Fmoc-Glu(OtBu)-OH·H₂O, Fmoc-Ala-OH·H₂O, Fmoc-Gln(Trt)-OH, Fmoc-Ala-OH·H₂O, Fmoc-Gln(Trt)-OH, Fmoc-Lys(Boc)-OH, Fmoc-Asp(OtBu)-OH, Fmoc-Leu-OH, Fmoc-Aib-OH, Fmoc-Ile-OH, Fmoc-Aib-OH, Fmoc-Tyr(tBu)-OH, Fmoc-Asp(OtBu)-OH, Fmoc-Ser(tBu)-OH, Fmoc-Thr(tBu)-OH, Fmoc-α-Me-Phe-OH, Fmoc-Thr(tBu)-OH, Fmoc-Glu(OtBu)-Gly-OH, Fmoc-Aib-OH and Boc-Tyr(tBu)-OH.

The following resin is obtained: Boc-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Gln(Trt)-Ala-Glu(OtBu)-Phe-Val-Lys(Mtt)-Trp(Boc)-Leu-Leu- Lys(Boc)-Gly-Gly-Pro-Ser(tBu)-Ser(tBu)-Gly-Ala-Pro-Pro-Pro-Ser(tBu)-Lys(Boc)-Rink Linker-Nle-MBHA resin.

When the above condensation is complete, the Mtt protecting groups are removed with 50% HFIP/DCM solution for 30 minutes. After washing and filtration, the following peptide-resin intermediate 1 is obtained:

Boc-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Glu(OtBu)-Phe-Val-Lys-Trp(Boc)-Leu-Leu-Lys(Boc)-Gly-Gly-Pro-Ser(tBu)-Ser(tBu)- Gly-Ala-Pro-Pro-Pro-Ser(tBu)-Lys(Boc)-Rink Linker-Nle-MBHA Resin.

(2) Modification Steps with Modifying Chain 4 equivalents of Fmoc-AEEA-OH and HOBt are charged, and dissolved in an appropriate amount of DMF/DCM. Separately, 4 equivalents of DIC is charged and double diluted with DCM. The diluent is slowly added to the DMF/DCM solution, and reacted under stirring at −5 to 0° C. for no less than 60 minutes so as to be activated for further use.

The activated Fmoc-AEEA-OH solution is added to the previously swollen and washed peptide-resin intermediate 1. The reaction temperature is controlled at 10 to 30° C. The coupling reaction is performed for 240 to 480 minutes. The resin is filtrated and washed. The Fmoc protecting groups are removed with 20% PIP/DMF solution for 30 minutes. The resin is filtrated and washed. According to the reaction conditions as stated above, the activated Fmoc-AEEA-OH, Fmoc-AEEA-OH, Fmoc-Glu(α-OtBu)-OH, Fmoc-Glu(α-OtBu)-OH, Fmoc-Glu(α-OtBu)-OH and mono-tert-butyl octadecanedioate are successively coupled on the resin, Fmoc deprotected, washed with DCM and dried to obtain the following P015 peptide-resin: Boc-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Gln(Trt)-Ala-Glu(OtBu)-Phe-Val-Lys(tBuO-Ste-γ-Glu(α-OtBu)-γ-Glu(α-OtBu)-γ-Glu(α-OtBu)-AEEA-AEEA)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Rink-Linker-Nle-MBHA Resin.

The P015 peptide-resin is charged. 12-15 mL/g cleavage reagent for the peptide-resin (TFA:EDT:TIS:H₂O, 94:2:2:2 v/v) is added and reacted with stirring at 25±5° C. for 4 hours. The reaction mixture is filtered with a sand core funnel. The filtrate is collected. The resin is washed with a small amount of TFA for three times, and the filtrates are combined and concentrated under reduced pressure. Methyl tert-butyl ether (MBTE) is added, and the resulting precipitate is washed with MBTE for 3 to 4 times, and dried by evaporating MBTE. The crude product is dried under reduced pressure at room temperature to constant weight to obtain the crude P015 product, which is subsequently purified and dried to obtain the P015 sample (the molecular weight determined by MS is 5255.2).

Example 2

Y-X₁-E-G-T-X₂-T-S-D-Y-X₃-I-X₄-L-D-K-Q-A-Q-A-E-F-V-K-W-L-L-K-G-G-P-S-S-G-A-P-P-P-S-K;

wherein $X_1$ is Aib; $X_2$ is αMePhe; $X_3$ is Aib; $X_4$ is Aib; K at position 28 are chemically modified through conjugation to the ε-aminos of the K side-chains with ([2-(2-amino-ethoxy)-ethoxy]-acetyl) 3-(γ-Glu)₁-CO—(CH₂)₁₆—CO₂H; and the C-terminal amino acid is amidated as a C-terminal primary amide.

—G—P—S—S—G—A—P—P—P—S—K—NH₂

The above structure contains the standard single letter amino acid code with exception of residues Aib2, αMePhe6, Aib11, Aib13 and K28 where the structures of amino acid residues Aib2, αMePhe6, Aib11, Aib13 and K28 have been expanded.

The preparation method applies a Fmoc solid-phase polypeptide synthesis strategy, said method comprising:

(1) Synthesis of Peptide-Resin Intermediate 2

Fmoc-Rink Linker-Nle-MBHA resin (S=0.49 mmol/g) is charged, swelled with an appropriate amount of DCM, washed with DCM for 2 to 3 times, de-protected with 20% PIP/DMF solution for 30 mins, washed and filtered to obtain a NH₂-Rink linker-Nle-MBHA resin with Fmoc removed, which is suctioned to remove the solvent for further use.

4 equivalents of Fmoc-Lys(Boc)-OH and HOBt are charged respectively, and dissolve in an appropriate amount of DMF/DCM. Separately, 4 equivalents of DIC is charged and double diluted with DCM. The diluent is slowly added to the DMF/DCM solution, and reacted under stirring at −5 to 0° C. for no less than 60 minutes so as to be activated for further use.

The activated Fmoc-Lys(Boc)-OH solution is added to the NH₂-Rink linker-Nle-MBHA resin. The reaction temperature is controlled at 10 to 30° C. The coupling reaction is performed for 240 to 480 minutes. After filtration and washing, a Fmoc-Lys(Boc)-Rink linker-Nle-MBHA resin is obtained. The resin is de-protected with 20% PIP/DMF solution for 30 min. After filtration and washing, a Lys (Boc)-Rink linker-Nle-MBHA resin with Fmoc removed is obtained.

According to the reaction conditions as stated above, each amino acid is successively coupled starting from the second amino acid at the C-terminus to the N-terminus. If the coupling is incomplete (a color development reaction occurs), a second condensation is carried out using HBTU/DIEA to ensure that each amino acid is completely condensed. The coupling are successively performed in the following order: Fmoc-Ser(tBu)-OH, Fmoc-Pro-OH, Fmoc-Pro-OH, Fmoc-Pro-OH, Fmoc-Ala-OH·H₂O, Fmoc-Gly-OH, Fmoc-Ser(tBu)-OH, Fmoc-Ser(tBu)-OH, Fmoc-Pro-OH, Fmoc-Gly-Gly-OH, Fmoc-Lys(Mtt)-OH, Fmoc-Leu-OH, Fmoc-Leu-OH, Fmoc-Trp(Boc)-OH, Fmoc-Lys(Boc)-OH, Fmoc-Val-OH, Fmoc-Phe-OH, Fmoc-Glu(OtBu)-OH·H₂O, Fmoc-Ala-OH·H₂O, Fmoc-Gln(Trt)-OH, Fmoc-Ala-OH·H₂O, Fmoc-Gln(Trt)-OH, Fmoc-Lys(Boc)-OH, Fmoc-Asp(OtBu)-OH, Fmoc-Leu-OH, Fmoc-Aib-OH, Fmoc-Ile-OH, Fmoc-Aib-OH, Fmoc-Tyr(tBu)-OH, Fmoc-Asp(OtBu)-OH, Fmoc-Ser(tBu)-OH, Fmoc-Thr(tBu)-OH, Fmoc-α-Me-Phe-OH, Fmoc-Thr(tBu)-OH, Fmoc-Glu (OtBu)-Gly-OH, Fmoc-Aib-OH and Boc-Tyr(tBu)-OH.

The following resin is obtained:

Boc-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Gln(Trt)-Ala-Glu(OtBu)-Phe-Val-Lys(Boc)-Trp(Boc)-Leu-Leu-Lys(Mtt)-Gly-Gly-Pro-Ser(tBu)- Ser(tBu)-Gly-Ala-Pro-Pro-Pro-Ser(tBu)-Lys(Boc)-Rink Linker-Nle-MBHA Resin.

When the above condensation is complete, the Mtt protecting groups are removed with 50% HFIP/DCM solution for 30 minutes. After washing and filtration, the following peptide-resin intermediate 2 is obtained: Boc-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Gln(Trt)-Ala-Glu(OtBu)-Phe-Val-Lys(Boc)-Trp(Boc)-Leu-Leu- Lys-Gly-Gly-Pro-Ser(tBu)-Ser(tBu)-Gly-Ala-Pro-Pro-Pro-Ser(tBu)-Lys(Boc)-Rink Linker-Nle-MBHA Resin.

(2) Modification Steps with Modifying Chain 4 equivalents of Fmoc-AEEA-OH and HOBt are charged, and dissolve in an appropriate amount of DMF/DCM. Separately, 4 equivalents of DIC is charged and double diluted with DCM. The diluent is slowly added to the DMF/DCM solution, and reacted under stirring at −5 to 0° C. for no less than 60 minutes so as to be activated for further use.

The activated Fmoc-AEEA-OH solution is added to the previously swollen and washed peptide-resin intermediate 2. The reaction temperature is controlled at 10 to 30° C. The coupling reaction is performed for 240 to 480 minutes. The resin is filtrated and washed. The Fmoc protecting groups are removed with 20% PIP/DMF solution for 30 minutes. The resin is filtrated and washed. According to the reaction conditions as stated above, the activated Fmoc-AEEA-OH, Fmoc-AEEA-OH, Fmoc-AEEA-OH, Fmoc-Glu(α-OtBu)-OH and mono-tert-butyl octadecanedioate are successively coupled on the resin, Fmoc deprotected, washed with DCM

Example 3

Y-X$_1$-E-G-T-X$_2$-T-S-D-Y-X$_3$-I-X$_4$-L-D-K-Q-A-Q-A-E-F-V-
K-W-L-L-K-G-G-P-S-S-G-A-P-P-P-S-K;

wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{16}$—CO$_2$H; and the C-terminal amino acid is amidated as a C-terminal primary amide.

and dried to obtain the following P019 peptide-resin: Boc-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Gln(Trt)-Ala-Glu(OtBu)-Phe-Val-Lys (tBuO-Ste-γ-Glu(α-OtBu)-AEEA-AEEA-AEEA)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Rink-Linker-Nle-MBHA Resin.

The P019 peptide-resin is charged. 12-15 mL/g cleavage reagent for the peptide-resin (TFA:EDT:TIS:H$_2$O, 94:2:2:2 v/v) is added and reacted with stirring at 25±5° C. for 4 hours. The reaction mixture is filtered with a sand core funnel. The filtrate is collected. The resin is washed with a small amount of TFA three times, and the filtrates are combined and concentrated under reduced pressure. Methyl tert-butyl ether (MBTE) is added, and the resulting precipitate is washed with MBTE for 3 to 4 times, and dried by evaporating MBTE. The crude product is dried under reduced pressure at room temperature to constant weight to obtain the crude P019 product, which is subsequently purified and dried to obtain the P019 sample (the molecular weight determined by MS is 5142.0).

The above structure contains the standard single letter amino acid code with exception of residues Aib2, αMePhe6, Aib11, Aib13 and K24 where the structures of amino acid residues Aib2, αMePhe6, Aib11, Aib13 and K24 have been expanded.

Similar to the method described in Example 1 above, the peptide-resin intermediate 1 is used to carry out the preparation steps to synthesize the peptide of SEQ ID NO: 7 of the present invention (the molecular weight determined by MS is 4997.2). The difference is that the modification process with the modifying chain is sequentially coupling Fmoc-AEEA-OH, Fmoc-AEEA-OH, Fmoc-Glu(α-OtBu)-OH and mono-tert-butyl octadecanedioate on the resin. The resultant product is de-protected from Fmoc group, and washed with DCM to obtain P007 peptide-resin. Other steps are similar.

Example 4

Y-X$_1$-E-G-T-X$_2$-T-S-D-Y-X$_3$-I-X$_4$-L-D-K-Q-A-Q-A-E-F-V-
K-W-L-L-K-G-G-P-S-S-G-A-P-P-P-S-K;

wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{18}$—CO$_2$H; and the C-terminal amino acid is amidated as a C-terminal primary amide.

—W—L—L—K—G—G—P—S—S—G—A—P—P—P—S—K—NH₂

The above structure contains the standard single letter amino acid code with exception of residues Aib2, αMePhe6, Aib11, Aib13 and K24 where the structures of amino acid residues Aib2, αMePhe6, Aib11, Aib13 and K24 have been expanded.

wherein $X_1$ is Aib; $X_2$ is αMePhe; $X_3$ is Aib; $X_4$ is Aib; K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{20}$—CO$_2$H; and the C-terminal amino acid is amidated as a C-terminal primary amide.

—W—L—L—K—G—G—P—S—S—G—A—P—P—P—S—K—NH₂

Similar to the method described in Example 1 above, the peptide-resin intermediate 1 is used to carry out the preparation steps to synthesize the peptide of SEQ ID NO: 13 of the present invention (the molecular weight determined by MS is 5025.2). The difference is that the modification process with the modifying chain is sequentially coupling Fmoc-AEEA-OH, Fmoc-AEEA-OH, Fmoc-Glu(α-OtBu)-OH and eicosanedioic acid mono-tert-butyl ester on the resin. The resultant product is de-protected from Fmoc group, and washed with DCM to obtain P013 peptide-resin. Other steps are similar.

Example 5

Y-X₁-E-G-T-X₂-T-S-D-Y-X₃-I-X₄-L-D-K-Q-A-Q-A-E-F-V-K-W-L-L-K-G-G-P-S-S-G-A-P-P-P-S-K;

The above structure contains the standard single letter amino acid code with exception of residues Aib2, αMePhe6, Aib11, Aib13 and K24 where the structures of amino acid residues Aib2, αMePhe6, Aib11, Aib13 and K24 have been expanded.

Similar to the method described in Example 1 above, the peptide-resin intermediate 1 is used to carry out the preparation steps to synthesize the peptide of SEQ ID NO: 14 of the present invention (the molecular weight determined by MS is 5052.4). The difference is that the modification process with the modifying chain is sequentially coupling Fmoc-AEEA-OH, Fmoc-AEEA-OH, Fmoc-Glu(α-OtBu)-OH and docosanedioic acid mono-tert-butyl ester on the resin. The resultant product is de-protected from Fmoc group, and washed with DCM to obtain P014 peptide-resin. Other steps are similar.

Example 6

Y-X$_1$-E-G-T-X$_2$-T-S-D-Y-X$_3$-I-X$_4$-L-D-K-Q-A-Q-A-E-F-V-
K-W-L-L-K-G-G-P-S-S-G-A-P-P-P-S-K;    5 wherein X$_1$ is Aib; X$_2$ is αMePhe; X$_3$ is Aib; X$_4$ is Aib; K at position 24 is chemically modified through conjugation to the ε-amino of the K side-chain with ([2-(2-amino-ethoxy)-ethoxy]-acetyl) 3-(γ-Glu)$_1$-CO—(CH$_2$)$_{20}$—CO$_2$H; and the C-terminal amino acid is amidated as a C-terminal primary amide.

The above structure contains the standard single letter amino acid code with exception of residues Aib2, αMePhe6, Aib11, Aib13 and K24 where the structures of amino acid residues Aib2, αMePhe6, Aib11, Aib13 and K24 have been expanded.

Similar to the method described in Example 1 above, the peptide-resin intermediate 1 is used to carry out the preparation steps to synthesize the peptide of SEQ ID NO: 16 of the present invention (the molecular weight determined by MS is 5198.0). The difference is that the modification process with the modifying chain is sequentially coupling Fmoc-AEEA-OH, Fmoc-AEEA-OH, Fmoc-AEEA-OH, Fmoc-Glu(α-OtBu)-OH and docosanedioic acid mono-tert-butyl ester on the resin. The resultant product is de-protected from Fmoc group, and washed with DCM to obtain P016 peptide-resin. Other steps are similar.

Example 7

Y-X$_1$-E-G-T-X$_2$-T-S-D-Y-X$_3$-I-X$_4$-L-D-K-Q-A-Q-A-E-F-V-
K-W-L-L-K-G-G-P-S-S-G-A-P-P-P-S-K;

wherein X$_1$ is Aib; X$_2$ is αMePhe; X$_3$ is Aib; X$_4$ is Aib; K at position 28 are chemically modified through conjugation to the ε-aminos of the K side-chains with ([2-(2-amino-ethoxy)-ethoxy]-acetyl)$_2$-(γ-Glu)$_1$-CO—(CH$_2$)$_{16}$—CO$_2$H; and the C-terminal amino acid is amidated as a C-terminal primary amide.

The above structure contains the standard single letter amino acid code with exception of residues Aib2, αMePhe6, Aib11, Aib13 and K28 where the structures of amino acid residues Aib2, αMePhe6, Aib11, Aib13 and K28 have been expanded.

Similar to the method described in Example 2 above, the peptide-resin intermediate 2 is used to carry out the preparation steps to synthesize the peptide of SEQ ID NO: 8 of the present invention (the molecular weight determined by MS is 4996.8). The difference is that the modification process with the modifying chain is sequentially coupling Fmoc-AEEA-OH, Fmoc-AEEA-OH, Fmoc-Glu(α-OtBu)-OH and mono-tert-butyl octadecanedioate on the resin. The resultant product is de-protected from Fmoc group, and washed with DCM to obtain P008 peptide-resin. Other steps are similar.

Example 8

Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K;

wherein X$_1$ is Aib; X$_2$ is αMePhe; X$_3$ is Aib; X$_4$ is Aib; K at position 28 are chemically modified through conjugation to the ε-aminos of the K side-chains with ([2-(2-amino-ethoxy)-ethoxy]-acetyl)$_2$-(γ-Glu)$_1$-CO—(CH$_2$)$_{20}$—CO$_2$H; and the C-terminal amino acid is amidated as a C-terminal primary amide.

The above structure contains the standard single letter amino acid code with exception of residues Aib2, αMePhe6, Aib11, Aib13 and K28 where the structures of amino acid residues Aib2, αMePhe6, Aib11, Aib13 and K28 have been expanded.

Similar to the method described in Example 2 above, the peptide-resin intermediate 2 is used to carry out the preparation steps to synthesize the peptide of SEQ ID NO: 17 of the present invention (the molecular weight determined by MS is 5052.8). The difference is that the modification process with the modifying chain is sequentially coupling Fmoc-AEEA-OH, Fmoc-AEEA-OH, Fmoc-Glu(α-OtBu)-OH and docosanedioic acid mono-tert-butyl ester on the resin. The resultant product is de-protected from Fmoc group, and washed with DCM to obtain P017 peptide-resin. Other steps are similar.

Example 9

Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K;

wherein X$_1$ is Aib; X$_2$ is αMePhe; X$_3$ is Aib; X$_4$ is Aib; K at position 28 are chemically modified through conjugation to the ε-aminos of the K side-chains with ([2-(2-amino-ethoxy)-ethoxy]-acetyl)$_2$-(γ-Glu)$_3$-CO—(CH$_2$)$_{16}$—CO$_2$H; and the C-terminal amino acid is amidated as a C-terminal primary amide.

The above structure contains the standard single letter amino acid code with exception of residues Aib2, αMePhe6, Aib11, Aib13 and K28 where the structures of amino acid residues Aib2, αMePhe6, Aib11, Aib13 and K28 have been expanded.

Similar to the method described in Example 2 above, the peptide-resin intermediate 2 is used to carry out the preparation steps to synthesize the peptide of SEQ ID NO: 18 of the present invention (the molecular weight determined by MS is 5255.2). The difference is that the modification process with the modifying chain is sequentially coupling Fmoc-AEEA-OH, Fmoc-AEEA-OH, Fmoc-Glu(α-OtBu)-OH, Fmoc-Glu(α-OtBu)-OH, Fmoc-Glu(α-OtBu)-OH and mono-tert-butyl octadecanedioate on the resin. The resultant product is de-protected from Fmoc group, and washed with DCM to obtain P018 peptide-resin. Other steps are similar.

Example 10

Y-X₁-E-G-T-X₂-T-S-D-Y-X₃-I-X₄-L-D-K-Q-A-Q-A-E-F-V-
K-W-L-L-K-G-G-P-S-S-G-A-P-P-P-S-K;

wherein $X_1$ is Aib; $X_2$ is αMePhe; $X_3$ is Aib; $X_4$ is Aib; K at position 28 are chemically modified through conjugation to the ε-aminos of the K side-chains with ([2-(2-amino-ethoxy)-ethoxy]-acetyl) 3-(γ-Glu)₁-CO—(CH₂)₂₀—CO₂H; and the C-terminal amino acid is amidated as a C-terminal primary amide.

The above structure contains the standard single letter amino acid code with exception of residues Aib2, αMePhe6, Aib11, Aib13 and K28 where the structures of amino acid residues Aib2, αMePhe6, Aib11, Aib13 and K28 have been expanded.

Similar to the method described in Example 2 above, the peptide-resin intermediate 2 is used to carry out the preparation steps to synthesize the peptide of SEQ ID NO: 20 of the present invention (the molecular weight determined by MS is 5198.4). The difference is that the modification process with the modifying chain is sequentially coupling Fmoc-AEEA-OH, Fmoc-AEEA-OH, Fmoc-AEEA-OH, Fmoc-Glu(α-OtBu)-OH and docosanedioic acid ester mono-tert-butyl on the resin. The resultant product is de-protected from Fmoc group, and washed with DCM to obtain P020 peptide-resin. Other steps are similar.

In some embodiments of the present invention, as for the preparation of the peptide-resin intermediate 3 (a peptide-resin intermediate wherein the modifying chain is bonded to the Lys at position 16), that is Boc-Tyr(tBu)-Aib-Glu (OtBu)-Gly-Thr(tBu)-αMePhe-Thr(tBu)-Ser(tBu)-Asp (OtBu)-Tyr(tBu)-Aib-Ile-Aib-Leu-Asp(OtBu)-Lys-Gln (Trt)-Ala-Gln(Trt)-Ala-Glu(OtBu)-Phe-Val-Lys(Boc)-Trp (Boc)-Leu-Leu-Lys(Boc)- Gly-Gly-Pro-Ser(tBu)-Ser(tBu)-Gly-Ala-Pro-Pro-Pro-Ser(tBu)-Lys(Boc)-Rink Linker-Nle-MBHA Resin, the preparation method for peptide-resin intermediate 1 in Example 1 is referred to.

As for the preparation of the peptide-resin intermediate 4 (a peptide-resin intermediate wherein the modifying chain is bonded to the Lys at position 40), that is Boc-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Gln(Trt)-Ala-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys-Rink Linker-Nle-MBHA Resin, the preparation method for peptide-resin intermediate 1 in Example 1 is referred to.

Other dual agonist compounds in the present invention can be prepared according to the methods described above.

Related Assays

Provided below are the conditions and data in several assays for Examples.

I. In Vitro Function (I) In Vitro Binding Activity to Human GIP-1 and GIP Receptors The in vitro binding potency of compounds according to the present invention to human GIP and GLP-1 receptors is evaluated by measuring the binding affinities Ki, using crude cellular membranes obtained from clonal cell lines over-expressing either the human GLPIR cDNA or human GIP-R cDNA.

1) In Vitro Binding Activity to Human GLP-1 Receptor hGLP-1 and the compound of the present invention are dissolved in DMSO and stored at $-80°$ C. 89 μL of membrane dissolved in binding buffer (50 mM Hepes, pH 7.4, 5 mM $MgCl_2$, 5 mM EDTA, 0.005% TWEEN, 0.005% HSA) is transferred to a 96-well test plate (5 μg/well). The compound is serially diluted in DMSO, and then, 1 μL of the diluted compound or 100% DMSO is added to the test plate containing the membrane solution. 10 μL of [$^{125}$I] GLP-1 is further added (the final concentration in the reaction is 0.15 nM). The test plate is left at room temperature for 90 minutes. The membrane complexes are harvested into a GF/B plate pre-coated with 0.5% PEI by using a Cell Harvester, and washed for 3 times with 500 μL of pre-cooled elution buffer (50 mM Hepes, pH 7.4, 500 mM NaCl) at 4° C. After drying at 37° C. for 2 hours, 50 μL of scintillation fluid is added to each well. The plate is read with a MicroBeta2 scintillation counter after sealing and settling for at least 1 hour so as to determine the membrane bound radioligand level.

The absolute $IC_{50}$ concentration of the compound is derived by non-linear regression of the binding percent of [$^{125}$I] GLP-1 versus the concentration of the compound added. The $IC_{50}$ concentration is converted to Ki (Ki is the inhibition constant) using the Cheng-Prusoff equation.

2) In Vitro Binding Activity to Human GIP Receptor hGIP and the compound of the present invention are dissolved in DMSO and stored at $-80°$ C. 98 μL of membrane dissolved in binding buffer (50 mM HEPES pH 7.4, 5 mM $MgCl_2$, 1 mM $CaCl_2$, 0.1% BSA, 0.005% Tween-20) is transferred to a 96-well test plate (15 μg/well). The compound is serially diluted in DMSO, and then, 2 μL of the diluted compounds or 100% DMSO is added to the test plate containing the membrane solution. 100 μL of [$^{125}$I] GIP is further added (the final concentration in the reaction is 0.0315 nM). The test plate is left at room temperature for 90 minutes. The membrane complexes are harvested into a GF/B plate pre-coated with 0.5% PEI by using a Cell Harvester, and washed for 3 times with 500 μL of pre-cooled elution buffer (50 mM Tris-HCl pH 7.4, 125 mM NaCl) at 4° C. After drying at 37° C. for 2 hours, 50 μL of scintillation fluid is added to each well. The plate is read with a MicroBeta2 scintillation counter after sealing and settling for at least 1 hour so as to determine the membrane bound radioligand level.

The absolute $IC_{50}$ concentration of the compound is derived by non-linear regression of the binding percent of [$^{125}$I] GIP versus the concentration of the compound added. The $IC_{50}$ concentration is converted to Ki (Ki is the inhibition constant) using the Cheng-Prusoff equation.

TABLE 1

| Receptor Binding Affinity, Ki Ratio | | |
|---|---|---|
| Compound | GLP-1R Ki ratio | GIPR Ki ratio |
| GLP-1 | 1.00 | NA |
| GIP | NA | 1.00 |
| P001 | 19.52 | 8.82 |
| Tirzepatide | 0.28 | 0.06 |
| P007 | 0.47 | NA |
| P008 | 1.09 | 0.16 |
| P013 | 0.28 | 0.14 |
| P014 | 0.37 | 0.08 |
| P015 | 0.17 | NA |
| P016 | 0.63 | 0.11 |
| P017 | 0.56 | 0.04 |
| P018 | 1.45 | 0.05 |
| P019 | 0.93 | 0.09 |
| P020 | 1.36 | 0.05 |

NA: not detected

Ki ratio: the ratio of the Ki value of the endogenous ligand to the Ki value of the test compound The binding affinities of all compounds to the receptors are expressed by Ki ratios, and a larger Ki ratio of the compound indicates a stronger binding affinity. As compared with P001, the binding affinities of the compounds according to the present invention to both human GLP-1R and GIPR are decreased to a certain extent (see Table 1).

As compared with Tirzepatide, the binding affinities of the other 9 compounds according to the present invention, except for P015, to human GLP-IR are slightly stronger than that of Tirzepatide. In addition, the binding affinities of the five compounds, namely, P008, P013, P014, P016 and P019, to GIPR are also slightly stronger than that of Tirzepatide (see Table 1).

To sum up, the binding affinities to human GLP-1R and GIPR of the compounds with different modifying chains according to the present invention are lower than that of P001 in some degree, but are slightly stronger than or equivalent to that of Tirzepatide.

(II) Agonistic Activity on hGLP-1R and hGIPR

For compounds according to the present invention, the in vitro functional activities on human GIP and GLP-1 receptors are determined in HEK-293 clonal cell lines expressing these receptors.

1) Agonistic Activity on Human GLP-1 Receptor (CAMP Reporter Gene Assay)

The agonistic activities of the compounds according to the present invention on human GLP-1R are determined by cAMP reporter gene assay, and P001, Tirzepatide and endogenous ligand GLP-1 are used as references.

HEK293/CRE/GLP-1R cells are inoculated in a 96-well plate at 50,000 cells/well (80 μL/well), and incubated overnight in a 37° C., 5% $CO_2$ incubator. 20 μL/well of the test medium (DMEM containing 0.1% casein) containing a compound (the compound according to the present invention, P001, Tirzepatide or GLP-1) is added to the 96-well plate, and continued to incubate in a 37° C., 5% $CO_2$ incubator for 6 hours and equilibrated to room temperature. The supernatant is removed. 50 μL/well Bright-Glo reagent is added, shaked and lysed at room temperature for 10 minutes. The luminescence is read using an Envision microplate reader, and the luciferase activity is measured.

The response value to 100 nM GLP-1 is set as 100% response value, and GraphPad is used to perform nonlinear regression according to the response percentage and the concentration of the compound added to obtain the $EC_{50}$ value for each compound.

2) Agonistic Activity on Human GIP Receptor (LANCE Ultra cAMP Assay)

The agonistic activities of the compounds according to the present invention on human GIPR are determined by a LANCE Ultra CAMP Kit, and P001, Tirzepatide and endogenous ligand GIP are used as references.

The in vitro agonistic activities of the compounds according to the present invention on GIPR is determined in HEK293 cells stably expressing human GIPR (HEK293/GIPR cells). HEK293/GIPR cells are formulated in HBSS buffer (0.1% Casein, 500 μM IBMX, 5 mM HEPES), and inoculated into a 384-well cell culture plate at 1000 cells/well (5 μL/well). 5 μL of HBSS buffer containing 2× compounds is added to the above-mentioned 384-well cell culture plate. After been sealed, the plate is placed into a 37° C., 5% $CO_2$ incubator for about 30 minutes. After the incubation is completed, 5 μL of cAMP-Eu working solution and 5 μL of CAMP-Ulight working solution are added sequentially, and the plate is shaken for uniform mixing. The incubation is performed for 1 hour at 25° C. The signal values at 665 nm and 615 nm are read on an Envision microplate reader. The ratio of the signal value at 665 nm to the signal value at 615 is calculated, and converted into a cAMP concentration by using the cAMP standard curve. The response value to 1 μM GIP is set as 100% response value, and GraphPad is used to perform nonlinear regression according to the response percentage and the concentration of the compound added to obtain the $EC_{50}$ value for each compound.

TABLE 2

Agonist Activity on Human GLP-1 and GIP Receptors, $EC_{50}$ Values

| Compound | GLP-1R $EC_{50}$ value | GIPR $EC_{50}$ value |
|---|---|---|
| GLP-1 | 1.00 | NA |
| GIP | NA | 1.00 |
| P001 | 52.09 | 7.13 |
| Tirzepatide | 0.74 | 0.51 |
| P007 | 5.84 | 1.15 |
| P008 | 4.79 | 1.67 |
| P013 | 2.41 | 0.86 |
| P014 | 1.73 | 0.25 |
| P015 | 2.44 | 0.17 |
| P016 | 1.56 | 0.56 |
| P017 | 1.35 | 0.16 |
| P018 | 3.63 | 2.55 |
| P019 | 4.95 | 1.68 |
| P020 | 1.41 | 0.22 |

NA: not detected
$EC_{50}$ value: the ratio of the $EC_{50}$ value of the endogenous ligand to the $EC_{50}$ value of the test compound The agonistic activity of all compounds against human GLP-1 and GIP receptors is expressed by $EC_{50}$ value, and the larger the $EC_{50}$ value, the stronger the activity of the compound. As compared with P001, the compound according to the present invention shows a certain degree of decrease in the agonistic activity on human GLP-1R and GIPR (see Table 2).

As compared with Tirzepatide, all compounds according to the present invention have stronger agonistic activity on human GLP-1R. In addition, the agonistic activity of the six compounds, namely, P007, P008, P013, P016, P018 and P019, on human GIPR is also slightly stronger than that of Tirzepatide (see Table 2).

To sum up, the agonistic activity on human GLP-1R and GIPR of the compounds with different modifying chains according to the present invention is lower than that of P001 in some degree, but 6 compounds according to the present invention are stronger than Tirzepatide in terms of agonistic activity on human GLP-1R and GIPR.

As shown by in vitro function assay, since the 10 compounds according to the present invention do not differ significantly in activity, the compounds are further screened using a single administration hypoglycaemic assay in db/db mice.

(III) Agonistic Activity on GLP-1R and GIPR of Different Species

For human, cat, dog, mouse, rat, rabbit, and monkey GLP-1 and GIP receptors, the in vitro functional activities of the compounds according to the present invention on these receptors were determined in cells stably expressing these receptors and in CHO-K1 cells transiently transfecting these receptors.

1) Agonistic Activity on Human, Dog, Mouse, Rat, Rabbit, and Monkey GLP-1 Receptors (LANCE Ultra cAMP Assay)

The LANCE Ultra CAMP Kit was used to determine the agonistic activity of the compound of the present invention on human, dog, mouse, rat, rabbit, and monkey GLP-IR, and the endogenous ligand GLP-1 was used as a reference.

The in vitro agonistic activity of the compound of the present invention on GLP-IR was measured in cells stably expressing human, dog, mouse, rat, rabbit, and monkey GLP-1R (human GLP-1R-HEK, dog GLP-1R-HEK, mouse GLP-1R-HEK, rat GLP-1R- in HEK, rabbit GLP-1R-CHO, monkey GLP-1R-HEK cells). Human GLP-1R-HEK, dog GLP-1R-HEK, mouse GLP-1R-HEK, rat GLP-1R-HEK, rabbit GLP-1R-CHO, and monkey GLP-1R-HEK cells were resuspended in 1×Casein Stimulation Buffer (HBSS, 5 mM HEPES, 0.5 mM IBMX, 0.1% casein, pH7.4), and seeded into a 384-well cell culture plate at 9 μL/well (cell numbers being 1000, 1000, 1000, 1500, 1000, 1000 cells/well, respectively). 1 μL of 1×Casein Stimulation Buffer containing 10×compound was added to the above-mentioned 384-well cell culture plate. The plate is incubated at 37° C. for 30 minutes. After the incubation was completed, 5 μL of Eu-CAMP working solution and 5 μL of Ulight™-CAMP working solution were added sequentially, centrifuged and then incubated at room temperature for 1 hour. The readings at 665 nm and 620 nm were determined with a 330 nm excitation light on a microplate reader. The 665 nm/620 nm reading ratio was calculated. The response value at the maximum concentration of GLP-1 was set as 100% response value. GraphPad was used to perform nonlinear regression according to the response percentage and the concentration of the compound added to obtain the $EC_{50}$ value for each compound.

2) Agonistic Activity on Human, Dog, Mouse, Rat, Rabbit, and Monkey GIP Receptors (LANCE Ultra cAMP Assay)

The LANCE Ultra CAMP Kit was used to determine the agonistic activity of the compound of the present invention on human, dog, mouse, rat, rabbit, and monkey GIPR, and the endogenous ligand GIP was used as a reference.

CHO-K1 cells were seeded in a 6-well plate at 0.6× 106 cells/well and incubated overnight in an incubator at a temperature of 37° C. and a carbon dioxide concentration of 5%. The next day, CHO-K1 cell media were replaced. Then two tubes A and B were prepared for each plasmid. 100 μL Opti-MEM is added to tube A, then 4 μL Lipofectamine™ 3000 was added and mixed uniformly. 100 μL Opti-MEM was firstly added to tube B, then 2 μg of one of the plasmids (human GIPR-pcDNA5 (+) plasmid, dog GIPR-pcDNA5 (+) plasmid, mouse GIPR-pcDNA5 (+) plasmid, rat GIPR-pcDNA5 (+) plasmid, rabbit GIPR-pcDNA5 (+) plasmid, monkey GIPR-pcDNA5 (+) plasmid) was added and mixed uniformly, and 4 μL P3000™ was added to tube B and mixed uniformly (the ratio of plasmid to transfection reagent was 1 μg: 2 μL). The diluted solution in tube A was added to the diluted solution in tube B, mixed evenly, and incubated at room temperature for 15 minutes. Finally, the mixture was gently added to the cells whose media had been replaced, shaked gently to mix, and then incubated overnight in an incubator at a temperature of 37° C. and a carbon dioxide concentration of 5%. Cells were used for compound functional activity assay 18-20 hours after transfection.

18-20 hours after transfection, human GIPR-CHO, dog GIPR-CHO, mouse GIPR-CHO, rat GIPR-CHO, rabbit GIPR-CHO, and monkey GIPR-CHO cells were resuspended in 1×Casein Stimulation Buffer (HBSS, 5 mM HEPES, 0.5 mM IBMX, 0.1% casein, pH7.4), and seeded into a 384-well cell culture plate at 9 μL/well (cell numbers being 1000, 2000, 2000, 2000, 2000, 2000 cells/well, respectively). 1 μL of 1×Casein Stimulation Buffer containing 10× compound was added to the above-mentioned 384-well cell culture plate. The plate was incubated at 37° C. for 30 minutes. After the incubation is completed, 5 μL of Eu-CAMP working solution and 5 μL of Ulight™-CAMP working solution were added sequentially, centrifuged and then incubated at room temperature for 1 hour. The readings at 665 nm and 620 nm were determined with a 330 nm excitation light on a microplate reader. The 665 nm/620 nm reading ratio was calculated. The response value of the maximum concentration of GIP was set as 100% response value. GraphPad was used to perform nonlinear regression according to the response percentage and the concentration of the compound added to obtain the $EC_{50}$ value for each compound.

For human and cat GLP-1 and GIP receptors, the in vitro functional activities of the compounds according to the present invention on these receptors were determined in CHO cells transiently transfecting these receptors.

3) Agonistic Activity on Human and Cat GLP-1 and GIP Receptors (LANCE Ultra CAMP Assay)

The LANCE Ultra CAMP Kit was used to determine the agonistic activity of the compound of the present invention against human and cat GLP-1 and GIP receptors, and the endogenous ligands GLP-1R and GIP were used as references.

CHO-K1 cells were seeded in a 6-well plate at 0.6× 106 cells/well and incubated overnight in an incubator at a temperature of 37° C. and a carbon dioxide concentration of 5%. The next day, CHO-K1 cell media were replaced. Then two tubes A and B were prepared for each plasmid. 100 μL Opti-MEM was added to tube A, then 4 μL Lipofectamine™ 3000 was added and mixed uniformly. 100 μL Opti-MEM was firstly added to tube B, then 2 μg of one of the plasmids (human GLP-IR-pcDNA5 (+) plasmid, cat GLP-IR-pcDNA5 (+) plasmid, human GIPR-pcDNA5 (+) plasmid, cat GIPR-pcDNA5 (+) plasmid) was added and mixed uniformly, and 4 μL P3000™ was added to tube B and mixed uniformly (the ratio of plasmid to transfection reagent is 1 μg: 2 μL). The diluted solution in tube A was added to the diluted solution in tube B, mixed evenly, and incubated at room temperature for 15 minutes. Finally, the mixture was gently added to the cells whose media had been replaced, shaked gently to mix, and then incubated overnight in an incubator at a temperature of 37° C. and a carbon dioxide concentration of 5%. Cells were used for compound functional activity assay 18-20 hours after transfection.

18-20 hours after transfection, human GLP-1R-CHO, cat GLP-1R-CHO, human GIPR-CHO, cat GIPR-CHO cells were resuspended in 1×Casein Stimulation Buffer (HBSS, 5 mM HEPES, 0.5 mM IBMX, 0.1% casein, pH7.4), and seeded into a 384-well cell culture plate at 9 μL/well (cell numbers being 2000, 2000, 1000, 2000 cells/well, respectively). 1 μL of 1×Casein Stimulation Buffer containing 10× compound was added to the above-mentioned 384-well cell culture plate. The plate was incubated at 37° C. for 30 minutes. After the incubation was completed, 5 μL of Eu-cAMP working solution and 5 μL of Ulight™-CAMP working solution were added sequentially, centrifuged and then incubated at room temperature for 1 hour. The readings at 665 nm and 620 nm were determined with a 330 nm excitation light on a microplate reader. The 665 nm/620 nm reading ratio was calculated. The response value of the maximum concentration of GLP-1R or GIP was set as 100% response value. GraphPad was used to perform nonlinear regression according to the response percentage and the concentration of the compound added to obtain the $EC_{50}$ value for each compound.

TABLE 3

| Agonistic activity on GLP-1Rs and GIPRs of different species, $EC_{50}$ ratio | | | | | | | |
|---|---|---|---|---|---|---|---|
| Compound | Human | Cat | Dog | Mouse | Rat | Rabbit | Monkey |
| GLP-1R $EC_{50}$ ratio | | | | | | | |
| GLP-1 | 1.00 | 1.09 | 4.09 | 3.22 | 8.04 | 2.53 | 2.19 |
| P016 | 1.00 | 2.98 | 4.52 | 1.09 | 1.59 | 1.05 | 2.66 |
| Tirzepatide | 1.00 | 31.4 | 84.84 | 0.57 | 1.21 | 0.68 | 3.31 |
| GIPR $EC_{50}$ ratio | | | | | | | |
| GIP | 1.00 | 5.61 | 5.58 | 68.74 | 2.38 | 7.18 | 14.38 |
| P016 | 1.00 | 3.59 | 2.88 | 12.49 | 2.22 | 5.34 | 5.77 |
| Tirzepatide | 1.00 | 8.05 | 6.13 | 220.87 | 9.53 | 16.04 | 7.38 |

$EC_{50}$ value: the ratio of $EC_{50}$ value of other species to human $EC_{50}$ value The agonistic activities of all compounds on GLP-1 receptors and GIP receptors are expressed as the $EC_{50}$ ratio. The smaller the $EC_{50}$ value, the stronger the activity of the compound.

Compared with the agonistic activity on human receptors, the agonistic activities of compound P016 according to the present invention on mouse, rat, rabbit, cat and monkey GLP-1R were comparable to its agonistic activity on human GLP-1R, and the agonistic activity on dog GLP-1R is slightly weaker (4.52 times weaker). The agonistic activities of P016 on rat and dog GIPR were comparable to that on human GIPR, and the agonistic activities on cat, rabbit, monkey, and mouse GIPR are slightly weaker (3.59, 5.34, 5.77 and 12.49 times weaker, respectively). The agonistic activities of Tirzepatide on mouse, rat, rabbit and monkey GLP-1Rs were comparable to that on human GLP-1R, but its agonistic activities on cat and dog GLP-1Rs were >30 times or >80 times weaker than that on human GLP-1R (i.e., agonistic activity being less than 1/30 or less than 1/80). Tirzepatide's agonistic activities on dog, monkey, cat, rat and rabbit GIPR were slightly weaker than that on human GIPR (6.13, 7.38, 8.05, 9.53 and 16.04 times weaker, respectively). Tirzepatide's agonistic activity on mouse GIPR was >220 times weaker than that on human GIPR (i.e., agonistic activity was less than $1/220$) (see Table 3). In summary, the compound of the present invention has strong agonistic activities on cat, dog, mouse, rat, rabbit and monkey GLP-IR and GIPR, which are comparable to the agonistic activities on human GLP-1R and GIPR (1.05~12.5 times weaker). It can be seen that cats, dogs, mice, rats, rabbits and monkeys are non-human relevant species of the compound of the present invention. The agonistic activities of Tirzepatide on the tested species vary greatly, especially the agonistic activities of Tirzepatide on cat and dog GLP-1R are much weaker than its agonistic activity on human GLP-1R.

4) Sequence Alignment of GLP-1R and GIPR of Different Species

GLP-1R/GIPR of cat, dog, mouse, rat, rabbit, monkey, pig, alpaca, horse, sheep, and bovine are compared with sequences of human GLP-1R/GIPR by using NCBI (National Center for Biotechnology Information) BLAST. It is found that the homology between GLP-1R/GIPR of these species and human GLP-1R/GIPR is >80%. Combining the results in Table 3, it is predicted that the agonistic effects of the compound of the present invention on the GLP-1R/GIPR of pig, alpaca, horse, sheep, and bovine are comparable to or slightly weaker than that on human GLP-1R/GIPR. It is speculated that the compound of the present invention has a therapeutic function on type II diabetes melitus, obesity and other related diseases in animals of these species.

TABLE 4

Homology alignment result of GLP-1R and GIPR of different species with human GLP-1R/GIPR

|  | Human | Cat | Dog | Mouse | Rat | Rabbit |
|---|---|---|---|---|---|---|
| GLP-1R | 100% | 92.22% | 89.60% | 92.01% | 90.93% | 92.44% |
| GIPR | 100% | 85.44% | 88.76% | 80.98% | 80.98% | 92.44% |

|  | Cynomolgus Monkey | pig | alpaca | horse | sheep | bovine |
|---|---|---|---|---|---|---|
| GLP-1R | 98.06% | 93.09% | 91.76% | 90.93% | 91.36% 84.02% | 91.36% |
| GIPR | 97.42% | 81.89% 87.61% 90.61% | 84.88% | 89.19% | 81.89% | 81.68% 81.68% 87.39% 84.23% |

Note:
sheep GLP-1R, pig GIPR, and bovine GIPR have 2, 3 and 4 transcripts, respectively.

II. Pharmacokinetics (I) Pharmacokinetics Following Single Administration in SD Rat After subcutaneous (s.c.) or intravenous (i.v.) administration to SD rats, plasma is collected and the concentration of the drug in plasma is detected to demonstrate the in vivo pharmacokinetic properties of the compound according to the present invention. The compound is dissolved in a phosphate buffer, and filtered through a membrane filter (PTFE, 0.45 μm) to obtain a 25 nmol/mL solution of the compound. The compound is administrated to male SD rats (230-268 g, n=3) at a dose of 50.0 nmol/kg (s.c.) or 25.0 nmol/kg (i.v.). About 150 μL of whole blood is collected from the internal jugular vein into an EDTA-K2 anticoagulant tube at predose, 0.0833 (only for i.v.), 0.25, 0.5, 1, 2, 4, 6, 8, 24, 48, 72, 96 and 120 hours respectively. The blood samples are centrifuged at 1500 g for 10 minutes to obtain plasma, which is stored at −90° C. to −60° C. for further analysis and assay.

Sample Treatment (1) Method for Treating the Samples for Tirzepatide, P007, P008, P013 and P014

30.0 μL of thawed plasma sample is taken. 150 μL of acetonitrile solution (containing 5 ng mL$^{-1}$ Verapamil, 50 ng·mL$^{-1}$ Glibenclamide, 200 ng·mL$^{-1}$ Tolbutamide and 200 ng·mL$^{-1}$ Diclofenac) are added to precipitate protein. The mixture is vortexed for 5 minutes, and centrifuged at 3700 rpm for 8 minutes. 70.0 μL of the supernatant is taken, into which 70.0 μL of 0.5% aqueous formic acid solution is added. The mixture is vortexed for 5 minutes. 15 μL of the mixture solution is sampled and injected into the LC-MS/MS to determine the drug concentration in plasma.

(2) Method for Treating the Samples for P015, P016, P017 and P018

20.0 μL of thawed plasma sample is taken. 60 μL of acetonitrile solution (containing 5 ng mL$^{-1}$ Verapamil, 50 ng·mL$^{-1}$ Glibenclamide, 200 ng·mL$^{-1}$ Tolbutamide and 200 ng·mL$^{-1}$ Diclofenac) are added to precipitate protein. The mixture is vortexed for 1 minute, and centrifuged at 13000 rpm for 8 minutes. 60.0 μL of the supernatant is taken, into which 60.0 μL of 0.5% aqueous formic acid solution is added. The mixture is vortexed for 10 minutes. 10.0 μL of the mixture solution is sampled and injected into the LC-MS/MS to determine the drug concentration in plasma.

(3) Method for Treating the Samples for P019 and P020

30.0 μL of thawed plasma sample is taken. 150 μL of acetonitrile solution (containing 5 ng mL$^{-1}$ Verapamil, 50 ng mL$^{-1}$ Glibenclamide, 200 ng·mL$^{-1}$ Tolbutamide and 200 ng·mL$^{-1}$ Diclofenac) are added to precipitate protein. The mixture is vortexed for 5 minutes, and centrifuged at 3700 rpm for 8 minutes. 70.0 μL of the supernatant is taken, into which 70.0 μL of 0.5% aqueous formic acid solution is added. The mixture is vortexed for 5 minutes. 10.0 μL of the mixture solution is sampled and injected into the LC-MS/MS to determine the drug concentration in plasma.

Based on the drug concentration in plasma of the compounds in SD rats, the pharmacokinetic parameters are calculated by applying the software Winnolin 8.2 in a non-compartmental model, and the results are shown in Table 5 and Table 6 below.

TABLE 5

Pharmacokinetic Parameters after Subcutaneous Injection of Different Polypeptide Compounds to Rats

| PK parameters | Unit | Tirzepatide | P007 | P008 | P013 | P014 |
|---|---|---|---|---|---|---|
| Dosage | nmol/kg | 50 | 50 | 50 | 50 | 50 |
| $T_{1/2}$ | h | 11.4 ± 1.79 | 15.0 ± 2.89 | 18.7 ± 4.82 | 15.0 ± 0.737 | 14.8 ± 0.503 |
| $T_{max}$ | h | 7.33 ± 1.15 | 7.33 ± 1.15 | 13.3 ± 9.24 | 24.0 ± 0 | 24.0 ± 0 |
| $C_{max}$ | nM | 128 ± 42.8 | 169 ± 14.7 | 149 ± 20.5 | 142 ± 28.2 | 170 ± 16.4 |
| $AUC_{0-t}$ | nM · h | 3610 ± 1200 | 6150 ± 776 | 5400 ± 1030 | 5740 ± 1070 | 6230 ± 651 |
| $AUC_{0-inf}$ | nM · h | 3670 ± 1190 | 6630 ± 439 | 6680 | 6080 ± 1180 | 6620 ± 712 |

TABLE 5-continued

Pharmacokinetic Parameters after Subcutaneous
Injection of Different Polypeptide Compounds to Rats

| PK parameters | Unit | Tirzepatide | P007 | P008 | P013 | P014 |
|---|---|---|---|---|---|---|
| $MRT_{0-t}$ | h | 19.0 ± 0.265 | 21.4 ± 1.87 | 21.0 ± 1.85 | 26.2 ± 0.700 | 26.2 ± 0.781 |
| $MRT_{0-inf}$ | h | 20.3 ± 0.755 | 25.7 ± 1.69 | 25.4 | 29.9 ± 1.33 | 30.0 ± 1.01 |

TABLE 6

Pharmacokinetic Parameters after Subcutaneous Injection of Different Polypeptide Compounds to Rats

| PK parameters | Unit | P015 | P016 | P017 | P018 | P019 | P020 |
|---|---|---|---|---|---|---|---|
| Dosage | nmol/kg | 50 | 50 | 50 | 50 | 50 | 50 |
| $T_{1/2}$ | h | 16.1 ± 1.21 | 14.1 ± 0.153 | 18.7 ± 2.69 | 18.3 ± 6.77 | 10.9 ± 1.92 | 17.9 ± 0.57 |
| $T_{max}$ | h | 24.0 ± 0 | 24.0 ± 0 | 24.0 ± 0 | 24.0 ± 0 | 13.3 ± 9.24 | 24.0 ± 0 |
| $C_{max}$ | nM | 213 ± 21.3 | 119 ± 7.00 | 112 ± 15.5 | 175 ± 45.1 | 302 ± 89.9 | 139 ± 28.1 |
| $AUC_{0-t}$ | nM · h | 8830 ± 862 | 4840 ± 270 | 4190 ± 242 | 7490 ± 1360 | 7910 ± 545 | 5620 ± 1690 |
| $AUC_{0-inf}$ | nM · h | 9490 ± 1090 | 5070 ± 262 | 4530 ± 28.28 | 7940 ± 1230 | 8630 ± 601 | 7070 ± 28.3 |
| $MRT_{0-t}$ | h | 26.8 ± 0.557 | 28.1 ± 1.12 | 27.9 ± 2.99 | 28.5 ± 4.45 | 17.1 ± 2.55 | 29.5 ± 4.68 |
| $MRT_{0-inf}$ | h | 31.4 ± 1.35 | 31.1 ± 1.00 | 36.9 ± 3.46 | 33.4 ± 7.00 | 18.3 ± 2.76 | 37.1 ± 0.636 |

The pharmacokinetics study on rats by subcutaneously injecting the compounds according to the present invention shows that: the half-life of P007, P008, P013, P014, P015, P016, P017, P018 and P020 are greater than the half-life of Tirzepatide (increased by about 23.7% to 64.0%). As compared with Tirzepatide, a commercially available dual-target product, the compounds according to the present invention modified by the modifying chain can provide a longer half-life in plasma. In addition, as compared with P001, the compound according to the present invention has a substantially longer half-life. The half-life is prolonged by more than 15 times, more than 20 times, or even more than 30 times.

(II) Pharmacokinetics in C57 Mice

After subcutaneous or intravenous administration to C57 mice, plasma is collected and the drug concentration in plasma is determined to illustrate the in vivo pharmacokinetic properties of the compound according to the present invention. The compound is dissolved in a phosphate buffer containing 0.1% Tween 20, and filtered through a filter membrane (PTFE, 0.45 µm) to obtain a 15 nmol/mL compound solution. About 100 µL of whole blood is collected from the orbit vein into an EDTA-K2 anticoagulant tube at predose, 0.5, 1, 2, 4, 8, 24, 48 and 72 hours respectively. The blood samples are centrifuged at 1500 g for 10 minutes to obtain plasma, which is stored at −90° C. to −60° C. for further analysis and assay.

Sample Treatment (1) Method for Treating the Samples for Tirzepatide, P014, P016 and P020

20.0 µL of thawed plasma sample is taken. 20 µL of 50% aqueous methanol solution (containing 100 ng mL$^{-1}$ internal standard) and 60 µL of acetonitrile are added sequentially to precipitate protein. The mixture is vortexed for 5 minutes, and centrifuged at 3700 rpm for 8 minutes. 50.0 µL of the supernatant is taken, into which 50.0 µL of 0.5% aqueous formic acid solution is added. The mixture is vortexed for 5 minutes. 50 µL of the mixture solution is sampled and injected into the LC-MS/MS to determine the drug concentration in plasma.

Based on the drug concentration in plasma of the compounds in C57 mice, the pharmacokinetic parameters are calculated by applying the software Winnolin 8.2 in a non-compartmental model, and the results are shown in Table 7 and Table 8 below.

TABLE 7

Average Pharmacokinetic Parameters after Single
Subcutaneous Administration to Mice

| PK Parameters | Unit | Tirzepatide | P014 | P016 | P020 |
|---|---|---|---|---|---|
| $C_{max}$ | ng/mL | 871 | 851.84 | 433.67 | 835.67 |
| $T_{max}$ | hr | 6 | 6 | 8 | 4.25 |
| $T_{1/2}$ | hr | 9.21 | 20.33 | 23.05 | 19.89 |
| $AUC_{(0-t)}$ | ng · hr/mL | 19413.9 | 27316.4 | 15914.8 | 18950.6 |
| $AUC_{(0-\infty)}$ | ng · hr/mL | 19704.7 | 30150.5 | 18160.6 | 21093.3 |
| $MRT_{(0-t)}$ | hr | 14.48 | 22.94 | 25.98 | 21.84 |
| $MRT_{(0-\infty)}$ | hr | 15.29 | 30.28 | 35.91 | 29.36 |

TABLE 8

| | | Average Pharmacokinetic Parameters after Single Intravenous administration to Mice | | | |
| --- | --- | --- | --- | --- | --- |
| PK Parameters | Unit | Tirzepatide | P014 | P016 | P020 |
| $C_0$ | ng/mL | 1901.94 | 1943.93 | 1147.89 | 1819.74 |
| $T_{1/2}$ | hr | 10.47 | 17.20 | 20.15 | 16.66 |
| $AUC_{(0-t)}$ | ng · hr/mL | 12723.1 | 17458.9 | 11082.1 | 16281.7 |
| $AUC_{(0-\infty)}$ | ng · hr/mL | 12822.1 | 18245.6 | 12083.3 | 17369.9 |
| $MRT_{(0-t)}$ | hr | 11.39 | 15.72 | 19.92 | 16.80 |
| $MRT_{(0-\infty)}$ | hr | 12.00 | 19.215 | 26.64 | 21.77 |

The pharmacokinetics study on mice by subcutaneously injecting the compounds according to the present invention shows that: the half-life of P014, P016 and P020 are greater than the half-life of Tirzepatide (increased by 116.0% to 150.3%). That means that the half-life of these compounds are significantly greater than that of Tirzepatide. As compared with Tirzepatide, a commercially available dual-target product, the compounds according to the present invention modified by the modifying chain can provide a longer half-life in plasma.

(III) Pharmacokinetics in Cynomolgus Monkeys

After subcutaneous or intravenous administration to cynomolgus monkeys, plasma is collected and the drug concentration in plasma is determined to illustrate the in vivo pharmacokinetic properties of the compound according to the present invention. The compound is dissolved in 1.4% PG in 8 mM $Na_2HPO_4$ Buffer (pH 7.39), and filtered through a filter membrane (PTFE, 0.45 μm) to obtain 25 and 12.5 nmol/mL solution of the compound respectively. The at 2200 g for 10 minutes to obtain a plasma, which is stored at −90° C. to −60° C. for further analysis and assay.

Sample Treatment (1) Method for Treating the Samples for Tirzepatide, P014, P016, P017 and P020

70.0 μL of thawed plasma sample is taken. 70 μL of acetonitrile (containing 1 ng/ml of the internal standard) is added to precipitate protein. The mixture is vortexed for 1 minute, and centrifuged at 14000 rpm for 10 minutes. 60.0 μL of the supernatant is taken, into which 60.0 μL of 0.5% aqueous formic acid solution is added. The mixture is vortexed for 5 minutes. 10 μL of the mixture solution is sampled and injected into the LC-MS/MS to determine the drug concentration in plasma.

Based on the drug concentration in plasma of the compounds in the cynomolgus monkeys, the pharmacokinetic parameters are calculated by applying the software Winnolin 8.2 in a non-compartmental model, and the results are shown in Table 9 and Table 10 below.

TABLE 9

| | | Average Pharmacokinetic Parameters after Single Subcutaneous Administration to Cynomolgus Monkeys | | |
| --- | --- | --- | --- | --- |
| PK Parameters | Unit | Tirzepatide | P014 | P016 |
| $T_{max}$ | hr | 22.67 ± 10.10 | 16.00 ± 6.93 | 40.00 ± 13.90 |
| $C_{max}$ | ng/mL | 1297.45 ± 300.00 | 951.00 ± 283 | 2997.00 ± 481.00 |
| $T_{1/2}$ | hr | 62.54 ± 6.07 | 52.70 ± 6.45 | 60.40 ± 12.80 |
| $AUC_{(0-t)}$ | hr * nng/mL | 148063.24 ± 38207.00 | 87690.00 ± 24556.00 | 319272.00 ± 41475.00 |
| $AUC_{(0-\infty)}$ | hr * ng/mL | 150081.26 ± 39104.00 | 88432.00 ± 24213.00 | 322800.00 ± 44567.00 |
| $MRT_{(0-t)}$ | hr | 99.62 ± 6.26 | 74.20 ± 13.83 | 96.50 ± 15.90 |
| $MRT_{(0-\infty)}$ | hr | 104.89 ± 7.58 | 77.40 ± 13.46 | 101.00 ± 19.2 |

| PK Parameters | Unit | P017 | P020 |
| --- | --- | --- | --- |
| $T_{max}$ | hr | 48.00 ± 24.00 | 22.70 ± 10.10 |
| $C_{max}$ | ng/mL | 1655.00 ± 295.00 | 1349.00 ± 77.00 |
| $T_{1/2}$ | hr | 44.30 ± 4.80 | 67.40 ± 9.47 |
| $AUC_{(0-t)}$ | hr * nng/mL | 153476.00 ± 28919.00 | 161575.00 ± 10637.00 |
| $AUC_{(0-\infty)}$ | hr * ng/mL | 154121.00 ± 28747.00 | 163878.00 ± 12089.00 |
| $MRT_{(0-t)}$ | hr | 76.40 ± 12.70 | 97.50 ± 9.67 |
| $MRT_{(0-\infty)}$ | hr | 77.80 ± 12.20 | 103.00 ± 13.10 | obtained solutions are administered to cynomolgus monkeys (4-8 kg) at a dose of 25 nmol/kg subcutaneously (s.c.) or 12.5 nmol/kg intravenously (i.v.). About 500 μL of whole blood is collected from the cephalic vein or other appropriate veins into an EDTA-K2 anticoagulant tube at predose, 2 hours, 12 hours, 24 hours, 32 hours, 48 hours, 3 days (72 hours), 4 days (96 hours), 6 days (144 hours), 9 days (216 hours), 12 days (288 hours), 15 days (360 hours) and 18 days (432 hours), respectively. The blood samples are centrifuged

TABLE 10

| | | Average Pharmacokinetic Parameters after Single Intravanous Administration to Cynomolgus Monkeys | |
| --- | --- | --- | --- |
| PK Parameters | Unit | Tirzepatide | P016 |
| $C_0$ | ng/mL | 1167.70 ± 159.90 | 1699.50 ± 334.94 |
| $T_{1/2}$ | hr | 59.53 ± 5.22 | 59.81 ± 8.95 |
| $AUC_{(0-t)}$ | hr * ng/mL | 57554.64 ± 11825.48 | 78169.25 ± 20321.82 |

TABLE 10-continued

| | | Average Pharmacokinetic Parameters after Single Intravanous Administration to Cynomolgus Monkeys | |
|---|---|---|---|
| PK Parameters | Unit | Tirzepatide | P016 |
| $AUC_{(0-\infty)}$ | hr * ng/mL | 58529.59 ± 11927.99 | 80032.34 ± 21063.24 |
| $MRT_{(0-t)}$ | hr | 68.34 ± 8.61 | 65.29 ± 8.85 |
| $MRT_{(0-\infty)}$ | hr | 74.27 ± 8.76 | 72.94 ± 10.91 |

The pharmacokinetics study on cynomolgus monkeys by subcutaneously injecting the compounds according to the present invention shows that: the half-life of P014, P016 and P020 are equivalent to that of Tirzepatide, and the $T_{max}$ of P016 and P017 are delayed as compared with that of Tirzepatide. As compared with Tirzepatide, a commercially available dual-target product, the compounds according to the present invention modified by the modifying chain can provide a comparable half-life in plasma, and the $T_{max}$ of P016 and P017 are 2 times that of Tirzepatide. The time to peak drug concentration is significantly delayed as compared to Tirzepatide, which may result in less/few gastrointestinal response or shorter titration time.

(IV) Pharmacokinetics in Beagle Dogs

After subcutaneous administration to beagle dogs, plasma is collected and the drug concentration in plasma is determined to illustrate the in vivo pharmacokinetic properties of the compound according to the present invention. The compound of the present invention is administered to a beagle dog (7-9 kg) at a dose of 0.05 mg/kg subcutaneously (s.c.). About 500 µL of whole blood is collected from the saphenous vein into an EDTA-K2 anticoagulant tube at predose, 0.5 hours, 1 hour, 2 hours, 6 hours, 10 hours, 24 hours, 48 hours, 72 hours and 96 hours, respectively. The blood samples are centrifuged at 3000 g and at 2° C. to 8° C. for 10 minutes to obtain plasma, which is stored at –90° C. to –60° C. for further analysis and assay.

Sample Treatment (1) Method for Treating the Samples for P016

20.0 µL of thawed plasma sample is taken. 20 µL of 100 ng/ml P016 is added, and mixed uniformly for 2 minutes. Then 120 µL of 0.1% formic acid methanol is added to precipitate the protein. The mixture is vortexed for 5 minutes, and centrifuged at 4815 g for 10 minutes. 100.0 µL of the supernatant is taken, into which 100 µL of 0.5% aqueous formic acid solution is added. The mixture is vortexed for 5 minutes. 10 µL of the mixture solution is sampled and injected into the LC-MS/MS to determine the drug concentration in plasma.

Based on the drug concentration in plasma of the compound in the beagle dogs, the pharmacokinetic parameters are calculated by applying the software Winnolin 8.3 in a non-compartmental model. The results are shown in Table 11 below.

TABLE 11

| | | Average pharmacokinetic parameters after single subcutaneous administration in beagle dogs | |
|---|---|---|---|
| PK parameters | Unit | P016 | |
| $T_{max}$ | hr | 19.33 ± 8.08 | |
| $C_{max}$ | ng/mL | 407.33 ± 45.83 | |
| $T_{1/2}$ | hr | 69.32 ± 13.97 | |
| $AUC_{0-t}$ | hr * ng/mL | 29924.99 ± 5656.65 | |

TABLE 11-continued

| | | Average pharmacokinetic parameters after single subcutaneous administration in beagle dogs | |
|---|---|---|---|
| PK parameters | Unit | P016 | |
| $AUC_{0-inf}$ | hr * ng/mL | 52127.67 ± 14728.99 | |
| $MRT_{0-t}$ | hr | 44.77 ± 4.17 | |
| $MRT_{0-inf}$ | hr | 107.9 ± 23.22 | |

The pharmacokinetics study on beagle dogs by subcutaneously injecting the compound P016 according to the present invention shows that: the half-life of P016 is 69.32 hours, the time to peak is 19.33 hours, the peak concentration is 407.33 ng/ml, and the $AUC_{0-t}$ is 29925 hr*ng/ml. There is a certain exposure after subcutaneous administration, and it can support subcutaneous administration and a dosage frequency of once per week.

III. Pharmacodynamics Effects (I) Pharmacodynamics Effects in db/db Mice is Intended to Studying the Effects of the Compounds According to the Present Invention on Blood Glucose in Diabetic Model Mice (db/db Mice).

In this study, db/db mice are subcutaneously single administered, and the changes in the blood glucose, the food intake, and the body weight of the mice are measured to illustrate the hypoglycemic effects of the compounds according to the present invention as well as the duration of the drug effect, and compared them with those of the positive controls of Tirzepatide and P001. In this study, 8-9 week old male db/db mice are used. The db/db mice are placed in an individual ventilated cage (IVC) facility with a controlled temperature (20-26° C.) and humidity (40-70%) and a controlled 12h: 12 h light-dark cycle. The mice received food and water ad libitum. Blood is sampled at the tail tip, and the fasting blood glucose is measured by a Roche blood glucose meter. The mice are randomly divided into groups according to the initial blood glucose and initial body weight (n=6/group), and each group had similar body weight and blood glucose.

The compound according to the present invention (10 nmol/kg), or the positive controls of Tirzepatide (10 nmol/kg) and P001 (10 nmol/kg), are dissolved in a vehicle (PBS containing 0.1% Tween 20, pH 7.2-7.4). After a single subcutaneous administration, the random blood glucoses are recorded at the set time point (0 to 120 hours, the recording of the random blood glucose is stopped until there is no difference between the random blood glucose of the compound and that of the vehicle group), and the daily body weight and food intake are also recorded. The data results are statistically analyzed using GraphPad Prism8, and the statistical differences among the groups are analyzed following a T-Test. Significant differences are identified at $p<0.05$.

Hypoglycemic Duration: the longest time during which the random blood glucose of the compound has a significant difference ($P<0.05$) vs. the vehicle group.

TABLE 12

| | Hypoglycemic Duration of the Compounds | |
|---|---|---|
| Group | Compound | Hypoglycemic Duration (h) |
| Group 1 | P001 | 32 |
| | Tirzepatide | 56 |
| | P007 | 56 |

TABLE 12-continued

| Hypoglycemic Duration of the Compounds | | |
|---|---|---|
| Group | Compound | Hypoglycemic Duration (h) |
| | P008 | 72 |
| | P014 | 104 |
| | P019 | 56 |
| Group 2 | Tirzepatide | 48 |
| | P013 | 72 |
| | P015 | 32 |
| | P016 | 104 |
| | P017 | 72 |
| | P018 | 48 |
| | P020 | 104 |

Figure 1B:
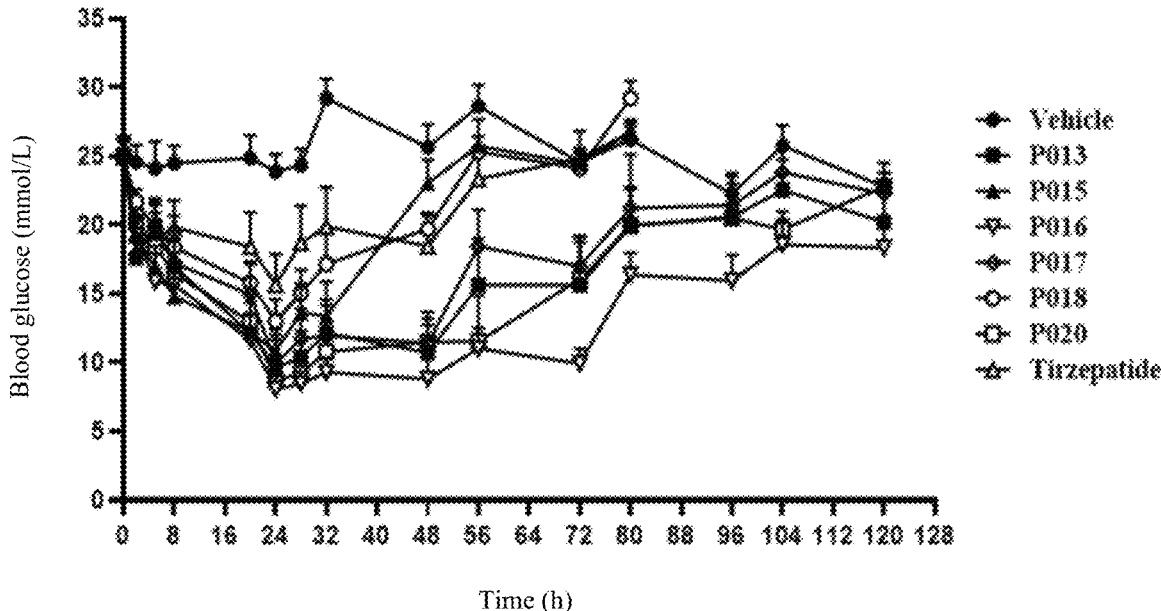

As compared with P001, the hypoglycemic duration of the compounds according to the present invention is more than 24 hours (P007, P008, P014, P019), even more than 40 hours (P008, P014), and more than 72 hours (P014) (see Table 12, FIG. 1A, and FIG. 1B) longer than that of P001.

As compared with Tirzepatide, the hypoglycemic duration of the compounds according to the present invention is equivalent or longer (P007, P008, P013, P014, P016, P017, P018, P019, and P020), even more than 16 hours (P008, P013, P014, P016, P017, P020), more than 24 hours (P013, P014, P016, P017, P020), more than 48 hours (P014, P016, P020), more than 56 hours (P016, P020) longer than that of Tirzepatide (see Table 12).

Figure 2A:
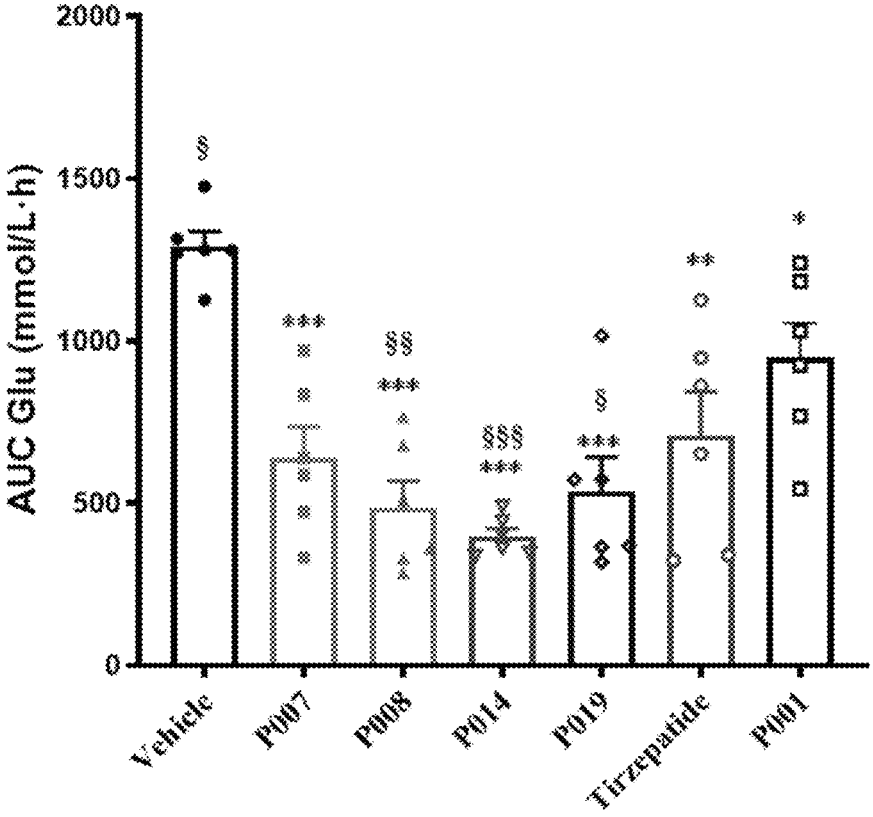
FIGS. 2A-2C show blood glucose AUC in db/db mice after administration.

As compared with P001, based on the experiments according to the method described above, during the test period, the hypoglycemic effects of P008 (p<0.01), P014 (p<0.001) and P019 (p<0.05) are significantly better than that of P001 (blood glucose AUC, P<0.05, as shown in FIG. 2A). The inhibition of the blood glucose AUC is 2.3, 2.6 and 2.2 times of that of P001 respectively; the duration of hypoglycemic effect is 40 hours, 72 hours and 24 hours longer than that of P001 respectively (Table 12). The hypoglycemic effect of P007 is comparable to that of P001, but the duration of hypoglycemic effect is 24 hours longer than that of P001 (as shown in FIG. 2A, and Table 12).

Figure 2B:
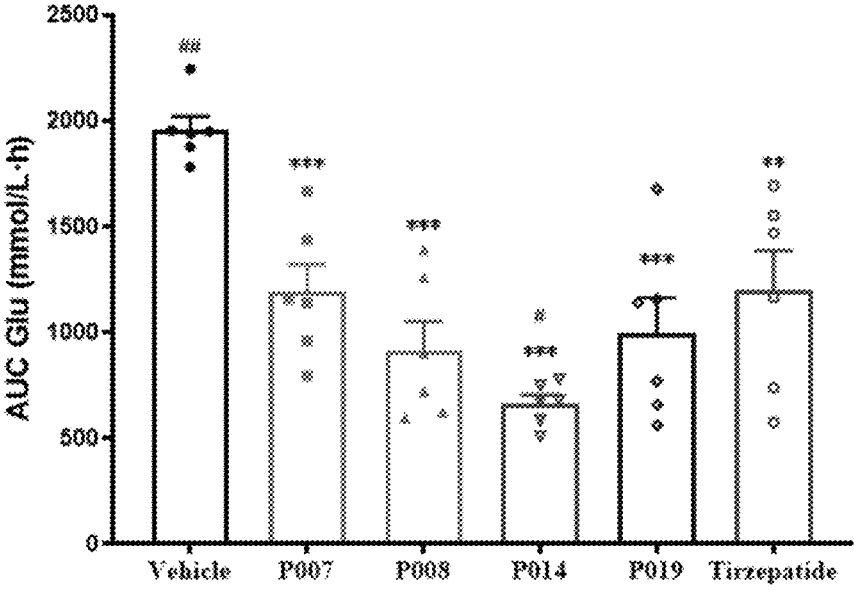
Figure 2C:
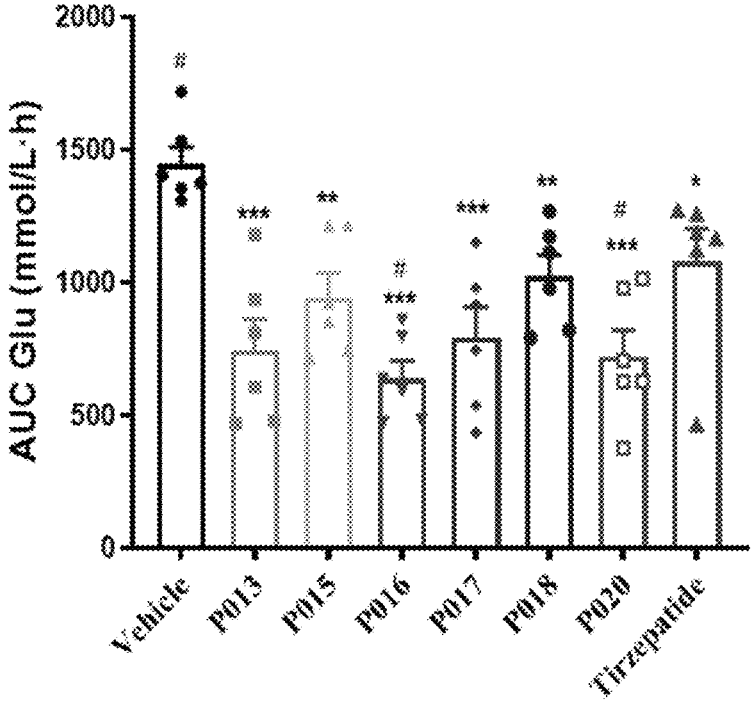
Figure 3A:
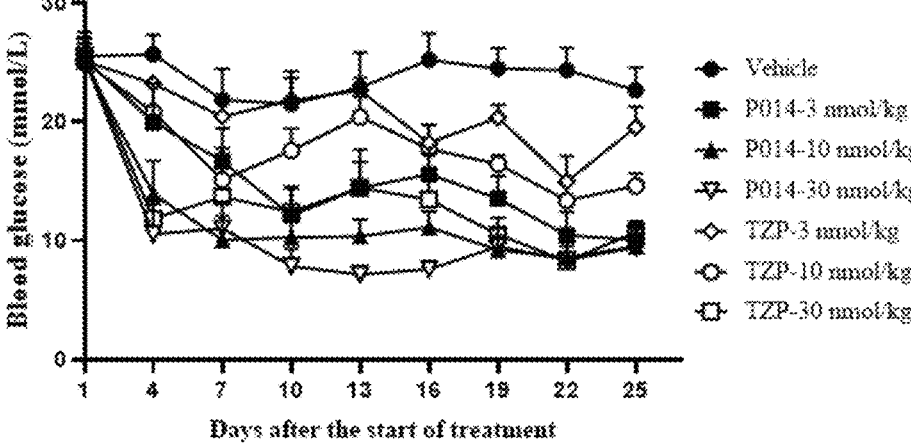
FIGS. 3A-3D show changes in blood glucose in db/db mice after multiple administrations.
Figure 3B:
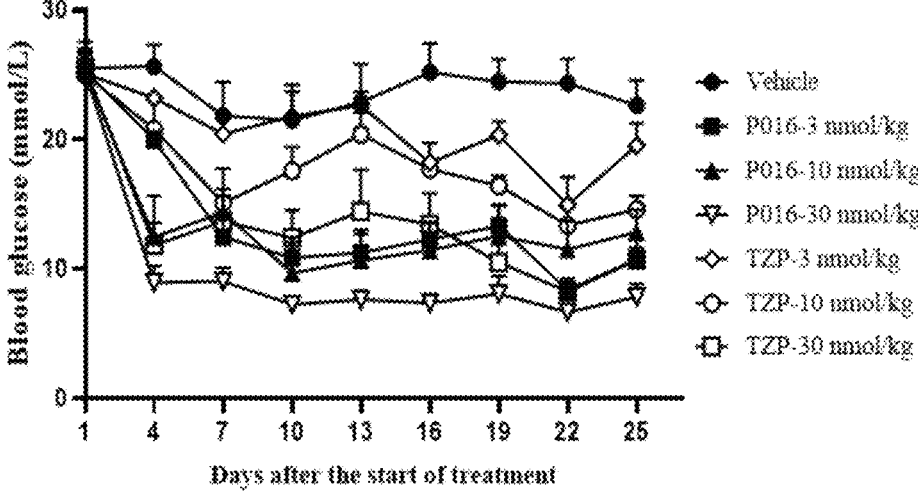
Figure 3C:
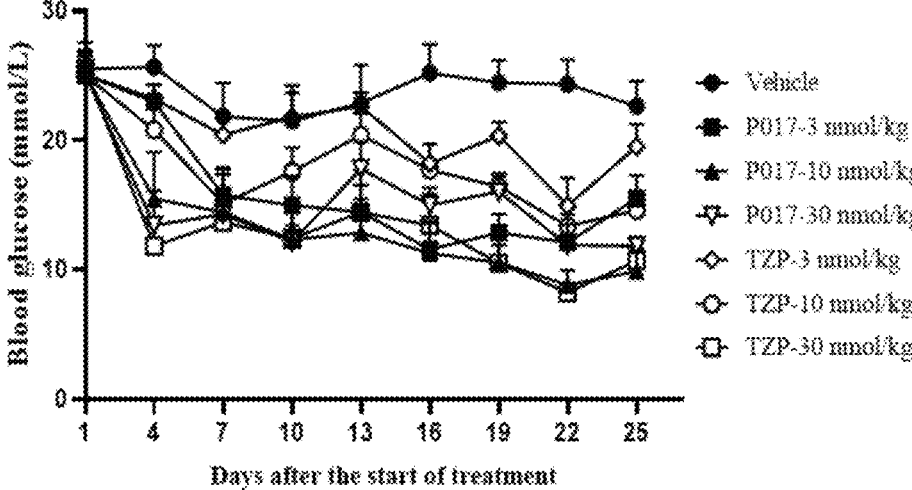
Figure 3D:
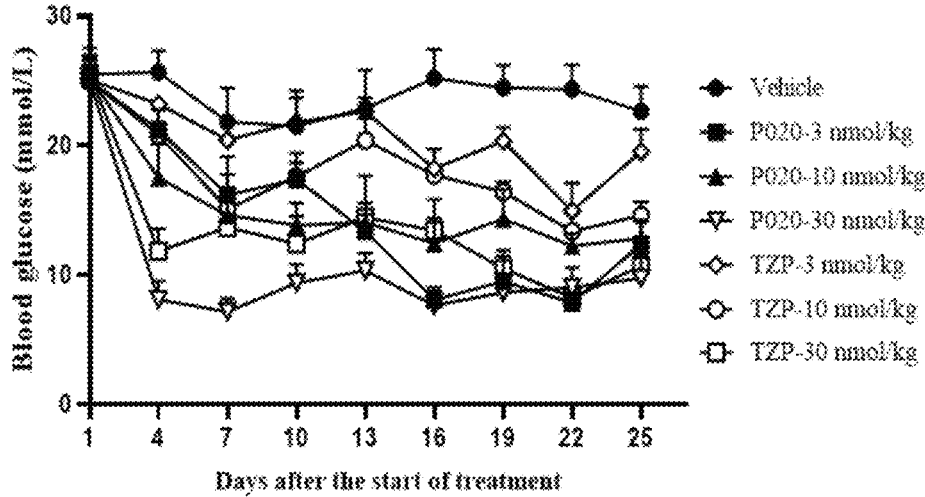

As compared with Tirzepatide: the hypoglycemic effects of P014 (p<0.05, FIG. 2B), P016 (p<0.05, FIG. 2C) and P020 (p<0.05, FIG. 2C) are stronger than that of Tirzepatide (blood glucose AUC, p<0.05). The inhibitions of the blood glucose AUC are 1.7, 2.2 and 2.0 times of that of Tirzepatide respectively. Moreover, they also show significantly longer duration of drug effects (48 hours, 56 hours and 56 hours longer than that of Tirzepatide respectively, Table 12). The hypoglycemic effects of P013 and P017 are comparable to that of Tirzepatide (FIG. 2C), but the duration of drug effects is 24 hours longer than that of Tirzepatide (Table 12).

Surprisingly, as compared with P001, the acylated GLP-1/GIP agonists of the present invention significantly improve the hypoglycemic effect while maintaining the long-acting effect. The compounds according to the present invention with modifying chains in different forms can realize stronger and longer-lasting hypoglycemic effects than P001. Moreover, some compounds according to the present invention exhibit stronger and longer-lasting hypoglycemic effects than Tirzepatide.

Furthermore, in conjunction with performance of the binding and agonistic activity of the compounds according to the present invention at the targeted human GLP-1 and GIP receptors, it is surprisingly found that, although the compounds according to the present invention show a significantly reduced binding and agonistic activity at both the targeted human GLP-1 receptor and the targeted human GIP receptor as compared with P001, the hypoglycemic effects of the compounds according to the present invention are significantly better than that of P001.

(II) Multiple Administration Experiment on db/db Mice

In this study, db/db mice are subcutaneously administrated multiple times, and the changes in the blood glucose in the mice are determined to further illustrate the hypoglycemic effects of the compounds according to the present invention, and compared them with that of the positive control Tirzepatide. In this study, 7-8 week old male db/db mice are used. The db/db mice are placed in an individual ventilated cage (IVC) facility with a controlled temperature (20-26° C.) and humidity (40-70%) and a controlled 12:12 h light-dark cycle. The mice received food and water ad libitum. Blood are sampled at the tail tip, and the fasting blood glucose is measured by a Roche blood glucose meter. The mice are randomly divided into groups according to the initial blood glucose and initial body weight (n=6/group), and each group had similar body weight and blood glucose.

The compounds according to the present invention (3, 10, 30 nmol/kg) or the positive control Tirzepatide (3, 10, 30 nmol/kg) is dissolved in a vehicle (PBS containing 0.1% Tween 20, pH 7.2-7.4). The mice are subcutaneously administrated every 3 days for 4 weeks. Subcutaneous administration is conducted on days 1, 4, 7, 10, 13, 16, 19, 22 and 25. Random blood glucose is recorded every 3 days throughout the study. On day 28, the fasting blood glucose is measured. Then the blood is collected by orbital blood sampling. After the orbital blood sampling, the animals are sacrificed, and the liver is taken and weighed. After 1 to 2 hours, the collected blood is centrifuged at 3000 rpm for 10 min to separate the serum. Biochemical indicators such as triglyceride (TG), alanine aminotransferase (ALT), and total bilirubin (TBIL) are determined with a biochemical analyzer. The data results are statistically analyzed using Graph-Pad Prism8, and the statistical differences among the groups are analyzed following T-Test. Significant differences are identified at p<0.05.

In the experiment performed as described in the above method, the compounds according to the present invention, such as P014, P016, P017 and P020, all show better blood glucose inhibition as compared with Tirzepatide at a dose of 3 nmol/kg. At a dose of 30 nmol/kg, the drug efficacy of P016 is superior to that of Tirzepatide (see FIGS. 3A-3D, and Table 13). P016, P017 and P020 significantly reduced liver weight in db/db mice at several doses, while Tirzepatide did not reduce liver weight at the three tested doses. The compounds according to the present invention, such as P014, P016, P017, P020 and Tirzepatide, can effectively reduce TG in the serum of the db/db mice (except for P017 and Tirzepatide groups at 3 nmol/kg), and the P016 and P020 groups at some doses show better drug efficacy than Tirzepatide (see Table 14). In addition, P014 and P016 can also reduce TBIL and/or ALT in serum (see Table 15).

TABLE 13

| Fasting Blood Glucose and Blood Glucose AUC of db/db Mice | | |
|---|---|---|
| Group | D28 Fasting Blood Glucose (mmol/L) | AUC $_{4-25\ day}$ Glu (mmol/L day) |
| Vehicle | 18.34 ± 3.45 | 493.71 ± 40.3 |
| P014 3 nmol/kg | 10.22 ± 1.58*### | 294 ± 40.43**# |
| P014 10 nmol/kg | 10.72 ± 1.75 | 214.4 ± 33.73***# |
| P014 30 nmol/kg | 13.38 ± 3.38 | 190.62 ± 26.47*** |
| P016 3 nmol/kg | 10.42 ± 1.46*### | 256.38 ± 22***##### |

TABLE 13-continued

Fasting Blood Glucose and Blood Glucose AUC of db/db Mice

| Group | D28 Fasting Blood Glucose (mmol/L) | AUC $_{4\text{-}25\ day}$ Glu (mmol/L day) |
|---|---|---|
| P016 10 nmol/kg | 12.5 ± 2.19 | 249.25 ± 41.42** |
| P016 30 nmol/kg | 6.05 ± 0.41**$^{\#\#}$ | 163.98 ± 11.57****$^{\#}$ |
| P017 3 nmol/kg | 11.68 ± 1.7$^{\#}$ | 303.78 ± 33.24**$^{\#}$ |
| P017 10 nmol/kg | 11.95 ± 2.51 | 249.65 ± 47.65** |
| P017 30 nmol/kg | 10.08 ± 0.79* | 294.96 ± 11.96** |
| P020 3 nmol/kg | 9.6 ± 1.32*$^{\#\#\#}$ | 268.28 ± 24.64***$^{\#}$ |
| P020 10 nmol/kg | 10.7 ± 1.62 | 290.78 ± 27.25** |
| P020 30 nmol/kg | 8.22 ± 1.07* | 184.18 ± 22.44**** |
| TZP 3 nmol/kg | 17.35 ± 1.21 | 419.85 ± 26.42 |
| TZP 10 nmol/kg | 13.82 ± 1.99 | 355.68 ± 30.8* |
| TZP 30 nmol/kg | 10.88 ± 1.2 | 252.7 ± 32.81** |

T-Test,
*p < 0.05,
**p < 0.01,
***p < 0.001,
****p < 0.0001 vs. vehicle group;
$^{\#}$p < 0.05,
$^{\#\#}$p < 0.01,
$^{\#\#\#}$p < 0.001 vs. Tirzepatide(TZP) group at the same dose. Results are expressed as Mean ± SEM for 6 mice.

TABLE 14

Liver Weight and Serum TG in db/db Mice

| Group | Liver Weight (g) | Serum TG(mmol/L) |
|---|---|---|
| Vehicle | 2.61 ± 0.19 | 1.87 ± 0.13 |
| P014 3 nmol/kg | 2.26 ± 0.18 | 1.39 ± 0.07* |
| P014 10 nmol/kg | 2.1 ± 0.14 | 1.29 ± 0.03** |
| P014 30 nmol/kg | 1.89 ± 0.31 | 1.14 ± 0.18* |
| P016 3 nmol/kg | 2.24 ± 0.1$^{\#}$ | 1.21 ± 0.04***$^{\#}$ |
| P016 10 nmol/kg | 1.98 ± 0.12* | 1.22 ± 0.24* |
| P016 30 nmol/kg | 1.78 ± 0.08** | 1.2 ± 0.05*** |
| P017 3 nmol/kg | 2.14 ± 0.08*$^{\#\#\#}$ | 1.58 ± 0.17 |
| P017 10 nmol/kg | 2.11 ± 0.09* | 1.19 ± 0.05*** |
| P017 30 nmol/kg | 2.35 ± 0.09 | 1.09 ± 0.06*** |
| P020 3 nmol/kg | 2.03 ± 0.09*$^{\#\#\#}$ | 1.37 ± 0.12* |
| P020 10 nmol/kg | 2.09 ± 0.1* | 1.07 ± 0.03***$^{\#}$ |
| P020 30 nmol/kg | 1.83 ± 0.16* | 1.2 ± 0.07** |
| TZP 3 nmol/kg | 2.49 ± 0.05 | 1.52 ± 0.11 |
| TZP 10 nmol/kg | 2.31 ± 0.17 | 1.21 ± 0.04** |
| TZP 30 nmol/kg | 2.07 ± 0.15 | 1.18 ± 0.12** |

T-Test,
*p < 0.05,
**p < 0.01,
***p < 0.001 vs. vehicle group;
$^{\#}$p < 0.05,
$^{\#\#}$p < 0.01 vs. Tirzepatide(TZP) group at the same dose. Results are expressed as Mean ± SEM for 6 mice.

TABLE 15

Serum ALT and TBIL in db/db Mice

| Group | Serum ALT (U/L) | Serum TBIL (μmol/L) |
|---|---|---|
| Vehicle | 189.55 ± 40.92 | 1.43 ± 0.3 |
| P014 3 nmol/kg | 111.24 ± 13.23 | 0.58 ± 0.11*$^{\#\#\#}$ |
| P014 10 nmol/kg | 89.9 ± 8.66* | 0.58 ± 0.15* |
| P014 30 nmol/kg | 106.47 ± 14.3 | 0.36 ± 0.15*$^{\#\#\#}$ |
| P016 3 nmol/kg | 137.93 ± 34.59 | 0.82 ± 0.13 |
| P016 10 nmol/kg | 128.94 ± 16.93 | 1.22 ± 0.28 |
| P016 30 nmol/kg | 97.7 ± 12.36* | 0.73 ± 0.16 |
| P017 3 nmol/kg | 105.16 ± 7.1 | 0.88 ± 0.26 |
| P017 10 nmol/kg | 141.65 ± 12.72 | 1.59 ± 0.07 |
| P017 30 nmol/kg | 176.48 ± 51.6 | 1.11 ± 0.1 |
| P020 3 nmol/kg | 214.56 ± 43.83 | 1.54 ± 0.25 |

TABLE 15-continued

Serum ALT and TBIL in db/db Mice

| Group | Serum ALT (U/L) | Serum TBIL (μmol/L) |
|---|---|---|
| P020 10 nmol/kg | 113.48 ± 24.18 | 0.91 ± 0.05 |
| P020 30 nmol/kg | 112.47 ± 16.69 | 0.95 ± 0.28 |
| TZP 3 nmol/kg | 146.03 ± 19.67 | 1.54 ± 0.17 |
| TZP 10 nmol/kg | 138.66 ± 31.26 | 1.2 ± 0.3 |
| TZP 30 nmol/kg | 112.48 ± 14.55 | 0.91 ± 0.04 |

T-Test,
*p < 0.05 vs. vehicle group;
$^{\#}$p < 0.05,
$^{\#\#}$p < 0.01 vs. Tirzepatide(TZP)group at the same dose. Results are expressed as Mean ± SEM for 6 mice.

To sum up, under this experimental system, the compounds according to the present invention can effectively reduce blood glucose in db/db mice by subcutaneous injection for 4 weeks. The minimum effective dose (≤3 nmol/kg) of the compounds according to the present invention is one third of that of Tirzepatide (10 nmol/kg), and the maximum drug efficacy (30 nmol/kg) of some compounds according to the present invention such as P016 is superior to that of Tirzepatide. In addition, some compounds according to the present invention exhibit reduced liver weight and protective effects to the livers in db/db mice, while Tirzepatide had no similar effect.

(III) Weight Loss Effect in DIO Mice Obesity Models

In this study, DIO mice were subcutaneously administrated multiple times with the compound according to the present invention, and the changes in the body weight and blood glucose of the mice were determined to illustrate the weight reduction effect of the compound according to the present invention, and were compared with those of the positive control Tirzepatide. In this study, 26-week-old male DIO mice were used. DIO mice were housed in appropriate cages. DIO mice were housed in an environment-monitored and well-ventilated SPF-grade animal room, with the temperature maintained between 2° and 26° C. (Actual: 20-24° C.) and relative humidity between 40% and 70% (Actual: 44%-60%). A 12-hour light/dark cycle was provided for illumination. The mice received food and water ad libitum. In the experiment, DIO mice with similar random blood glucoses (RBG) (D1) and body weights (D1) are selected and randomly grouped (n=10/group). The compound P016 of the present invention (0.3, 1, 3, 30 nmol/kg) or the positive control Tirzepatide (1, 30 nmol/kg) was dissolved in a vehicle (PBS containing 0.1% Tween20, pH 7.2-7.4). The mice were subcutaneously administrated once every 3 days for 4 consecutive weeks. Subcutaneous injection administration was conducted on Day 1, 4, 7, 10, 13, 16, 19, 22, 25, and 28.

The animals were weighed before administration on the day of first administration (D1), and at a fixed time once every 3 days after administration. Food intake is measured once daily after administration. RBG is measured before grouping and at 48 h after each administration. After fasted for 5 h on D30 (no water deprivation was required), FBG and glycated hemoglobin Alc (HbAlc) were detected, and blood was collected intravenously to separate the serum. A mouse insulin ELISA kit was used to detect the insulin content in the serum, and a biochemistry analyser was used to detect total cholesterol (TC), TG, low-density lipoprotein cholesterol (LDL), high-density lipoprotein cholesterol (HDL), free fatty acid (FFA), ALT, and aspartate aminotransferase (AST) content. The liver was collected, the perirenal and paratesticular fat tissues were separated and weighed, the organ-body ratio was calculated. The liver was stained with HE and Oil Red O for pathological scoring. The data results were statistically analyzed using one-way analysis of variance (ANOVA). A Levene's test was performed to test for variance homogeneity. If the result was homogeneous (P>0.05), a one-way analysis of variance (ANOVA) would be performed. If ANOVA showed significance (P≤0.05), a Tukey test of variancpair-wise comparisons would be performed. In the case of heterogeneity of variance (P≤0.05), a Dunnett's T3 test would be performed. Results are expressed as mean and standard deviation (Mean±SEM). The test level is 0.05. Both statistical significance and biological significance were considered when analyzing the results.

Figure 4:
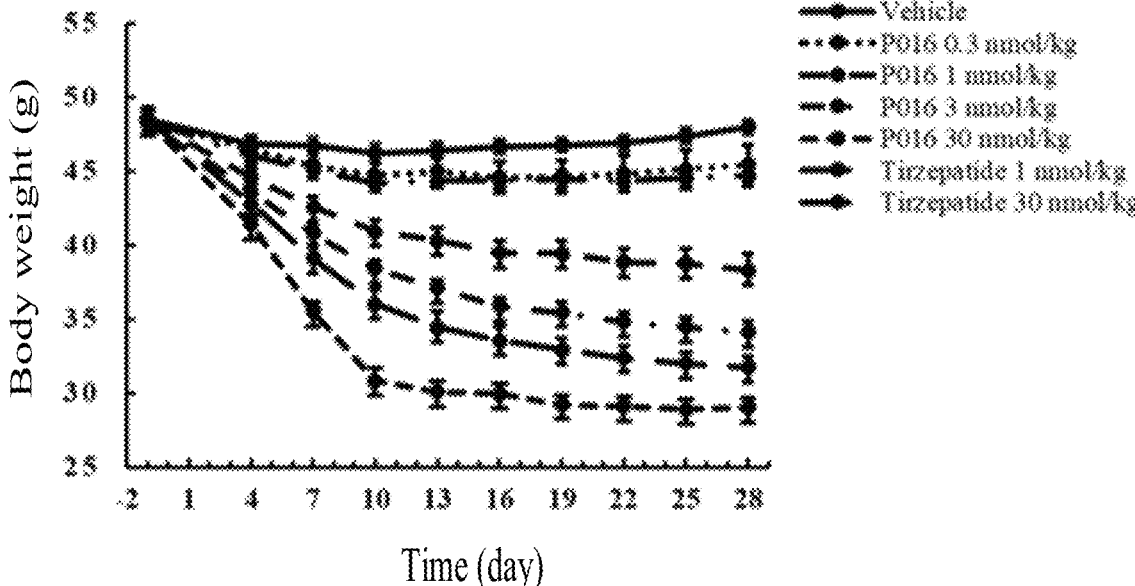
FIG. 4 shows body weight trends of DIO mice after multiple subcutaneous administrations of P016 (0.3, 1, 3, 30 nmol/kg) and Tirzepatide (1, 30 nmol/kg) at a frequency of once every 3 days.
Figure 5:
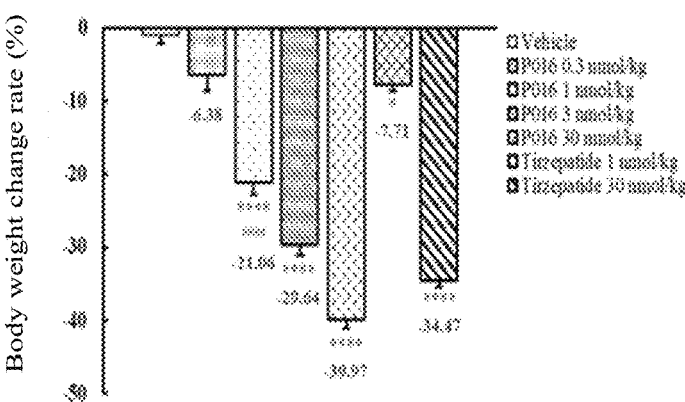
FIG. 5 shows body weight change rate (%) of DIO mice on day 28 (D28) after multiple subcutaneous administrations of P016 (0.3, 1, 3, 30 nmol/kg) and Tirzepatide (1, 30 nmol/kg) at a frequency of once every 3 days.

In the experiment conducted as described in the above method, the compound according to the present invention significantly reduced the cumulative food intake and body weight of obese mice in a dose-dependent manner. The minimum effective dose is 1 nmol/kg, and the weight loss effect at this dose was significantly better than the positive control Tirzepatide at the same dose. At a dose of 30 nmol/kg, the weight loss degree of the compound according to the present invention was greater than that of Tirzepatide (percentage of weight loss, 39.97% vs 34.47%) (see FIG. 4, FIG. 5, and Table 16). The compound according to the present invention significantly reduced the total abdominal fat (sum of perirenal fat and paratesticular fat) and serum TC in DIO mice (Table 16, Table 18), and had significant lipid-lowering effect. 1, 3, and 30 nmol/kg of the compound according to the present invention significantly reduced FBG and insulin level on D30, and improved insulin resistance (Table 17). The compound according to the present invention significantly reduced liver weight and serum ALT level and improved liver function (Table 18).

TABLE 16

| Cumulative food intake, body weight, fat and liver weights of DIO mice | | | | |
|---|---|---|---|---|
| | Cumulative food intake | Body weight (g) | Total abdominal fat (g) | Liver weight (g) |
| Vehicle | 78.83 ± 0.73 | 48.0 ± 0.5 | 3.071 ± 0.115 | 1.758 ± 0.072 |
| P016 0.3 nmol/kg | 75.75 ± 2.81 | 45.4 ± 1.3 | 2.631 ± 0.069 | 1.552 ± 0.106 |
| P016 1 nmol/kg | 61.40 ± 1.58****#### | 38.3 ± 1.1****## | 1.849 ± 0.181*** | 1.191 ± 0.075*** |
| P016 3 nmol/kg | 55.47 ± 2.72**** | 34.1 ± 0.7**** | 0.972 ± 0.076**** | 1.069 ± 0.029**** |
| P016 30 nmol/kg | 48.38 ± 2.31**** | 29 ± 0.7**** | 0.461 ± 0.034**** | 0.995 ± 0.029**** |
| Tirzepatide 1 nmol/kg | 76.51 ± 1.67 | 44.7 ± 0.87 | 2.318 ± 0.123** | 1.305 ± 0.073** |
| Tirzepatide 30 nmol/kg | 47.95 ± 2.14**** | 31.8 ± 0.7**** | 0.781 ± 0.093**** | 0.951 ± 0.031**** |

Note:

**$P \leq 0.01$,

***$P \leq 0.001$,

****$P \leq 0.0001$ are compared with the Vehicle group,

$P \leq 0.01$,

$P \leq 0.0001$ are compared with the same dose of positive control Tirzepatide group. Results are expressed as Mean ± SEM for 10 mice.

TABLE 17

| Fasting blood glucose, insulin and insulin resistance index in DIO mice | | | |
|---|---|---|---|
| | Fasting blood glucose | Insulin | Insulin resistance index |
| Vehicle | 14.84 ± 0.67 | 2.911 ± 0.294 | 41.698 ± 4.071 |
| P016 0.3 nmol/kg | 13.78 ± 0.39 | 3.285 ± 0.481 | 43.94 ± 6.288 |
| P016 1 nmol/kg | 11.23 ± 0.40****# | 1.911 ± 0.29 | 21.532 ± 3.705* |
| P016 3 nmol/kg | 10.36 ± 0.67**** | 1.196 ± 0.185* | 11.991 ± 1.907*** |
| P016 30 nmol/kg | 8.39 ± 0.30**** | 0.624 ± 0.130** | 5.179 ± 1.178**** |
| Tirzepatide 1 nmol/kg | 9.19 ± 0.35**** | 2.317 ± 0.511 | 20.983 ± 4.926 |
| Tirzepatide 30 nmol/kg | 7.96 ± 0.33**** | 1.418 ± 0.535 | 11.023 ± 4.147* |

Note:

*$P \leq 0.05$,

**$P \leq 0.01$,

***$P \leq 0.001$,

****$P \leq 0.0001$ are compared with the Vehicle group,

$P \leq 0.05$ is compared with the same dose of positive control Tirzepatide group. Results are expressed as Mean ± SEM for 10 mice.

TABLE 18

| Serum TC and ALT of DIO mice | | |
| --- | --- | --- |
| | Serum TC | ALT |
| Vehicle | 4.48 ± 0.24 | 120.90 ± 16.22 |
| P016 0.3 nmol/kg | 4.07 ± 0.26 | 95.60 ± 14.09 |
| P016 1 nmol/kg | 3.26 ± 0.20* | 43.90 ± 3.86* |
| P016 3 nmol/kg | 2.61 ± 0.13*** | 52.80 ± 9.62* |
| P016 30 nmol/kg | 2.50 ± 0.18**** | 49.60 ± 5.67* |
| Tirzepatide 1 nmol/kg | 3.54 ± 0.15 | 56.20 ± 4.66* |
| Tirzepatide 30 nmol/kg | 2.65 ± 0.08*** | 41.50 ± 5.31* |

Note:
*$P \leq 0.05$,
***$P \leq 0.001$,
****$P \leq 0.0001$ are compared with the Vehicle group. Results are expressed as Mean ± SEM for 10 mice.

In summary, in this experimental system, the compound of the present invention could effectively reduce the weight of DIO mice after 4 weeks of subcutaneous injection. The minimum effective dose was 1 nmol/kg. The weight loss effect at this dose was significantly better than the positive control Tirzepatide at the same dose, and the maximum weight loss of the compound according to the present invention (30 nmol/kg) is greater than Tirzepatide at the same dose (percentage of weight loss, 39.97% vs 34.47%). In addition, the compound of the present invention exhibited effects on lowering blood glucose, improving insulin resistance, and improving liver function.

(IV) Repeated Administration on Male Rats for 2 Weeks

1. Experimental Schedule

77 SD male rats (SPF grade) are selected and randomly divided into 10 groups based on body weight. Group 1 is the vehicle control group, including 5 animals. Group 2 to Group 4 are the control groups administrated with commercially available Tirzepatide, each group including 8 animals, wherein 5 animals for primary test, and 3 animals for toxicokinetics test, and the administration dose is 1, 3, and 10 mg/kg respectively. Group 5 to Group 7 are the groups administrated with the test substance 1; and Group 8 to Group 10 are the groups administrated with the test substance 2, each group including 8 animals, wherein 5 animals for primary test, and 3 animals for toxicokinetics test, and the administration dose is 1, 3 and 10 mg/kg respectively. Each of the above groups is continuously administered twice a week for 2 weeks (administrating at Day 1, Day 5, Day 8, Day 12 and Day 15).

During the experiment, the cage condition monitoring, detailed clinical observations, determination of the food consumption, determination of body weight, measurement of the blood biochemical and hematology indicator, investigation of the gross anatomy, weighing of the organ, studying on toxicokinetic are performed on all the groups of the animals.

2. Data Statistics

The tables below illustrates the combinations used for statistical comparison in detail. The tables are as follows:

| Method for Statistical Analysis | |
| --- | --- |
| Group as control | Groups used for comparison |
| 1 | 2, 3, 4, 5, 6, 7, 8, 9, 10 |

Original data during each time period is tabulated. The average values and standard deviations and/or group change are calculated for each assay endpoint based on the group and sex. For each endpoint, the administrated group will be compared with the control group in the following aspect. A logarithmic conversion is performed to the endpoint data as desired prior to the start of the specific analyses.

| Statistical Analysis | |
| --- | --- |
| Item | Analytical Method |
| Food Consumption | comparison between groups |
| Weight | |
| Hematology (excluding white blood cell count) | |
| Coagulation | |
| Serum Biochemistry | |
| Organ Weight | |
| Absolute Weight | |
| Organ Coefficients relative to body weight and brain | |
| White Blood Cell Count | logarithmic conversion/ group-group comparison |
| Total White Blood Cells | |
| White Blood Cell Differential Count | |

3. Experimental Results

Body Weight/Weight Gain: After the first administration, the decrease of the body weight is observed in each of the following groups: Tirzepatide at a dose ≥3 mg/kg; P014 and P016 at a dose ≥1 mg/kg. With the continuation of the administration, the body weight is recovered, and by the end of the administration, all groups had a positive increase in body weight, but the weight gain is lower than that of control group, showing an obvious dose-dependent relationship.

Food Intake: throughout the test procedure, a dose-dependent decrease in food intake is observed in each administration group (Tirzepatide, P014 and P016). Blood Chemistry: Amylase and triglyceride levels decrease. Hematology: reticulocyte level decreases slightly. Gross Anatomy: no abnormalities are found in each administration group (Tirzepatide, P014 and P016). Organ Weight: the weight of heart, liver and spleen and the like in each administration group (Tirzepatide, P014 and P016) decreased, which is not significantly different from that in the vehicle control group. This may be associated to the weight loss caused by pharmacological effects. Toxicokinetic: $C_{max}$ and AUC in each administration group (Tirzepatide, P014 and P016) increase nearly proportionally to the dose. The administration groups (Tirzepatide, P014 and P016) show no substantial accumulation when continuously administered twice a week for 2 weeks.

Each administration group (Tirzepatide, P014 and P016) had a MTD>10 mg/kg when continuously administered twice a week for 2 weeks. $C_{max}$, $AUC_{last}$ after the last dose and the safety window of the test are as follows:

TABLE 19

| Safety Window for Each Administration Group | | | |
| --- | --- | --- | --- |
| Test Article | Tirzepatide | P014 | P016 |
| MTD | 2077 nmol/kg (MTD for 2 weeks) | 1980 nmol/kg (MTD for 2 weeks) | 1924 nmol/kg (MTD for 2 weeks) |
| Efficacy Dose | 10 nmol/kg | 3 nmol/kg | 3 nmol/kg |
| Safety Window (based on dosage) | 416 | 1319 | 1282 |
| Safety Window (based on exposure $AUC_{last}$) | 130 | 596 | 920 |

To sum up, P016 and P014 have similar toxicity properties to Tirzepatide, but have a wider safety window (based on exposure, the safety window of P014 is more than 4 times of that of Tirzepatide, and the safety window of P016 is more than 7 times of that of Tirzepatide).

In addition, the safety windows of the compounds according to the present invention, in particular P014 and P016, is 10 times larger, or 20 times larger, or 30 times larger, or 40 times larger, or 50 times larger, or 60 times larger, or 70 times larger, or 80 times larger, or 90 times larger than that of P001.

Meanwhile, under the same exposure, the compounds according to the present invention have a lower impact on heart rate (HR) than Tirepatide. The increase in HR for P016 is lower than that for Tirepatide. No sustained HR increase exceeding 30% is observed. At the same exposure, heart rate recovery for P016 is faster than TZP (the recover time for P016 is between 72 and 120 hours, and the recovery time for TZP>120 hours).

The peptide compounds provided by the present invention and the use thereof have been introduced in detail above.

Specific examples are applied herein to illustrate the principle and embodiments of the present invention. The illustration of the above examples are merely used to help understand the method and the central idea of the present invention. It should be indicated that those skilled in the art can make several improvements and modifications to the present invention without departing from the principles of the present invention, and these improvements and modifications also fall within the protection scope of the claims of the present invention.

Amino Acid Sequence:

| No. in sequence listing | Name | Sequence |
| --- | --- | --- |
| (SEQ ID NO: 1) | P001 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K; wherein $X_1$ is Aib; $X_2$ is αMePhe; $X_3$ is Aib; $X_4$ is Aib; and the C-terminal amino acid is amidated as a C-terminal primary amide (SEQ ID NO: 1) |
| (SEQ ID NO: 2) | P007 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K; wherein $X_1$ is Aib; $X_2$ is αMePhe; $X_3$ is Aib; $X_4$ is Aib; K at position 24 is chemically modified through conjugation to the ε-amino of the K side-chain with ([2-(2-amino-ethoxy)-ethoxy]-acetyl)$_2$-(γ-Glu)$_1$-CO-$(CH_2)_{16}$-$CO_2$H; and the C-terminal amino acid is amidated as a C-terminal primary amide (SEQ ID NO: 2). |
| (SEQ ID NO: 3) | P008 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K; wherein $X_1$ is Aib; $X_2$ is αMePhe; $X_3$ is Aib; $X_4$ is Aib; K at position 28 is chemically modified through conjugation to the ε-amino of the K side-chain with ([2-(2-amino-ethoxy)-ethoxy]-acetyl)$_2$-(γ-Glu)$_1$-CO-$(CH_2)_{16}$-$CO_2$H; and the C-terminal amino acid is amidated as a C-terminal primary amide (SEQ ID NO: 3). |
| (SEQ ID NO: 4) | P013 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K; wherein $X_1$ is Aib; $X_2$ is αMePhe; $X_3$ is Aib; $X_4$ is Aib; K at position 24 is chemically modified through conjugation to the ε-amino of the K side-chain with ([2-(2-amino-ethoxy)-ethoxy]-acetyl)$_2$-(γ-Glu)$_1$-CO-$(CH_2)_{18}$-$CO_2$H; and the C-terminal amino acid is amidated as a C-terminal primary amide (SEQ ID NO: 4). |
| (SEQ ID NO: 5) | P014 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K; wherein $X_1$ is Aib; $X_2$ is αMePhe; $X_3$ is Aib; $X_4$ is Aib; K at position 24 is chemically modified through conjugation to the ε-amino of the K side-chain with ([2-(2-amino-ethoxy)-ethoxy]-acetyl)$_2$-(γ-Glu)$_1$-CO-$(CH_2)_{20}$-$CO_2$H; and the C-terminal amino acid is amidated as a C-terminal primary amide (SEQ ID NO: 5). |

| No. in sequence listing | Name | Sequence |
|---|---|---|
| (SEQ ID NO: 6) | P015 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K;<br>wherein $X_1$ is Aib; $X_2$ is αMePhe; $X_3$ is Aib; $X_4$ is Aib;<br>K at position 24 is chemically modified through conjugation to the ε-amino of the K side-chain with ([2-(2-amino-ethoxy)-ethoxy]-acetyl)$_2$-(γ-Glu)$_3$-CO-$(CH_2)_{16}$-$CO_2$H; and the C-terminal amino acid is amidated as a C-terminal primary amide (SEQ ID NO: 6). |
| (SEQ ID NO: 7) | P016 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K;<br>wherein $X_1$ is Aib; $X_2$ is αMePhe; $X_3$ is Aib; $X_4$ is Aib;<br>K at position 24 is chemically modified through conjugation to the -amino of the K side-chain with ([2-(2-amino-ethoxy)-ethoxy]-acetyl)3-(Γ-Glu)1-CO-$(CH_2)_{20}$-$CO_2$H; and the C-terminal amino acid is amidated as a C-terminal primary amide (SEQ ID NO: 7). |
| (SEQ ID NO: 8) | P017 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K;<br>wherein $X_1$ is Aib; $X_2$ is αMePhe; $X_3$ is Aib; $X_4$ is Aib;<br>K at position 28 is chemically modified through conjugation to the ε-amino of the K side-chain with ([2-(2-amino-ethoxy)-ethoxy]-acetyl)$_2$-(γ-Glu)$_1$-CO-$(CH_2)_{20}$-$CO_2$H;<br>and the C-terminal amino acid is amidated as a C-terminal primary amide (SEQ ID NO: 8). |
| (SEQ ID NO: 9) | P018 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K;<br>wherein $X_1$ is Aib; $X_2$ is αMePhe; $X_3$ is Aib; $X_4$ is Aib;<br>K at position 28 is chemically modified through conjugation to the ε-amino of the K side-chain with ([2-(2-amino-ethoxy)-ethoxy]-acetyl)$_2$-(γ-Glu)$_3$-CO-$(CH_2)_{16}$-$CO_2$H;<br>and the C-terminal amino acid is amidated as a C-terminal primary amide (SEQ ID NO: 9). |
| (SEQ ID NO: 10) | P019 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K;<br>wherein $X_1$ is Aib; $X_2$ is αMePhe; $X_3$ is Aib; $X_4$ is Aib;<br>K at position 28 is chemically modified through conjugation to the ε-amino of the K side-chain with ([2-(2-amino-ethoxy)-ethoxy]-acetyl)$_3$-(γ-Glu)$_1$-CO-$(CH_2)_{16}$-$CO_2$H;<br>and the C-terminal amino acid is amidated as a C-terminal primary amide (SEQ ID NO: 10). |
| (SEQ ID NO: 11) | P020 | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K;<br>wherein $X_1$ is Aib; $X_2$ is αMePhe; $X_3$ is Aib; $X_4$ is Aib;<br>K at position 28 is chemically modified through conjugation to the ε-amino of the K side-chain with ([2-(2-amino-ethoxy)-ethoxy]-acetyl)$_3$-(γ-Glu)$_1$-CO-$(CH_2)_{20}$-$CO_2$H;<br>and the C-terminal amino acid is amidated as a C-terminal primary amide (SEQ ID NO: 11). |
| (SEQ ID NO: 12) | Formula (I) | Y-$X_1$-E-G-T-$X_2$-T-S-D-Y-$X_3$-I-$X_4$-L-D-K-Q-A-Q-A-E-F-V-K-W-L-L-K-G-G-P-S-S-G-A-P-P-P-S-K;<br>wherein $X_1$ is Aib; $X_2$ is αMePhe; $X_3$ is Aib; $X_4$ is Aib;<br>1, 2, 3 or 4 Ks, which are selected from the group consisting of K at position 16, K at position 24, K at position 28 and K at position 40, are chemically modified through conjugation to the ε-aminos of the K side-chains with ([2-(2-amino-ethoxy)-ethoxy]-acetyl)$_a$-(γ-Glu)$_b$-CO-$(CH_2)_c$-Z, wherein each a is independently an integer from 0 to 5, each b is independently an integer from 0 to 5, and each c is independently an integer from 10 to 24,<br>wherein Z is independently selected from the group consisting of -CH3, carboxylic acids or carboxylic acid bioisosteres, phosphonates or sulfonates, and the C-terminal amino acid is amidated as a C-terminal primary amide (SEQ ID NO: 12). |
| (SEQ ID NO: 13) | Formula (AI) | Y-$X_1$-E-G-T-$X_2$-T-S-D-Y-A11-A12-A13-L-D-K-A17-A-Q-A20-E-F-V-K-W-L-L-K-A29-G-P-S-S-G-A-P-P-P-S-K;<br>wherein $X_1$ is Aib; $X_2$ is αMePhe; A11 is Aib or Ala; A12 is Ala, Ile, Lys, Phe or Pya(4); A13 is Aib, Cha, Leu, αMePhe or aMeTyr; A17 is Gln or Ile; A20 is Ala or Ser; A29 is Gln or Gly,<br>1, 2, 3 or 4 Ks, which are selected from the group consisting of K at position 16, K at position 24, K at position 28 and K at position 40, |

-continued

| No. in sequence listing | Name | Sequence |
|---|---|---| are chemically modified through conjugation to the ε-aminos of the K side-chains with ([2-(2-amino-ethoxy)-ethoxy]-acetyl)$_a$-(γ-Glu)$_b$-CO-(CH$_2$)$_c$-Z, wherein each a is independently an integer from 0 to 5, each b is independently an integer from 0 to 5, and each c is independently an integer from 10 to 24;
wherein Z is independently selected from the group consisting of -CH3, carboxylic acids or carboxylic acid bioisosteres, phosphonates or sulfonates, and the C-terminal amino acid is amidated as a C-terminal primary amide (SEQ ID NO: 13).

SEQ ID NO: 14 — Formula (I) — Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K;
wherein X$_1$ is Aib; X$_2$ is αMePhe; X$_3$ is Aib; X$_4$ is Aib;
1 K or 2 Ks selected from the group consisting of K at position 16, K at position 24, K at position 28 and K at position 40 are chemically modified through conjugation to the e-aminos of the K side-chains with ([2-(2-amino-ethoxy)-ethoxy]-acetyl)$_a$-(γ-Glu)$_b$-CO-(CH$_2$)$_c$-Z,
wherein Z is independently selected from the group consisting of -CH3, carboxylic acids or carboxylic acid bioisosteres, phosphonates or sulfonates, preferably -CO$_2$H,
wherein each a is independently an integer from 0 to 5, each b is independently an integer from 0 to 5, and each c is independently an integer from 10 to 24,
and the C-terminal amino acid is amidated as a C-terminal primary amide (SEQ ID NO: 14)

SEQ ID NO: 15 — Formula (I) — Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K;
wherein X$_1$ is Aib; X$_2$ is αMePhe; X$_3$ is Aib; X$_4$ is Aib;
K at position 24 is chemically modified through conjugation to the E-aminos of the K side-chains with ([2-(2-amino-ethoxy)-ethoxy]-acetyl)$_a$-(γ-Glu)$_b$-CO-(CH$_2$)$_c$-CO$_2$H,
wherein each a is independently an integer from 0 to 5, each b is independently an integer from 0 to 5, and each c is independently an integer from 10 to 24,
and the C-terminal amino acid is amidated as a C-terminal primary amide (SEQ ID NO: 15)

SEQ ID NO: 16 — Formula (I) — Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K;
wherein X$_1$ is Aib; X$_2$ is αMePhe; X$_3$ is Aib; X$_4$ is Aib;
K at position 28 is chemically modified through conjugation to the E-aminos of the K side-chains with ([2-(2-amino-ethoxy)-ethoxy]-acetyl)$_a$-(γ-Glu)$_b$-CO-(CH$_2$)$_c$-CO$_2$H,
wherein each a is independently an integer from 0 to 5, each b is independently an integer from 0 to 5, and each c is independently an integer from 10 to 24,
and the C-terminal amino acid is amidated as a C-terminal primary amide (SEQ ID NO: 16)

SEQ ID NO: 17 — Formula (I) — Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K;
wherein X$_1$ is Aib; X$_2$ is αMePhe; X$_3$ is Aib; X$_4$ is Aib;
K at position 16 is chemically modified through conjugation to the ε-aminos of the K side-chains with ([2-(2-amino-ethoxy)-ethoxy]-acetyl)$_a$-(γ-Glu)$_b$-CO-(CH$_2$)$_c$-CO$_2$H,
wherein each a is independently an integer from 0 to 5, each b is independently an integer from 0 to 5, and each c is independently an integer from 10 to 24,
and the C-terminal amino acid is amidated as a C-terminal primary amide (SEQ ID NO: 17)

SEQ ID NO: 18 — Formula (I) — Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K;
wherein X$_1$ is Aib; X$_2$ is αMePhe; X$_3$ is Aib; X$_4$ is Aib;
K at position 40 is chemically modified through conjugation to the E-aminos of the K side-chains with ([2-(2-amino-ethoxy)-ethoxy]-acetyl)$_a$-(γ-Glu)$_b$-CO-(CH$_2$)$_c$-CO$_2$H,
wherein each a is independently an integer from 0 to 5, each b is independently an integer from 0 to 5, and each c is independently an integer from 10 to 24,
and the C-terminal amino acid is amidated as a C-terminal primary amide (SEQ ID NO: 18)

| No. in sequence listing | Name | Sequence |
|---|---|---|
| SEQ ID NO: 19 | Formula (I) | Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K; wherein X$_1$ is Aib; X$_2$ is αMePhe; X$_3$ is Aib; X$_4$ is Aib; K at position 24 and K at position 28 are chemically modified through conjugation to the ε-aminos of the K side-chains with ([2-(2-amino-ethoxy)-ethoxy]-acetyl)$_a$-(γ-Glu)$_b$-CO-(CH2)$_c$-CO$_2$H, wherein each a is independently an integer from 0 to 5, each b is independently an integer from 0 to 5, and each c is independently an integer from 10 to 22, and the C-terminal amino acid is amidated as a C-terminal primary amide (SEQ ID NO: 19) |
| SEQ ID NO: 20 | Formula (I) | Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K; wherein X$_1$ is Aib; X$_2$ is αMePhe; X$_3$ is Aib; X$_4$ is Aib; K at position 16 and K at position 24 are chemically modified through conjugation to the ε-aminos of the K side-chains with ([2-(2-amino-ethoxy)-ethoxy]-acetyl)$_a$-(γ-Glu)$_b$-CO-(CH2)$_c$-CO$_2$H, wherein each a is independently an integer from 0 to 5, each b is independently an integer from 0 to 5, and each c is independently an integer from 10 to 22, and the C-terminal amino acid is amidated as a C-terminal primary amide (SEQ ID NO: 20) |
| SEQ ID NO: 21 | Formula (I) | Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K; wherein X$_1$ is Aib; X$_2$ is αMePhe; X$_3$ is Aib; X$_4$ is Aib; K at position 16 and K at position 28 are chemically modified through conjugation to the -aminos of the K side-chains with ([2-(2-amino-ethoxy)-ethoxy]-acetyl)$_a$-(γ-Glu)$_b$-CO-(CH$_2$)$_c$-CO$_2$H, wherein each a is independently an integer from 0 to 5, each b is independently an integer from 0 to 5, and each c is independently an integer from 10 to 22, and the C-terminal amino acid is amidated as a C-terminal primary amide (SEQ ID NO: 21) |
| SEQ ID NO: 22 | Formula (I) | Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K; wherein X$_1$ is Aib; X$_2$ is αMePhe; X$_3$ is Aib; X$_4$ is Aib; K at position 16 and K at position 40 are chemically modified through conjugation to the e-aminos of the K side-chains with ([2-(2-amino-ethoxy)-ethoxy]-acetyl)$_a$-(γ-Glu)$_b$-CO-(CH$_2$)$_c$-CO$_2$H, wherein each a is independently an integer from 0 to 5, each b is independently an integer from 0 to 5, and each c is independently an integer from 10 to 22, and the C-terminal amino acid is amidated as a C-terminal primary amide (SEQ ID NO: 22) |
| SEQ ID NO: 23 | Formula (I) | Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K; wherein X$_1$ is Aib; X$_2$ is αMePhe; X$_3$ is Aib; X$_4$ is Aib; K at position 24 and K at position 40 are chemically modified through conjugation to the e-aminos of the K side-chains with ([2-(2-amino-ethoxy)-ethoxy]-acetyl)$_a$-(γ-Glu)$_b$-CO-(CH$_2$)$_c$-CO$_2$H, wherein each a is independently an integer from 0 to 5, each b is independently an integer from 0 to 5, and each c is independently an integer from 10 to 22, and the C-terminal amino acid is amidated as a C-terminal primary amide (SEQ ID NO: 23) |
| SEQ ID NO: 24 | Formula (I) | Y-X$_1$-E-G-T-X$_2$-T-S-D-Y-X$_3$-I-X$_4$-L-D-K-Q-A-Q-A-E-F-V-K-W-L-L-K-G-G-P-S-S-G-A-P-P-P-S-K; wherein X$_1$ is Aib; X$_2$ is αMePhe; X$_3$ is Aib; X$_4$ is Aib; K at position 28 and K at position 40 are chemically modified through conjugation to the -aminos of the K side-chains with ([2-(2-amino-ethoxy)-ethoxy]-acetyl)$_a$-(γ-Glu)$_b$-CO-(CH$_2$)$_c$-CO$_2$H, wherein each a is independently an integer from 0 to 5, each b is independently an integer from 0 to 5, and each c is independently an integer from 10 to 22, |

-continued

| No. in sequence listing | Name | Sequence |
|---|---|---|
| | | and the C-terminal amino acid is amidated as a C-terminal primary amide (SEQ ID NO: 24) |
| (SEQ ID NO: 25) | Formula (AI) | Y-$X_1$-E-G-T-$X_2$-T-S-D-Y-A11-A12-A13-L-D-K-A17-A-Q-A20-E-F-V-K-W-L-L-K-A29-G-P-S-S-G-A-P-P-S-K; wherein $X_1$ is Aib; $X_2$ is αMePhe; A11 is Aib; A12 is Ile; A13 is Aib; A17 is Gln; A20 is Ala; and A29 is Gly, 1 or 2 Ks, which are selected from the group consisting of K at position 16, K at position 24, K at position 28 and K at position 40, are chemically modified through conjugation to the e-aminos of the K side-chains with ([2-(2-amino-ethoxy)-ethoxy]-acetyl)$_a$-(γ-Glu)$_b$-CO-(CH$_2$)$_c$-Z, wherein each a is independently an integer from 0 to 5, each b is independently an integer from 0 to 5, and each c is independently an integer from 10 to 22, whereinZ is independently selected from the group consisting of -CH$_3$, carboxylic acids or carboxylic acid bioisosteres, phosphonates or sulfonates, and the C-terminal amino acid is amidated as a C-terminal primary amide (SEQ ID NO: 25). |
| (SEQ ID NO: 26) | Formula (AI) | Y-$X_1$-E-G-T-$X_2$-T-S-D-Y-A11-A12-A13-L-D-K-A17-A-Q-A20-E-F-V-K-W-L-L-K-A29-G-P-S-S-G-A-P-P-S-K; wherein $X_1$ is Aib; $X_2$ is αMePhe; A11 is Aib; A12 is Ile; A13 is Aib; A17 is Gln; A20 is Ala; A29 is Gly, 1 K, which is selected from the group consisting of K at position 24 and K at position 28, is chemically modified through conjugation to the e-aminos of the K side-chains with ([2-(2-amino-ethoxy)-ethoxy]-acetyl)$_a$-(γ-Glu)$_b$-CO-(CH$_2$)$_c$-Z, wherein each a is independently selected from an integer of 1, 2 and 3, each b is independently selected from an integer of 1, 2 and 3, and each c is independently selected from an integer of 16, 18 and 20, wherein Z is independently selected from the group consisting of -CH$_3$ and carboxylic acids; and the C-terminal amino acid is amidated as a C-terminal primary amide (SEQ ID NO: 26). |

What is claimed is:

1. A compound selected from the group consisting of:
the compound of SEQ ID NO:5, in which K at position 24 is chemically modified through conjugation to the ε-amino of the K side-chain with ([2-(2-amino-ethoxy)-ethoxy]-acetyl)$_2$-(γ-Glu)$_1$-CO—(CH$_2$)$_{20}$—CO$_2$H; and the C-terminal amino acid is amidated as a C-terminal primary amide; and
the compound of SEQ ID NO:7, in which the K at position 24 is chemically modified through conjugation to the ε-amino of the K side-chain with ([2-(2-amino-ethoxy)-ethoxy]-acetyl)$_3$-(γ-Glu)$_1$-CO—(CH$_2$)$_{20}$—CO$_2$H; and the C-terminal amino acid is amidated as a C-terminal primary amide.

2. A pharmaceutical composition comprising the compound according to claim 1, and a pharmaceutically acceptable carrier, diluent or excipient.

* * * * *

SEQUENCE LISTING

Sequence total quantity: 26
SEQ ID NO: 1          moltype = AA  length = 40
FEATURE               Location/Qualifiers
source                1..40
                      mol_type = protein
                      organism = synthetic construct
MOD_RES               2
                      note = Aib
MOD_RES               6
                      note = alpha methyl phenylalanine
MOD_RES               11
                      note = Aib
MOD_RES               13
                      note = Aib
MOD_RES               40
                      note = amidated
SEQUENCE: 1
YXEGTXTSDY XIXLDKQAQA EFVKWLLKGG PSSGAPPPSK                              40

SEQ ID NO: 2          moltype = AA  length = 40
FEATURE               Location/Qualifiers
source                1..40
                      mol_type = protein
                      organism = synthetic construct
MOD_RES               2
                      note = Aib
MOD_RES               6
                      note = alpha methyl phenylalanine
MOD_RES               11
                      note = Aib
MOD_RES               13
                      note = Aib -continued

```
MOD_RES              40
                     note = amidated
SITE                 24
                     note = the epsilon-amino of the K side-chain is conjugated
                     with
                     ([2-(2-amino-ethoxy)-ethoxy]-acetyl)2-(gama-Glu)1-CO-(CH2)1
                     6-CO2H
SEQUENCE: 2
YXEGTXTSDY XIXLDKQAQA EFVKWLLKGG PSSGAPPPSK                                      40

SEQ ID NO: 3         moltype = AA  length = 40
FEATURE              Location/Qualifiers
source               1..40
                     mol_type = protein
                     organism = synthetic construct
MOD_RES              2
                     note = Aib
MOD_RES              6
                     note = alpha methyl phenylalanine
MOD_RES              11
                     note = Aib
MOD_RES              13
                     note = Aib
MOD_RES              40
                     note = amidated
SITE                 28
                     note = the epsilon-amino of the K side-chain is conjugated
                     with
                     ([2-(2-amino-ethoxy)-ethoxy]-acetyl)2-(gama-Glu)1-CO-(CH2)1
                     6-CO2H
SEQUENCE: 3
YXEGTXTSDY XIXLDKQAQA EFVKWLLKGG PSSGAPPPSK                                      40

SEQ ID NO: 4         moltype = AA  length = 40
FEATURE              Location/Qualifiers
source               1..40
                     mol_type = protein
                     organism = synthetic construct
MOD_RES              2
                     note = Aib
MOD_RES              6
                     note = alpha methyl phenylalanine
MOD_RES              11
                     note = Aib
MOD_RES              13
                     note = Aib
MOD_RES              40
                     note = amidated
SITE                 24
                     note = the epsilon-amino of the K side-chain is  conjugatged
                      with
                     ([2-(2-amino-ethoxy)-ethoxy]-acetyl)2-(gama-Glu)1-CO-(CH2)1
                     8-CO2H
SEQUENCE: 4
YXEGTXTSDY XIXLDKQAQA EFVKWLLKGG PSSGAPPPSK                                      40

SEQ ID NO: 5         moltype = AA  length = 40
FEATURE              Location/Qualifiers
source               1..40
                     mol_type = protein
                     organism = synthetic construct
MOD_RES              2
                     note = Aib
MOD_RES              6
                     note = alpha methyl phenylalanine
MOD_RES              11
                     note = Aib
MOD_RES              13
                     note = Aib
MOD_RES              40
                     note = amidated
SITE                 24
                     note = the epsilon-amino of the K side-chain is conjugated
                     with
                     ([2-(2-amino-ethoxy)-ethoxy]-acetyl)2-(gama-Glu)1-CO-(CH2)2
                     0-CO2H
SEQUENCE: 5
YXEGTXTSDY XIXLDKQAQA EFVKWLLKGG PSSGAPPPSK                                      40
```

-continued

```
SEQ ID NO: 6          moltype = AA  length = 40
FEATURE               Location/Qualifiers
source                1..40
                      mol_type = protein
                      organism = synthetic construct
MOD_RES               2
                      note = Aib
MOD_RES               6
                      note = alpha methyl phenylalanine
MOD_RES               11
                      note = Aib
MOD_RES               13
                      note = Aib
MOD_RES               40
                      note = amidated
SITE                  24
                      note = the epsilon-amino of the K side-chain is conjugated
                      with
                      ([2-(2-amino-ethoxy)-ethoxy]-acetyl)2-(gama-Glu)3-CO-(CH2)1
                      6-CO2H
SEQUENCE: 6
YXEGTXTSDY XIXLDKQAQA EFVKWLLKGG PSSGAPPPSK                              40

SEQ ID NO: 7          moltype = AA  length = 40
FEATURE               Location/Qualifiers
source                1..40
                      mol_type = protein
                      organism = synthetic construct
MOD_RES               2
                      note = Aib
MOD_RES               6
                      note = alpha methyl phenylalanine
MOD_RES               11
                      note = Aib
MOD_RES               13
                      note = Aib
MOD_RES               40
                      note = amidated
SITE                  24
                      note = the epsilon-amino of the K side-chain is conjugated
                      with
                      ([2-(2-amino-ethoxy)-ethoxy]-acetyl)3-(gama-Glu)1-CO-(CH2)2
                      0-CO2H
SEQUENCE: 7
YXEGTXTSDY XIXLDKQAQA EFVKWLLKGG PSSGAPPPSK                              40

SEQ ID NO: 8          moltype = AA  length = 40
FEATURE               Location/Qualifiers
source                1..40
                      mol_type = protein
                      organism = synthetic construct
MOD_RES               2
                      note = Aib
MOD_RES               6
                      note = alpha methyl phenylalanine
MOD_RES               11
                      note = Aib
MOD_RES               13
                      note = Aib
MOD_RES               40
                      note = amidated
SITE                  28
                      note = the epsilon-amino of the K side-chain is conjugated
                      with
                      ([2-(2-amino-ethoxy)-ethoxy]-acetyl)2-(gama-Glu)1-CO-(CH2)2
                      0-CO2H
SEQUENCE: 8
YXEGTXTSDY XIXLDKQAQA EFVKWLLKGG PSSGAPPPSK                              40

SEQ ID NO: 9          moltype = AA  length = 40
FEATURE               Location/Qualifiers
source                1..40
                      mol_type = protein
                      organism = synthetic construct
MOD_RES               2
                      note = Aib
MOD_RES               6
                      note = alpha methyl phenylalanine
MOD_RES               11
```

-continued

```
                              note = Aib
MOD_RES                       13
                              note = Aib
MOD_RES                       40
                              note = amidated
SITE                          28
                              note = the epsilon-amino of the K side-chain is conjugated
                              with
                              ([2-(2-amino-ethoxy)-ethoxy]-acetyl)2-(gama-Glu)3-CO-(CH2)1
                              6-CO2H
SEQUENCE: 9
YXEGTXTSDY XIXLDKQAQA EFVKWLLKGG PSSGAPPPSK                                        40

SEQ ID NO: 10                 moltype = AA  length = 40
FEATURE                       Location/Qualifiers
source                        1..40
                              mol_type = protein
                              organism = synthetic construct
MOD_RES                       2
                              note = Aib
MOD_RES                       6
                              note = alpha methyl phenylalanine
MOD_RES                       11
                              note = Aib
MOD_RES                       13
                              note = Aib
MOD_RES                       40
                              note = amidated
SITE                          28
                              note = the epsilon-amino of the K side-chain is conjugated
                              with
                              ([2-(2-amino-ethoxy)-ethoxy]-acetyl)3-(gama-Glu)1-CO-(CH2)1
                              6-CO2H
SEQUENCE: 10
YXEGTXTSDY XIXLDKQAQA EFVKWLLKGG PSSGAPPPSK                                        40

SEQ ID NO: 11                 moltype = AA  length = 40
FEATURE                       Location/Qualifiers
source                        1..40
                              mol_type = protein
                              organism = synthetic construct
MOD_RES                       2
                              note = Aib
MOD_RES                       6
                              note = alpha methyl phenylalanine
MOD_RES                       11
                              note = Aib
MOD_RES                       13
                              note = Aib
MOD_RES                       40
                              note = amidated
SITE                          28
                              note = the epsilon-amino of the K side-chain is conjugated
                              with
                              ([2-(2-amino-ethoxy)-ethoxy]-acetyl)3-(gama-Glu)1-CO-(CH2)2
                              0-CO2H
SEQUENCE: 11
YXEGTXTSDY XIXLDKQAQA EFVKWLLKGG PSSGAPPPSK                                        40

SEQ ID NO: 12                 moltype = AA  length = 40
FEATURE                       Location/Qualifiers
source                        1..40
                              mol_type = protein
                              organism = synthetic construct
MOD_RES                       2
                              note = Aib
MOD_RES                       6
                              note = alpha methyl phenylalanine
MOD_RES                       11
                              note = Aib
MOD_RES                       13
                              note = Aib
MOD_RES                       40
                              note = amidated
SITE                          24
                              note = the epsilon-amino of the K side-chain may be
                              conjugated with
                              ([2-(2-amino-ethoxy)-ethoxy]-acetyl)a-(gama-Glu)b-CO-(CH2)c
                              -Z, wherein each a is independently an integer from 0 to
```

-continued

```
                    5, each b is independently an integer from 0 to 5, and
                    each c is independently an integer from 10 to 24, wherein
                    Z is independently selected from the group consisting of
                    -CH3, carboxylic acids or carboxylic acid bioisosteres,
                    phosphonates or sulfonates
SITE                16
                    note = the epsilon-amino of the K side-chain may be
                    conjugated with
                    ([2-(2-amino-ethoxy)-ethoxy]-acetyl)a-(gama-Glu)b-CO-(CH2)c
                    -Z, wherein each a is independently an integer from 0 to
                    5, each b is independently an integer from 0 to 5, and
                    each c is independently an integer from 10 to 24, wherein
                    Z is independently selected from the group consisting of
                    -CH3, carboxylic acids or carboxylic acid bioisosteres,
                    phosphonates or sulfonates
SITE                28
                    note = the epsilon-amino of the K side-chain may be
                    conjugated with
                    ([2-(2-amino-ethoxy)-ethoxy]-acetyl)a-(gama-Glu)b-CO-(CH2)c
                    -Z, wherein each a is independently an integer from 0 to
                    5, each b is independently an integer from 0 to 5, and
                    each c is independently an integer from 10 to 24, wherein
                    Z is independently selected from the group consisting of
                    -CH3, carboxylic acids or carboxylic acid bioisosteres,
                    phosphonates or sulfonates
SITE                40
                    note = the epsilon-amino of the K side-chain may be
                    conjugated with
                    ([2-(2-amino-ethoxy)-ethoxy]-acetyl)a-(gama-Glu)b-CO-(CH2)c
                    -Z, wherein each a is independently an integer from 0 to
                    5, each b is independently an integer from 0 to 5, and
                    each c is independently an integer from 10 to 24, wherein
                    Z is independently selected from the group consisting of
                    -CH3, carboxylic acids or carboxylic acid bioisosteres,
                    phosphonates or sulfonates
SEQUENCE: 12
YXEGTXTSDY XIXLDKQAQA EFVKWLLKGG PSSGAPPPSK                          40

SEQ ID NO: 13           moltype = AA   length = 40
FEATURE                 Location/Qualifiers
source                  1..40
                        mol_type = protein
                        organism = synthetic construct
VAR_SEQ                 2
                        note = Aib
MOD_RES                 6
                        note = alpha methyl phenylalanine
VAR_SEQ                 11
                        note = Aib or Ala
VAR_SEQ                 13
                        note = Aib, cyclohexylalanine, Leu, alpha methyl
                        phenylalanine or alpha methyl tyrosine
SITE                    24
                        note = the epsilon-amino of the K side-chain may be
                        conjugated with
                        ([2-(2-amino-ethoxy)-ethoxy]-acetyl)a-(gama-Glu)b-CO-(CH2)c
                        -Z, whereineach a is independently an integer from 0 to 5,
                        each b is independently an integer from 0 to 5, and each c
                        is independently an integer from 10 to 24, wherein Z is
                        independently selected from the group consisting of -CH3,
                        carboxylic acids or carboxylic acid bioisosteres,
                        phosphonates or sulfonates
VAR_SEQ                 12
                        note = Ala, Ile, Lys, Phe or 4-pyridinyl alanine
VAR_SEQ                 17
                        note = Gln or Ile
VAR_SEQ                 20
                        note = Ala or Ser
VAR_SEQ                 29
                        note = Gln or Gly
SITE                    16
                        note = the epsilon-amino of the K side-chain may be
                        conjugated with
                        ([2-(2-amino-ethoxy)-ethoxy]-acetyl)a-(gama-Glu)b-CO-(CH2)c
                        -Z, wherein each a is independently an integer from 0 to
                        5, each b is independently an integer from 0 to 5, and
                        each c is independently an integer from 10 to 24, wherein
                        Z is independently selected from the group consisting of
                        -CH3, carboxylic acids or carboxylic acid bioisosteres,
```

-continued

```
                        phosphonates or sulfonates
SITE                    28
                        note = the epsilon-amino of the K side-chain may be
                         conjugated with
                         ([2-(2-amino-ethoxy)-ethoxy]-acetyl)a-(gama-Glu)b-CO-(CH2)c
                         -Z, wherein each a is independently an integer from 0 to
                         5, each b is independently an integer from 0 to 5, and
                         each c is independently an integer from 10 to 24, wherein
                         Z is independently selected from the group consisting of
                         -CH3, carboxylic acids or carboxylic acid bioisosteres,
                         phosphonates or sulfonates
SITE                    40
                        note = the epsilon-amino of the K side-chain may be
                         conjugated with
                         ([2-(2-amino-ethoxy)-ethoxy]-acetyl)a-(gama-Glu)b-CO-(CH2)c
                         -Z, wherein each a is independently an integer from 0 to
                         5, each b is independently an integer from 0 to 5, and
                         each c is independently an integer from 10 to 24, wherein
                         Z is independently selected from the group consisting of
                         -CH3, carboxylic acids or carboxylic acid bioisosteres,
                         phosphonates or sulfonates
MOD_RES                 40
                        note = amidated
SEQUENCE: 13
YXEGTXTSDY XXXLDKXAQX EFVKWLLKXG PSSGAPPPSK                              40

SEQ ID NO: 14           moltype = AA  length = 40
FEATURE                 Location/Qualifiers
source                  1..40
                        mol_type = protein
                        organism = synthetic construct
MOD_RES                 2
                        note = Aib
MOD_RES                 6
                        note = alpha methyl phenylalanine
MOD_RES                 11
                        note = Aib
MOD_RES                 13
                        note = Aib
MOD_RES                 40
                        note = amidated
SITE                    24
                        note = the epsilon-amino of the K side-chain may be
                         conjugated with
                         ([2-(2-amino-ethoxy)-ethoxy]-acetyl)a-(gama-Glu)b-CO-(CH2)c
                         -Z, wherein each a is independently an integer from 0 to
                         5, each b is independently an integer from 0 to 5, and
                         each c is independently an integer from 10 to 24, wherein
                         Z is independently selected from the group consisting of
                         -CH3, carboxylic acids or carboxylic acid bioisosteres,
                         phosphonates or sulfonates, preferably -CO2H
SITE                    16
                        note = the epsilon-amino of the K side-chain may be
                         conjugated with
                         ([2-(2-amino-ethoxy)-ethoxy]-acetyl)a-(gama-Glu)b-CO-(CH2)c
                         -Z, wherein each a is independently an integer from 0 to
                         5, each b is independently an integer from 0 to 5, and
                         each c is independently an integer from 10 to 24, wherein
                         Z is independently selected from the group consisting of
                         -CH3, carboxylic acids or carboxylic acid bioisosteres,
                         phosphonates or sulfonates, preferably -CO2H
SITE                    28
                        note = the epsilon-amino of the K side-chain may be
                         conjugated with
                         ([2-(2-amino-ethoxy)-ethoxy]-acetyl)a-(gama-Glu)b-CO-(CH2)c
                         -Z, wherein each a is independently an integer from 0 to
                         5, each b is independently an integer from 0 to 5, and
                         each c is independently an integer from 10 to 24, wherein
                         Z is independently selected from the group consisting of
                         -CH3, carboxylic acids or carboxylic acid bioisosteres,
                         phosphonates or sulfonates, preferably -CO2H
SITE                    40
                        note = the epsilon-amino of the K side-chain may be
                         conjugated with
                         ([2-(2-amino-ethoxy)-ethoxy]-acetyl)a-(gama-Glu)b-CO-(CH2)c
                         -Z, wherein each a is independently an integer from 0 to
                         5, each b is independently an integer from 0 to 5, and
                         each c is independently an integer from 10 to 24, wherein
                         Z is independently selected from the group consisting of
```

```
                            -CH3, carboxylic acids or carboxylic acid bioisosteres,
                            phosphonates or sulfonates, preferably -CO2H
SEQUENCE: 14
YXEGTXTSDY XIXLDKQAQA EFVKWLLKGG PSSGAPPPSK                              40

SEQ ID NO: 15             moltype = AA  length = 40
FEATURE                   Location/Qualifiers
source                    1..40
                          mol_type = protein
                          organism = synthetic construct
MOD_RES                   2
                          note = Aib
MOD_RES                   6
                          note = alpha methyl phenylalanine
MOD_RES                   11
                          note = Aib
MOD_RES                   13
                          note = Aib
MOD_RES                   40
                          note = amidated
SITE                      24
                          note = the epsilon-amino of the K side-chain may be
                           conjugated with
                           ([2-(2-amino-ethoxy)-ethoxy]-acetyl)a-(gama-Glu)b-CO-(CH2)c
                           -CO2H, wherein each a is independently an integer from 0
                           to 5, each b is independently an integer from 0 to 5, and
                           each c is independently an integer from 10 to 24
SEQUENCE: 15
YXEGTXTSDY XIXLDKQAQA EFVKWLLKGG PSSGAPPPSK                              40

SEQ ID NO: 16             moltype = AA  length = 40
FEATURE                   Location/Qualifiers
source                    1..40
                          mol_type = protein
                          organism = synthetic construct
MOD_RES                   2
                          note = Aib
MOD_RES                   6
                          note = alpha methyl phenylalanine
MOD_RES                   11
                          note = Aib
MOD_RES                   13
                          note = Aib
MOD_RES                   40
                          note = amidated
SITE                      28
                          note = the epsilon-amino of the K side-chain may be
                           conjugated with
                           ([2-(2-amino-ethoxy)-ethoxy]-acetyl)a-(gama-Glu)b-CO-(CH2)c
                           -CO2H, wherein each a is independently an integer from 0
                           to 5, each b is independently an integer from 0 to 5, and
                           each c is independently an integer from 10 to 24
SEQUENCE: 16
YXEGTXTSDY XIXLDKQAQA EFVKWLLKGG PSSGAPPPSK                              40

SEQ ID NO: 17             moltype = AA  length = 40
FEATURE                   Location/Qualifiers
source                    1..40
                          mol_type = protein
                          organism = synthetic construct
MOD_RES                   2
                          note = Aib
MOD_RES                   6
                          note = alpha methyl phenylalanine
MOD_RES                   11
                          note = Aib
MOD_RES                   13
                          note = Aib
MOD_RES                   40
                          note = amidated
SITE                      16
                          note = the epsilon-amino of the K side-chain may be
                           conjugated with
                           ([2-(2-amino-ethoxy)-ethoxy]-acetyl)a-(gama-Glu)b-CO-(CH2)c
                           -CO2H, wherein each a is independently an integer from 0
                           to 5, each b is independently an integer from 0 to 5, and
                           each c is independently an integer from 10 to 24
SEQUENCE: 17
YXEGTXTSDY XIXLDKQAQA EFVKWLLKGG PSSGAPPPSK                              40
```

-continued

```
SEQ ID NO: 18          moltype = AA   length = 40
FEATURE                Location/Qualifiers
source                 1..40
                       mol_type = protein
                       organism = synthetic construct
MOD_RES                2
                       note = Aib
MOD_RES                6
                       note = alpha methyl phenylalanine
MOD_RES                11
                       note = Aib
MOD_RES                13
                       note = Aib
MOD_RES                40
                       note = amidated
SITE                   40
                       note = the epsilon-amino of the K side-chain may be
                        conjugated with
                        ([2-(2-amino-ethoxy)-ethoxy]-acetyl)a-(gama-Glu)b-CO-(CH2)c
                        -CO2H, wherein each a is independently an integer from 0
                        to 5, each b is independently an integer from 0 to 5, and
                        each c is independently an integer from 10 to 24
SEQUENCE: 18
YXEGTXTSDY XIXLDKQAQA EFVKWLLKGG PSSGAPPPSK                            40

SEQ ID NO: 19          moltype = AA   length = 40
FEATURE                Location/Qualifiers
source                 1..40
                       mol_type = protein
                       organism = synthetic construct
MOD_RES                2
                       note = Aib
MOD_RES                6
                       note = alpha methyl phenylalanine
MOD_RES                11
                       note = Aib
MOD_RES                13
                       note = Aib
MOD_RES                40
                       note = amidated
SITE                   24
                       note = the epsilon-amino of the K side-chain may be
                        conjugated with
                        ([2-(2-amino-ethoxy)-ethoxy]-acetyl)a-(gama-Glu)b-CO-(CH2)c
                        -CO2H, wherein each a is independently an integer from 0
                        to 5, each b is independently an integer from 0 to 5, and
                        each c is independently an integer from 10 to 22
SITE                   28
                       note = the epsilon-amino of the K side-chain may be
                        conjugated with
                        ([2-(2-amino-ethoxy)-ethoxy]-acetyl)a-(gama-Glu)b-CO-(CH2)c
                        -CO2H, wherein each a is independently an integer from 0
                        to 5, each b is independently an integer from 0 to 5, and
                        each c is independently an integer from 10 to 22
SEQUENCE: 19
YXEGTXTSDY XIXLDKQAQA EFVKWLLKGG PSSGAPPPSK                            40

SEQ ID NO: 20          moltype = AA   length = 40
FEATURE                Location/Qualifiers
source                 1..40
                       mol_type = protein
                       organism = synthetic construct
MOD_RES                2
                       note = Aib
MOD_RES                6
                       note = alpha methyl phenylalanine
MOD_RES                11
                       note = Aib
MOD_RES                13
                       note = Aib
MOD_RES                40
                       note = amidated
SITE                   24
                       note = the epsilon-amino of the K side-chain may be
                        conjugated with
                        ([2-(2-amino-ethoxy)-ethoxy]-acetyl)a-(gama-Glu)b-CO-(CH2)c
                        -CO2H, wherein each a is independently an integer from 0
                        to 5, each b is independently an integer from 0 to 5, and
```

-continued

```
                            each c is independently an integer from 10 to 22
SITE                        16
                            note = the epsilon-amino of the K side-chain may be
                            conjugated with
                            ([2-(2-amino-ethoxy)-ethoxy]-acetyl)a-(gama-Glu)b-CO-(CH2)c
                            -CO2H, wherein each a is independently an integer from 0
                            to 5, each b is independently an integer from 0 to 5, and
                            each c is independently an integer from 10 to 22
SEQUENCE: 20
YXEGTXTSDY XIXLDKQAQA EFVKWLLKGG PSSGAPPPSK                              40

SEQ ID NO: 21               moltype = AA  length = 40
FEATURE                     Location/Qualifiers
source                      1..40
                            mol_type = protein
                            organism = synthetic construct
MOD_RES                     2
                            note = Aib
MOD_RES                     6
                            note = alpha methyl phenylalanine
MOD_RES                     11
                            note = Aib
MOD_RES                     13
                            note = Aib
MOD_RES                     40
                            note = amidated
SITE                        16
                            note = the epsilon-amino of the K side-chain may be
                            conjugated with
                            ([2-(2-amino-ethoxy)-ethoxy]-acetyl)a-(gama-Glu)b-CO-(CH2)c
                            -CO2H, wherein each a is independently an integer from 0
                            to 5, each b is independently an integer from 0 to 5, and
                            each c is independently an integer from 10 to 22
SITE                        28
                            note = the epsilon-amino of the K side-chain may be
                            conjugated with
                            ([2-(2-amino-ethoxy)-ethoxy]-acetyl)a-(gama-Glu)b-CO-(CH2)c
                            -CO2H, wherein each a is independently an integer from 0
                            to 5, each b is independently an integer from 0 to 5, and
                            each c is independently an integer from 10 to 22
SEQUENCE: 21
YXEGTXTSDY XIXLDKQAQA EFVKWLLKGG PSSGAPPPSK                              40

SEQ ID NO: 22               moltype = AA  length = 40
FEATURE                     Location/Qualifiers
source                      1..40
                            mol_type = protein
                            organism = synthetic construct
MOD_RES                     2
                            note = Aib
MOD_RES                     6
                            note = alpha methyl phenylalanine
MOD_RES                     11
                            note = Aib
MOD_RES                     13
                            note = Aib
MOD_RES                     40
                            note = amidated
SITE                        16
                            note = the epsilon-amino of the K side-chain may be
                            conjugated with
                            ([2-(2-amino-ethoxy)-ethoxy]-acetyl)a-(gama-Glu)b-CO-(CH2)c
                            -CO2H, wherein each a is independently an integer from 0
                            to 5, each b is independently an integer from 0 to 5, and
                            each c is independently an integer from 10 to 22
SITE                        40
                            note = the epsilon-amino of the K side-chain may be
                            conjugated with
                            ([2-(2-amino-ethoxy)-ethoxy]-acetyl)a-(gama-Glu)b-CO-(CH2)c
                            -CO2H, wherein each a is independently an integer from 0
                            to 5, each b is independently an integer from 0 to 5, and
                            each c is independently an integer from 10 to 22
SEQUENCE: 22
YXEGTXTSDY XIXLDKQAQA EFVKWLLKGG PSSGAPPPSK                              40

SEQ ID NO: 23               moltype = AA  length = 40
FEATURE                     Location/Qualifiers
source                      1..40
                            mol_type = protein
```

```
                       organism = synthetic construct
MOD_RES                2
                       note = Aib
MOD_RES                6
                       note = alpha methyl phenylalanine
MOD_RES                11
                       note = Aib
MOD_RES                13
                       note = Aib
MOD_RES                40
                       note = amidated
SITE                   24
                       note = the epsilon-amino of the K side-chain may be
                        conjugated with
                        ([2-(2-amino-ethoxy)-ethoxy]-acetyl)a-(gama-Glu)b-CO-(CH2)c
                        -CO2H, wherein each a is independently an integer from 0
                        to 5, each b is independently an integer from 0 to 5, and
                        each c is independently an integer from 10 to 22
SITE                   40
                       note = the epsilon-amino of the K side-chain may be
                        conjugated with
                        ([2-(2-amino-ethoxy)-ethoxy]-acetyl)a-(gama-Glu)b-CO-(CH2)c
                        -CO2H, wherein each a is independently an integer from 0
                        to 5, each b is independently an integer from 0 to 5, and
                        each c is independently an integer from 10 to 22
SEQUENCE: 23
YXEGTXTSDY XIXLDKQAQA EFVKWLLKGG PSSGAPPPSK                         40

SEQ ID NO: 24          moltype = AA  length = 40
FEATURE                Location/Qualifiers
source                 1..40
                       mol_type = protein
                       organism = synthetic construct
MOD_RES                2
                       note = Aib
MOD_RES                6
                       note = alpha methyl phenylalanine
MOD_RES                11
                       note = Aib
MOD_RES                13
                       note = Aib
MOD_RES                40
                       note = amidated
SITE                   28
                       note = the epsilon-amino of the K side-chain may be
                        conjugated with
                        ([2-(2-amino-ethoxy)-ethoxy]-acetyl)a-(gama-Glu)b-CO-(CH2)c
                        -CO2H, wherein each a is independently an integer from 0
                        to 5, each b is independently an integer from 0 to 5, and
                        each c is independently an integer from 10 to 22
SITE                   40
                       note = the epsilon-amino of the K side-chain may be
                        conjugated with
                        ([2-(2-amino-ethoxy)-ethoxy]-acetyl)a-(gama-Glu)b-CO-(CH2)c
                        -CO2H, wherein each a is independently an integer from 0
                        to 5, each b is independently an integer from 0 to 5, and
                        each c is independently an integer from 10 to 22
SEQUENCE: 24
YXEGTXTSDY XIXLDKQAQA EFVKWLLKGG PSSGAPPPSK                         40

SEQ ID NO: 25          moltype = AA  length = 40
FEATURE                Location/Qualifiers
source                 1..40
                       mol_type = protein
                       organism = synthetic construct
VAR_SEQ                2
                       note = Aib
MOD_RES                6
                       note = alpha methyl phenylalanine
VAR_SEQ                11
                       note = Aib
VAR_SEQ                13
                       note = Aib
SITE                   24
                       note = the epsilon-amino of the K side-chain may be
                        conjugated with
                        ([2-(2-amino-ethoxy)-ethoxy]-acetyl)a-(gama-Glu)b-CO-(CH2)c
                        -Z, wherein each a is independently an integer from 0 to
                        5, each b is independently an integer from 0 to 5, and
```

-continued

```
                       each c is independently an integer from 10 to 22, wherein
                       Z is independently selected from the group consisting of
                       -CH3, carboxylic acids or carboxylic acid bioisosteres,
                       phosphonates or sulfonates
VAR_SEQ                12
                       note = Ile
VAR_SEQ                17
                       note = Gln
VAR_SEQ                20
                       note = Ala
VAR_SEQ                29
                       note = Gly
SITE                   16
                       note = the epsilon-amino of the K side-chain may be
                       conjugated with
                       ([2-(2-amino-ethoxy)-ethoxy]-acetyl)a-(gama-Glu)b-CO-(CH2)c
                       -Z, wherein each a is independently an integer from 0 to
                       5, each b is independently an integer from 0 to 5, and
                       each c is independently an integer from 10 to 22, wherein
                       Z is independently selected from the group consisting of
                       -CH3, carboxylic acids or carboxylic acid bioisosteres,
                       phosphonates or sulfonates
SITE                   28
                       note = the epsilon-amino of the K side-chain may be
                       conjugated with
                       ([2-(2-amino-ethoxy)-ethoxy]-acetyl)a-(gama-Glu)b-CO-(CH2)c
                       -Z, wherein each a is independently an integer from 0 to
                       5, each b is independently an integer from 0 to 5, and
                       each c is independently an integer from 10 to 22, wherein
                       Z is independently selected from the group consisting of
                       -CH3, carboxylic acids or carboxylic acid bioisosteres,
                       phosphonates or sulfonates
SITE                   40
                       note = the epsilon-amino of the K side-chain may be
                       conjugated with
                       ([2-(2-amino-ethoxy)-ethoxy]-acetyl)a-(gama-Glu)b-CO-(CH2)c
                       -Z, wherein each a is independently an integer from 0 to
                       5, each b is independently an integer from 0 to 5, and
                       each c is independently an integer from 10 to 22, wherein
                       Z is independently selected from the group consisting of
                       -CH3, carboxylic acids or carboxylic acid bioisosteres,
                       phosphonates or sulfonates
MOD_RES                40
                       note = amidated
SEQUENCE: 25
YXEGTXTSDY XXXLDKXAQX EFVKWLLKXG PSSGAPPPSK                              40

SEQ ID NO: 26          moltype = AA   length = 40
FEATURE                Location/Qualifiers
source                 1..40
                       mol_type = protein
                       organism = synthetic construct
VAR_SEQ                2
                       note = Aib
MOD_RES                6
                       note = alpha methyl phenylalanine
VAR_SEQ                11
                       note = Aib
VAR_SEQ                13
                       note = Aib
SITE                   24
                       note = the epsilon-amino of the K side-chain may be
                       conjugated with
                       ([2-(2-amino-ethoxy)-ethoxy]-acetyl)a-(gama-Glu)b-CO-(CH2)c
                       -Z, wherein each a is independently an integer of 1, 2 and
                       3, each b is independently an integer of 1, 2 and 3, and
                       each c is independently an integer of 16, 18 and 20,
                       wherein Z is independently selected from the group
                       consisting of -CH3, carboxylic acids or carboxylic acid
                       bioisosteres, phosphonates or sulfonates
VAR_SEQ                12
                       note = Ile
VAR_SEQ                17
                       note = Gln
VAR_SEQ                20
                       note = Ala
VAR_SEQ                29
                       note = Gly
SITE                   28
```

-continued

```
                  note = the epsilon-amino of the K side-chain may be
                  conjugated with
                  ([2-(2-amino-ethoxy)-ethoxy]-acetyl)a-(gama-Glu)b-CO-(CH2)c
                  -Z, wherein each a is independently an integer of 1, 2 and
                  3, each b is independently an integer of 1, 2 and 3, and
                  each c is independently an integer of 16, 18 and 20,
                  wherein Z is independently selected from the group
                  consisting of -CH3, carboxylic acids or carboxylic acid
                  bioisosteres, phosphonates or sulfonates
MOD_RES           40
                  note = amidated
SEQUENCE: 26
YXEGTXTSDY XXXLDKXAQX EFVKWLLKXG PSSGAPPPSK                    40
```